(12) United States Patent
Dong et al.

(10) Patent No.: US 10,507,209 B2
(45) Date of Patent: Dec. 17, 2019

(54) QUINAZOLINE DERIVATIVES SUBSTITUTED BY ANILINE, PREPARATION METHOD AND USE THEREOF

(71) Applicant: XUANZHU PHARMA CO., LTD., Jinan, Shandong Province (CN)

(72) Inventors: Yanyan Dong, Jinan (CN); Chengkon Shih, Jinan (CN)

(73) Assignee: XUANZHU PHARMA CO, LTD., Jinan, Shandong Province (CN)

( * ) Notice: Subject to any disclaimer, the term of this patent is extended or adjusted under 35 U.S.C. 154(b) by 0 days.

(21) Appl. No.: 15/670,160

(22) Filed: Aug. 7, 2017

(65) Prior Publication Data

US 2017/0333433 A1 Nov. 23, 2017

Related U.S. Application Data

(63) Continuation-in-part of application No. 13/818,367, filed as application No. PCT/CN2011/001466 on Aug. 30, 2011, now Pat. No. 9,730,934.

(30) Foreign Application Priority Data

Aug. 30, 2010 (CN) .......................... 2010 1 0266177

(51) Int. Cl.
| | |
|---|---|
| A61K 31/517 | (2006.01) |
| C07D 239/86 | (2006.01) |
| C07D 401/12 | (2006.01) |
| C07D 403/12 | (2006.01) |
| C07D 403/14 | (2006.01) |
| C07D 405/12 | (2006.01) |
| C07D 409/12 | (2006.01) |
| C07D 413/14 | (2006.01) |
| C07D 451/02 | (2006.01) |
| C07D 451/06 | (2006.01) |
| C07D 471/04 | (2006.01) |
| C07D 471/08 | (2006.01) |
| C07D 471/10 | (2006.01) |
| C07D 487/04 | (2006.01) |
| C07D 487/10 | (2006.01) |
| C07D 491/08 | (2006.01) |
| C07D 491/107 | (2006.01) |

(Continued)

(52) U.S. Cl.
CPC ........ *A61K 31/517* (2013.01); *A61K 31/5377* (2013.01); *A61K 45/06* (2013.01); *C07D 239/86* (2013.01); *C07D 239/94* (2013.01); *C07D 401/12* (2013.01); *C07D 403/12* (2013.01); *C07D 403/14* (2013.01); *C07D 405/12* (2013.01); *C07D 409/12* (2013.01); *C07D 413/14* (2013.01); *C07D 451/02* (2013.01); *C07D 451/06* (2013.01); *C07D 471/04* (2013.01); *C07D 471/08* (2013.01); *C07D 471/10* (2013.01); *C07D 487/04* (2013.01); *C07D 487/08* (2013.01); *C07D 487/10* (2013.01); *C07D 491/08* (2013.01); *C07D 491/107* (2013.01); *C07D 493/08* (2013.01)

(58) Field of Classification Search
CPC .............. A61K 31/517; A61K 31/5377; A61K 31/5386
USPC ............................................... 514/266.4, 313
See application file for complete search history.

(56) References Cited

U.S. PATENT DOCUMENTS

| 6,127,374 A | 10/2000 | Bridges |
|---|---|---|
| 6,562,818 B1 | 5/2003 | Bridges |

(Continued)

FOREIGN PATENT DOCUMENTS

| CN | 101356171 A | 1/2009 |
|---|---|---|
| CN | 102382065 A | 3/2012 |

(Continued)

OTHER PUBLICATIONS

Cecil's Textbook of Medicine (2000) (Year: 2000).*

(Continued)

*Primary Examiner* — Timothy P Thomas
*Assistant Examiner* — George W Kosturko
(74) *Attorney, Agent, or Firm* — Clark & Elbing LLP

(57) ABSTRACT

The invention relates to quinazoline derivatives substituted by aniline which are represented by the below formula (I), pharmaceutical acceptable salts and stereoisomer thereof, wherein these groups of $R^1$, $R^2$, $R^3$, $R^4$, $R^5$, $R^6$, L and n have the meanings given in the specification. The invention also relates to preparation methods, pharmaceutical compositions, pharmaceutical preparation and the use for preparation of medicine of treating excessive hyperplasia and chronic obstructive pulmonary disease and uses for treating excessive hyperplasia and chronic obstructive pulmonary disease thereof.

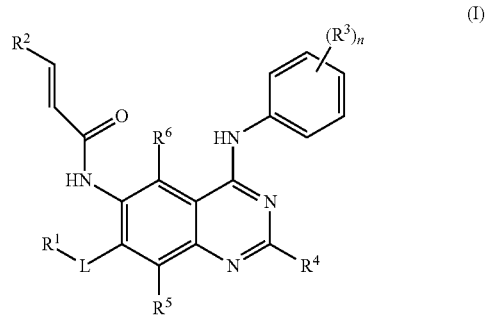

3 Claims, No Drawings

(51) Int. Cl.
*C07D 493/08* (2006.01)
*C07D 239/94* (2006.01)
*C07D 487/08* (2006.01)
*A61K 45/06* (2006.01)
*A61K 31/5377* (2006.01)

(56) References Cited

U.S. PATENT DOCUMENTS

| | | | |
|---|---|---|---|
| 9,370,934 B2* | 6/2016 | Asauchi | B41J 2/17513 |
| 9,586,939 B2* | 3/2017 | Wu | C07D 403/12 |
| 9,730,934 B2* | 8/2017 | Huang | C07D 403/14 |
| 9,956,222 B2* | 5/2018 | Wu | C07D 403/12 |
| 2002/0082270 A1* | 6/2002 | Himmelsbach | C07D 403/12 |
| | | | 514/266.2 |
| 2009/0306044 A1 | 12/2009 | Solca et al. | |
| 2011/0034689 A1 | 2/2011 | Lyssikatos et al. | |
| 2013/0184297 A1* | 7/2013 | Huang | C07D 403/14 |
| | | | 514/266.22 |

FOREIGN PATENT DOCUMENTS

| | | | | |
|---|---|---|---|---|
| CN | 102452989 A | 5/2012 | | |
| CN | 109381469 A | 2/2019 | | |
| DE | 10042061 A1 | 3/2002 | | |
| JP | 2004507533 A | 3/2004 | | |
| JP | 2006505509 A | 2/2006 | | |
| JP | 2006517959 A | 8/2006 | | |
| JP | 2009515851 A | 4/2009 | | |
| JP | 2009515988 A | 4/2009 | | |
| JP | 2009523737 A | 6/2009 | | |
| WO | WO-97/38983 A1 | 10/1997 | | |
| WO | WO-2004/006846 A2 | 1/2004 | | |
| WO | WO-2004006846 A2 * | 1/2004 | | C07D 239/94 |
| WO | WO-2012/158979 A1 | 11/2012 | | |
| WO | WO-2012/159457 A1 | 11/2012 | | |

OTHER PUBLICATIONS

Wheeler et al., (Nat Rev Clin Oncol. vol. 7 pp. 493-507 published online Sep. 2010) (Year: 2010).*

Smaill et al (J. Med Chem vol. 43 pp. 1380-1397. Published 2000) (Year: 2000).*

Chen, "Computational Study of the Binding Mode of Epidermal Growth Factor Receptor Kinase Inhibitors," *Chem. Bio. Drug Des.* 71:434-446 (2008).

Smaill et al., "Tyrosine kinase inhibitors. 17. Irreversible inhibitors of the epidermal growth factor receptor: 4-(phenylamino)quinazoline- and 4-(phenylamino)pyrido[3,2-d]pyrimidine-6-acrylamides bearing additional solubilizing functions," J Med Chem. 43(7):1380-97 (2000).

International Search Report for International Application No. PCT/CN2011/001466, dated Dec. 8, 2011 (6 pages).

International Preliminary Report on Patentability for International Application No. PCT/CN2011/001466, dated Mar. 5, 2013 (7 pages).

Written Opinion of the International Searching Authority for International Application No. PCT/CN2011/001466, dated Dec. 8, 2011 (6 pages).

Notice of Reasons for Refusal for Japanese Patent Application No. 526299/2013, dated Oct. 21, 2014 (English language translation included) (12 pages).

Decision of Refusal for Japanese Patent Application No. 526299/2013, dated Oct. 28, 2015, mailed Nov. 4, 2015 (12 pages; English language translation provided).

Supplementary European Search Report for European Patent Application No. 11820990.7, dated Feb. 3, 2014 (5 pages).

Communication pursuant to Article 94(3) EPC for European Patent Application No. 11820990.7, dated Mar. 3, 2016 (4 pages).

Non-Final Office Action for U.S. Appl. No. 13/818,367, dated Feb. 12, 2014 (15 pages).

Final Office Action for U.S. Appl. No. 13/818,367, dated Nov. 6, 2014 (11 pages).

Advisory Action for U.S. Appl. No. 13/818,367, dated Feb. 26, 2015 (3 pages).

Non-Final Office Action for U.S. Appl. No. 13/818,367, ated Nov. 19, 2015 (12 pages).

Final Office Action for U.S. Appl. No. 13/818,367, dated Jun. 3, 2016 (14 pages).

Notice of Allowance for U.S. Appl. No. 13/818,367, dated Apr. 11, 2017 (10 pages).

* cited by examiner

QUINAZOLINE DERIVATIVES SUBSTITUTED BY ANILINE, PREPARATION METHOD AND USE THEREOF

This application is a continuation-in-part of U.S. patent application Ser. No. 13/818,367, filed Apr. 1, 2013, which is the U.S. National Stage of PCT/CN2011/001466, filed Aug. 30, 2011.

TECHNICAL FIELD

The present invention belongs to the field of pharmaceutical technology, more specifically relates to a quinazoline derivative substituted by aniline, a pharmaceutically acceptable salt thereof and a stereoisomer thereof, a preparation method thereof, a pharmaceutical composition containing said compound and a pharmaceutical formulation containing said compound, a use of said compound in treating a hyperplasia disease and a chronic obstructive pulmonary disease, and a use of said compound in the manufacture of a medicant for treating a hyperplasia disease and a chronic obstructive pulmonary disease.

BACKGROUND ART

The protein tyrosine kinase is an enzyme that catalytically transfers the phosphate group from ATP to the tyrosine residue located at the protein substrate, and has a play in the normal cell growth. Many growth factor receptor proteins operate via the tyrosine kinase, and influence the conduction of signal passage and further regulate the cell growth by this process. However, in some circumstances, these receptors become abnormally due to either the mutation or the overexpression, which cause the uncontrolled cell multiplication, cause the tumor growth, and finally initiate the well-known disease, i.e., cancer. The growth factor receptor protein tyrosine kinase inhibitor, via the inhibition of the above phosphorylation process, may treat cancers and other diseases characterized by the uncontrolled or abnormal cell growth.

An epidermal growth factor receptor (EGFR) is a multi-function glycoprotein that is widely distributed on the cell membranes of the tissues of the human body, and is an oncogene analog of avian erythroblastic leukemia viral (v-erb-b). Human EGFR/HER1/ErbB-1 and HER2 (human epidermal growth factor receptor-2)/ErbB-2/Teu/p185, HER3/ErbB-3, HER4/ErbB-4 and the like are grouped into the HER/ErbB family, and belong to protein tyrosine kinases (PTKs). It is indicated in the clinical study that EGFR and the like are expressed in the epithelia-derived tumors such as squamous cell carcinoma of head and neck, mammary cancer, rectal cancer, ovarian cancer, prostate carcinoma, non-small cell lung cancer, and the like. Pan-HER tyrosine kinase inhibitor, via the competitive binding the kinase catalytic sites in the intracellular region against ATP, blocks the autophosphorylation of intramolecular tyrosine, blocks the tyrosine kinase activation, inhibits HER family activation, and therefore inhibits cell cycle progression, accelerates cell apoptosis, and exerts the therapeutic action.

EGFR, after binding the ligand, forms a dimer with a subgroup of HER family, and then combines with ATP to activate the tyrosine kinase activity of the EGFR itself. Therefore, the autophosphorylation occurs in several tyrosine sites of the intracellular kinase region. Pan-HER tyrosine kinase inhibitor, via simultaneity acting on EGFR, and HER2/4, inhibits the activation of HER family, and play a good role in the tumor growth inhibition.

It is indicated in the study that Pan-HER tyrosine kinase irreversible inhibitor has an inhibition effect on HER2/4, besides it effectively inhibits EGFR. The pharmaceutical drugs of this kind, having an irreversible inhibition to both of HER/ErbB families, not only increase the drug activity, but also reduce the drug resistance, and have a substantial inhibition effect on H1975 cell lines which are resistant to erlotinib.

The pharmaceutical drugs that are now commercially available include selective EGFR tyrosine kinase inhibitor gefitinb (Iressa, ZD1839), erlotinib (Tarceva, OSI-774) and double EGFR/HER2 inhibitor Lapatinib (Tykerb, GW572016), and their structures are shown below. These three drugs are all reversible EGF receptor tyrosine phosphorylation kinase inhibitor. It is found in the study that they have good therapeutic response to some tumors initially. However, several months after the treatment, the disease progression appears again and therefore a natural or secondary drug resistance forms.

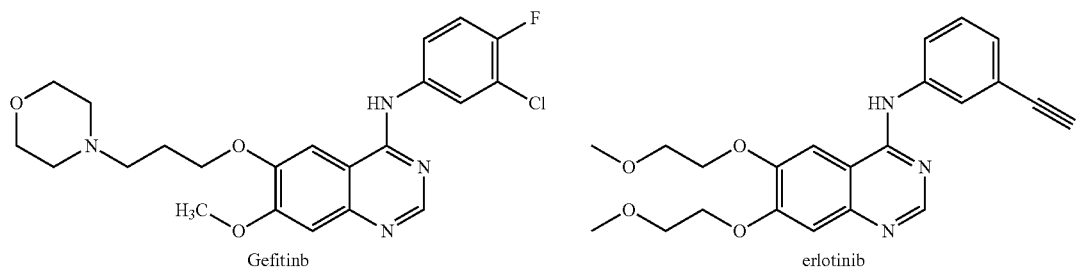

Gefitinb      erlotinib

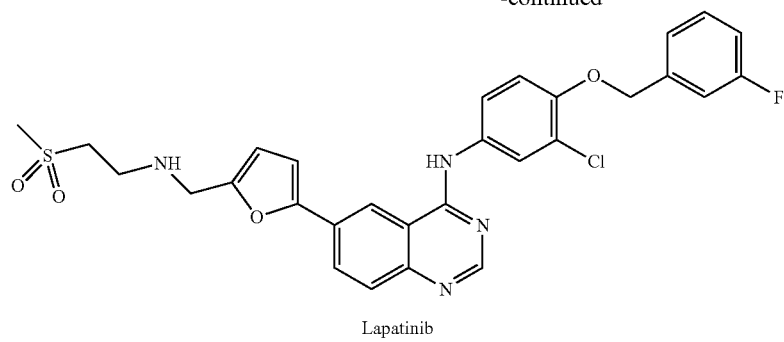

Lapatinib

It is reported in the literature (Bioorganic & Medicinal Chemistry (2008) 16 page 3482-3488) that the commercially available drugs such as gefitinb and erlotinib have been widely used clinically. The long-term treatment of the late NSCLC (non-small cell lung cancer) may create an acquired drug-resistance, which has a negative effect on the therapeutical effect.

It is believed that the reversible EFG receptor tyrosine kinase inhibitor competes with ATP for the combination with EFG receptor tyrosine kinase. Due to the relative high concentration of the intracellular ATP (in order of mM), the reversible EGF receptor tyrosine kinase inhibitor, which shows a high activity in an in-vitro assay, is difficult to show the effect in the animal pathologic model. The irreversible EGF receptor tyrosine kinase inhibitor does not compete with ATP, and therefore it is expected that the non-reversible EGF receptor tyrosine kinase inhibitor may have a better in-vivo activity.

WO97/38983 discloses irreversible EGF receptor tyrosine kinase inhibitors. For these inhibitors, one Michael receptor is introduced at 6-position of quinazoline, and therefore a Michael addition reaction can be conducted between this receptor and —SH of the cysteine on the pouch wall of the EGF receptor tyrosine kinase activity center (Cys773). Moreover, the activities of these inhibitors and the complexity of the Michael addition reaction between these inhibitors and —SH of the cysteine are in a positive structure-function correlation.

DE10042061 A1 discloses a 4-phenylaminequinazoline derivative which has a lactone structure at 7-position of quinazoline. It is believed that it has an inhibition activity for the signal transduction mediated by the tyrosine kinase.

It is reported in the reference (Adv Ther (2011) 28(2) p. 1-8) that PF-299 (Pfizer) and Afatinib (BIBW2992) (Boehringer Ingelheim) are in the clinical stage III, and Neratinib (HKI292) is in the clinical stage II. It is believed that these compounds are irreversible tyrosine kinase inhibitor, and can solve the EGFR resistance.

It is reported in the reference (IDrugs (2004) 7(1) p. 58-63) that Canertinib (CI-1033) is in the clinical stage II, and has an activity for some types of tumore, and has no toxicity in the experimental model. Canertinib (CI-1033) has a structure of:

(CI-1033)

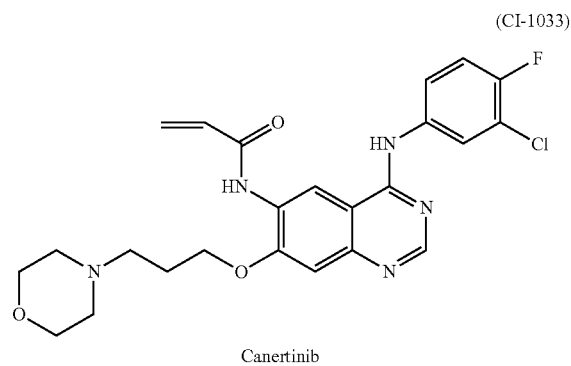

Canertinib

Upon developing the drug having a good antineoplastic effect, being able to reduce the drug resistance and having a good tolerance, the present inventors discover a quinazoline derivative having a Pan-HER irreversible inhibition function.

SUMMARY OF THE INVENTION

Therefore, the present invention provides a compound represented by a general formula (I), a pharmaceutically acceptable salt thereof and a stereoisomer thereof:

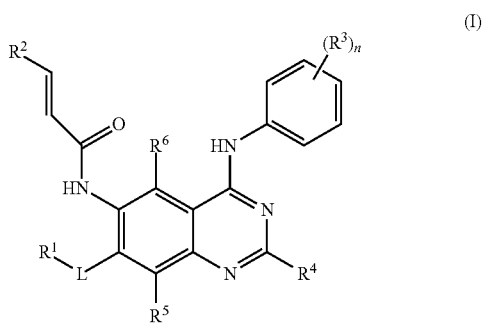

(I)

wherein, $R^1$ is selected from the group consisting of the following groups that are unsubstituted or substituted by 1-2 $Q_1$ substituents: a 6-10-membered fused ring-$C_{0-6}$alkyl group, a 7-10-membered spiro ring-$C_{0-6}$alkyl group or a 7-10-membered bridged ring-$C_{0-6}$alkyl group, wherein 1-3 carbon atoms of said fused ring, spiro ring or bridged ring can be replaced with 1-3 hetero atoms and/or groups that can be identical or different and are selected from the group consisting of O, $S(O)_m$, $N(H)_m$, $NCH_3$ and $C(O)$, provided that after the replacement, O and $C(O)$ in the ring are not adjacent to each other, $Q_1$ is selected from the group consisting of halogen, hydroxyl, amino, carboxyl, cyano, a $C_{1-6}$alkyl group, a $C_{1-6}$alkoxyl group, a $C_{1-6}$alkylamino group, a di($C_{1-6}$alkyl)amino group, a $C_{1-6}$alkylcarbonyloxy group, a $C_{1-6}$alkylacylamino group, a $C_{1-6}$alkylsulfonyl group, a $C_{1-6}$alkylsulfinyl group, a $C_{1-6}$alkylsulfonylamino group and a $C_{3-8}$cycloalkyl group;

$R^2$ is selected from the group consisting of hydrogen, a $C_{1-6}$alkyl group or a $C_{1-6}$alkoxyl group that is unsubstituted or substituted by 1-2 $Q_2$ substituents, a formyl group that is substituted by a $Q_2$ substituent or $N(H)_m$, $Q_2$ is selected from the group consisting of halogen, hydroxyl, amino, carboxyl, cyano, a $C_{1-6}$alkyl group, a $C_{1-6}$alkoxyl group, a $C_{1-6}$alkylamino group, a di($C_{1-6}$alkyl)amino group, a $C_{1-6}$alkylcarbonyloxy group, a $C_{1-6}$alkylacylamino group, a $C_{1-6}$alkylsulfonyl group, a $C_{1-6}$alkylsulfinyl group, a $C_{1-6}$alkylsulfonylamino group, a $C_{3-8}$cycloalkyl group, an unsaturated $C_{5-7}$ cyclic hydrocarbyl and a saturated or unsaturated 3-8-membered heterocyclyl, wherein the $C_{3-8}$cycloalkyl, the unsaturated $C_{5-7}$ cyclic hydrocarbyl and the saturated or unsaturated 3-8-membered heterocyclyl can further substituted by 1-2 $Q_3$ substituents, $Q_3$ is selected from the group consisting of halogen, hydroxyl, amino, carboxyl, cyano, a $C_{1-6}$alkyl group, a $C_{1-6}$alkoxyl group, a $C_{1-6}$alkylamino group, a di($C_{1-6}$alkyl)amino group, a $C_{1-6}$alkylcarbonyloxy group, a $C_{1-6}$alkylacylamino group, a $C_{1-6}$alkylsulfonyl group, a $C_{1-6}$alkylsulfinyl group, a $C_{1-6}$alkylsulfonylamino group and a halogen-substituted $C_{1-6}$alkoxy group;

$R^3$ is selected from the group consisting of hydrogen, halogen, hydroxyl, cyano, nitro, a $C_{1-6}$alkyl group, a $C_{1-6}$alkoxyl group, a $C_{1-6}$alkyl group or a $C_{1-6}$alkoxyl group that is substituted by halogen, a $C_{1-6}$alkylcarbonyloxy group, a $C_{1-6}$alkylacylamino group, a $C_{1-6}$alkylsulfonyl group, a $C_{1-6}$alkylsulfinyl group or a $C_{1-6}$alkylsulfonylamino group;

$R^4$, $R^5$ and $R^6$ are each independently selected from the group consisting of hydrogen, halogen, a $C_{1-6}$alkyl group, a $C_{1-6}$alkoxyl group, a $C_{1-6}$alkyl group or a $C_{1-6}$alkoxyl group that is substituted by halogen, a $C_{1-6}$alkylamino group or a di($C_{1-6}$alkyl)amino group;

L is selected from the group consisting of a covalent bond, O, $S(O)_m$, $N(H)_m$, $NCH_3$ or $C(O)$;

n is 1, 2 or 3; and m is 0, 1 or 2.

The present invention also provides a pharmaceutical composition containing a compound represented by the general formula (I), a pharmaceutically acceptable salt thereof or a stereoisomer thereof.

The present invention also provides a pharmaceutical formulation containing a compound represented by the general formula (I), a pharmaceutically acceptable salt thereof or a stereoisomer thereof and a pharmaceutically acceptable carrier.

The present invention also provides a compound represented by the general formula (I), a pharmaceutically acceptable salt thereof or a stereoisomer thereof, or a pharmaceutical composition containing a compound represented by the general formula (I), a pharmaceutically acceptable salt thereof or a stereoisomer thereof as a medicament for treating a hyperplasia disease and a chronic obstructive pulmonary disease.

The present invention also provides a use of a compound represented by the general formula (I), a pharmaceutically acceptable salt thereof or a stereoisomer thereof, or a pharmaceutical composition containing a compound represented by the general formula (I), a pharmaceutically acceptable salt thereof or a stereoisomer thereof for the manufacture of a medicament for treating a hyperplasia disease and a chronic obstructive pulmonary disease.

The present invention also provides a method for treating a hyperplasia disease and a chronic obstructive pulmonary disease, which comprises administering to a subject in need thereof an effective amount of a compound represented by the general formula (I), a pharmaceutically acceptable salt thereof or a stereoisomer thereof, or a pharmaceutical composition containing a compound represented by the general formula (I), a pharmaceutically acceptable salt thereof or a stereoisomer thereof.

The present invention also provides a process for preparing a compound of general formula (I), comprising the steps of:

Reaction Procedure:

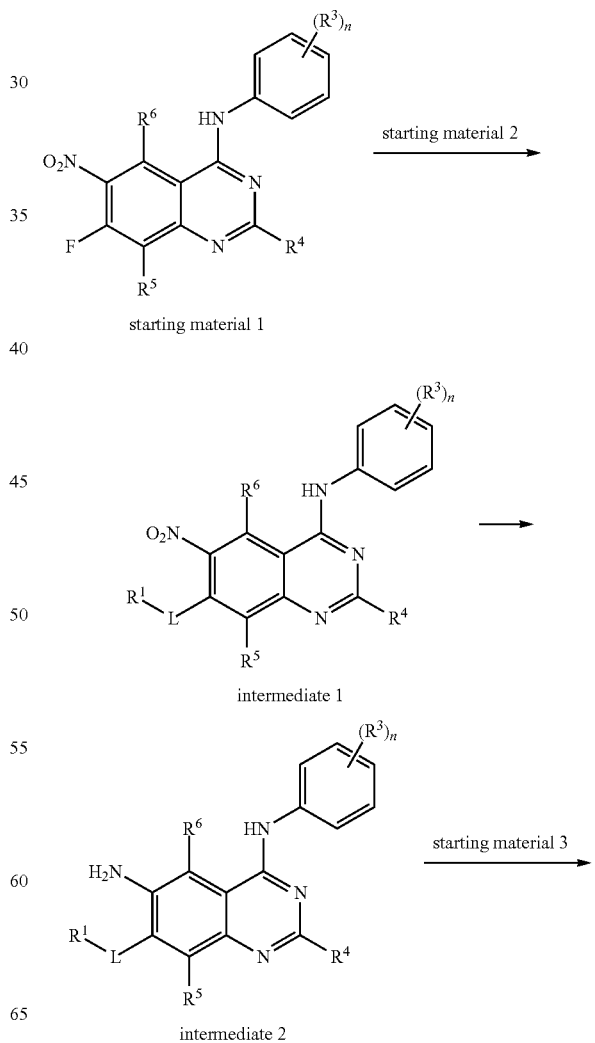

-continued

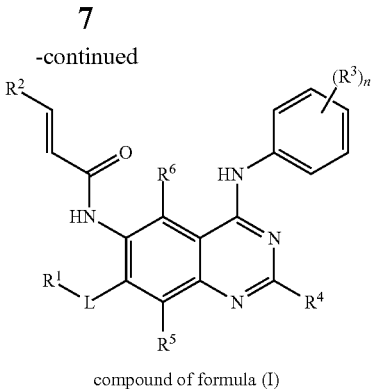

compound of formula (I)

wherein, $R^1$, $R^2$, $R^3$, $R^4$, $R^5$, $R^6$, L and n are as defined hereinbefore; the starting material 1 is synthesized according to the methodology provided in US 2005/0250761 A1, the starting material 2=$R^1$-LH; the starting material 3=$R^2$CH=CH—C(O)Cl or $R^2$CH=CH—COOH, (1) Dissolving the starting material 2 in a non-protonic polar organic solvent, and reacting with the starting material 1 in the presence of a base to produce the Intermediate 1;
(2) Reacting the Intermediate 1 with a reducing agent optionally in the presence of an acid to produce the Intermediate 2; and
(3) Dissolving the Intermediate 2 in an organic solvent, and reacting with the starting material 3 in the presence of an organic base to produce the compound of formula (I).

As used herein, the term "halo" refers to fluoro, chloro, bromo or iodo.

As used herein, the term "$C_{1-6}$alkyl" refers to a straight or branched alkyl containing 1-6 carbon atoms; and its example includes but is not limited to methyl, ethyl, n-propyl, iso-propyl, n-butyl, iso-butyl, sec-butyl, tert-butyl, n-pentyl, iso-pentyl, 2-methylbutyl, neo-pentyl, 1-ethylpropyl, n-hexyl, iso-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1-methyl-2-methylpropyl and the like.

As used herein, the term "$C_{1-6}$alkoxy" refers to a "$C_{1-6}$alkyl-O—" group, wherein the $C_{1-6}$alkyl is defined as hereinbefore; and its example includes but is not limited to methoxy, ethoxy, propoxy, isopropoxy, butoxy, isobutoxy, tert-butoxy, sec-butoxy, pentoxy, neo-pentoxy, hexyloxy and the like.

As used herein, the term "$C_{3-8}$cycloalkyl" refers to a monocyclic saturated carbocyclic group containing 3-8, e.g. 3, 4, 5, 6, 7 or 8, preferably 3-6, e.g. 3-5 carbon atoms; and its example includes but is not limited to cyclopropyl, cyclobutyl, 1-methylcyclobutyl, cyclopentyl, cyclohexyl, cycloheptyl, cyclooctyl and the like.

As used herein, the term "$C_{1-6}$alkylamino" refers to a "$C_{1-6}$alkyl-NH—" group, wherein the $C_{1-6}$alkyl is defined as hereinbefore; and its example includes but is not limited to methylamino, ethylamino, propylamino, isopropylamino, butylamino, isobutylamino, tert-butylamino, sec-butylamino, pentylamino, neo-pentylamino, hexylamino and the like.

As used herein, the term "di($C_{1-6}$alkyl)amino" refers to a "($C_{1-6}$alkyl)$_2$-N—" group, wherein the two $C_{1-6}$alkyl can be identical or different and are respectively defined as hereinbefore; and its example includes but is not limited to dimethylamino, diethylamino, dipropylamino, dibutylamino and the like.

As used herein, the term "$C_{1-6}$alkylcarbonyloxy", "$C_{1-6}$alkylacylamino", "$C_{1-6}$alkylsulfonyl", "$C_{1-6}$alkylsulfonylamino" and "$C_{1-6}$alkylsulfinyl" respectively refer to "$C_{1-6}$ alkyl-C(O)O—", "$C_{1-6}$alkyl-C(O)NH—", "$C_{1-6}$alkyl-SO$_2$—", "$C_{1-6}$alkyl-SO$_2$NH—" and "$C_{1-6}$alkyl-SO—" groups, wherein the $C_{1-6}$alkyl is defined as hereinbefore.

As used herein, the term "6-10-membered fused ring" refers to a saturated or unsaturated fused ring system containing 6-10 carbon atoms and formed by the linking of at least two cyclic structures sharing two adjacent atoms with each other, wherein the cyclocarbon atom(s) can be replaced with 1-3 hetero atoms and/or groups that can be identical or different and are selected from the group consisting of O, S(O)$_m$, N(H)$_m$, NCH$_3$ and C(O), provided that after the replacement, O and C(O) in the ring are not adjacent to each other. Its example includes but is not limited to 5,6-dihydroimidazo[1.2-a]pyrazin-7(8H)-yl, 5,6-dihydro-1,7-naphthyridin-7(8H)-yl, 5H-pyrrolo[3.4-b]pyridin-6(7H)-yl, 7,8-dihydropyridino[4.3-d]pyrimidin-6(5H)-yl, 2,3,6,7-tetrahydro-1H-pyrazolo[4.3-c]pyridin-5(4H)-yl, 6,7-dihydrothiazolo[5.4-c]pyridin-5 (4H)-yl, 3-methyl-6,7-dihydro-3H-pyrazolo[4.5-c]pyridin-5 (4H)-yl, 2-methylhexahydrocyclopenta[c]pyrrol-5-yl and the like.

As used herein, the term "7-10-membered spiro ring" refers to a saturated or unsaturated fused ring system containing 7-10 carbon atoms and formed by at least two rings sharing the same atom, wherein the cyclocarbon atom(s) can be replaced with 1-3 hetero atoms and/or groups that can be identical or different and are selected from the group consisting of O, S(O)$_m$, N(H)$_m$, NCH$_3$ and C(O), provided that after the replacement, O and C(O) in the ring are not adjacent to each other. Its example includes but is not limited to 6-azaspiro[2.5]octan-6-yl, 7-azaspiro[3.5]nonan-7-yl, 8-azaspiro[4.5]decan-8-yl, 1-methyl-1,7-diazaspiro[4.4]nonan-7-yl, 2-methyl-2,6-diazaspiro[3.4]octan-6-yl, 6-azaspiro[3.4]octan-6-yl, 2-oxa-7-azaspiro[4.5]decan-7-yl, 2-oxa-8-azaspiro[4.5]decan-8-yl, 2-methyl-2,7-diazaspiro[4.5]decane and the like.

As used herein, the term "7-10-membered bridged ring" refers to a saturated or unsaturated fused ring system containing 7-10 carbon atoms and formed by any two rings sharing two atoms not directly linked, wherein the cyclocarbon atom(s) can be replaced with 1-3 hetero atoms and/or groups that can be identical or different and are selected from the group consisting of O, S(O)$_m$, N(H)$_m$, NCH$_3$ and C(O), provided that after the replacement, O and C(O) in the ring are not adjacent to each other. Its example includes but is not limited to (1S,4S)-2-methyl-2-azabicyclo[2.2.1]hexane, 2-azabicyclo[2.2.1]heptane, 8-methylbicyclo[3.2.1]octane, 3-oxa-8-azabicyclo[3.2.1]octane, 2-azabicyclo[2.2.2]octane, 7-azabicyclo[2.2.1]heptane, 3-azabicyclo[3.2.1]octane, 3-azabicyclo[3.3.2]decane, 7-oxabicyclo[2.2.1]heptane, 8-oxabicyclo[3.2.1]octane and the like.

As used herein, the term "unsaturated $C_{5-7}$ cyclic hydrocarbyl" refers to a monocyclic unsaturated carbocyclic group containing 5-7, e.g. 5, 6, or 7 carbon atoms. Its example includes but is not limited to cyclopentenyl, cyclohexenyl, cyclohexadienyl, cycloheptenyl, cycloheptadienyl, cycloheptatrienyl and the like.

As used herein, the term "3-8 membered heterocyclyl" refers to a cyclic system consisted of 3-8, e.g. 3, 4, 5, 6, 7 or 8, preferably 5-8 carbon atoms and heteroatoms selected from the group consisting of nitrogen, oxygen and sulfur, and its example includes but is not limited to the groups formed by the following rings: aziridine, 2H-aziridine, diaziridine, 3H-diazirine, azetidine, 1,2-diazetidine, azete, 3,4-dihydro-1,2-diazete, pyrrole, pyrroline, pyrrolidine, imidazole, 4,5-dihydro-imidazole, imidazolidine, pyrazole, 4,5-dihydro-pyrazole, pyrazolidine, 1,2,3-triazole, 1,2,4-triazole, tetrazole, pyridine, 2-pyridinone, 4-pyridinone, piperidine, pyridazine, pyrimidine, pyrazine, piperazine, 1,2,3-triazine, 1,2,4-triazine, 1,3,5-triazine, 1,2,4,5-tetrazine, azepine, 1,2-diazepine, 1,3-diazepine, 1,4-diazepine, azocine, 1,4-dihydro-1,4-diazocine, oxirane, dioxirane, thiirane, oxetane, 1,2-dioxetane, thietane, 1,2-dithiete, furan, tetrahydrofuran, thiene, 2,5-dihydrothiene, tetrahydrothiene, 1,3-dioxolane, 1,3-dioxol-2-one, 1,2-dithiole, 1,3-dithiolane, 2H-pyran, 2H-pyran-2-one, 3,4-dihydro-2H-pyran, 4H-pyran, tetrahydro pyran, 4H-pyran-4-one, 1,4-dioxine, 1,4-dithiine, 1,4-oxathiine, 1,4-dioxane, 1,3-dioxane, 1,3-oxathiane, oxepine, thiepine, 1,4-dioxocine, oxaziridine, oxazole, 4,5-dihydrooxazole, isoxazole, 4,5-dihydroisoxazole, 2,3-dihydroisoxazole, 1,2,3-oxadiazole, 1,2,5-oxadiazole, thiazole, 4,5-dihydrothiazole, isothiazole, 1,2,3-thiadiazole, 1,2,4-thiadiazole, 1,3,4-thiadiazole, 2H-1,2-oxazine, 4H-1,2-oxazine, 6H-1,2-oxazine, 2H-1,3-oxazine, 4H-1,3-oxazine, 5,6-dihydro-4H-1,3-oxazine, 6H-1,3-oxazine, 2H-1,4-oxazine, 4H-1,4-oxazine, 2H-1,3-thiazine, 4H-1,3-thiazine, 5,6-dihydro-4H-1,3-thiazine, 6H-1,3-thiazine, 2H-1,4-thiazine, 4H-1,4-thiazine, morpholine and the like.

The present compound of formula (I) can be used in its free form or the form of its pharmaceutically acceptable salt. The pharmaceutically acceptable salt of the formula (I) compound of the present invention comprises the salts formed at the site of the basic group such as amino and the salts formed at the site of the acidic group such as hydroxyl and carboxyl. The salt formed at the site of the basic group includes a salt that is formed with an inorganic acid, such as hydrochloride, hydrobromide, sulfate and the like; a salt that is formed with an organic carboxylic acid, such as tartrate, formate, acetate, lactate, citrate, trichloroacetate, trifluoroacetate and the like; a salt that is formed with sulfonic acid, such as mesylate, benzenesulfonate, para-tosylate, naphthalenesulfonate, and the like. The salt form at the site of the acidic group includes a salt that is formed with an alkali metal such as sodium, potassium and the like; a salt that is formed with an alkaline earth metal such as calcium, magnesium and the like; an ammonium salt; a salt that is formed with a nitrogen-containing organic base, said organic base includes, but is not limited to trimethylamine, triethylamine, tributylamine, pyridine N,N-dimethylphenylamine, N-methylpiperidine, N-methylmorpholine, diethylamide, dicyclohexyl amine, procaine, dibenzylamine, N-benzyl-β-phenylethylamine, 1-diphenylhydroxylmethylamine, N,N'-dibenzyl ethylene diamine and the like.

The present compound of formula (I) includes any mixture of all of possible optical isomers/diastereoisomers and pure or partially pure compounds. The present invention comprises all stereoisomeric forms of these compounds.

The present compound of formula (I) contains olefinic double bonds. Unless otherwise specified, the present invention includes its cis-isomer and its trans-isomer.

The present compound of formula (I) can be present in a form of tautomer. Each of tautomers and a mixture thereof are comprised in the scope of the present invention.

In one preferable embodiment of the present compound of the general formula (I),
$R^1$ is selected from the group consisting of the following groups that are unsubstituted or substituted by 1-2 $Q_1$ substituents: a 6-10-membered saturated fused ring-$C_{0-4}$ alkyl group, a 7-10-membered saturated spiro ring-$C_{0-4}$ alkyl group or a 7-10-membered saturated bridged ring-$C_{0-4}$ alkyl group, wherein 1-3 carbon atoms of said fused ring, spiro ring or bridged ring can be replaced with 1-3 hetero atoms and/or groups that can be identical or different and are selected from the group consisting of O, $S(O)_m$, $N(H)_m$, $NCH_3$ and $C(O)$, provided that after the replacement, O and $C(O)$ in the ring are not adjacent to each other, $Q_1$ is selected from the group consisting of halogen, hydroxyl, amino, carboxyl, cyano, a $C_{1-4}$alkyl group, a $C_{1-4}$alkoxyl group, a $C_{1-4}$alkylamino group, a di($C_{1-4}$alkyl) amino group, a $C_{1-4}$alkylcarbonyloxy group, a $C_{1-4}$alkylacylamino group, a $C_{1-4}$alkylsulfonyl group, a $C_{1-4}$alkylsulfinyl group, $C_{1-4}$alkylsulfonylamino and $C_{3-6}$cycloalkyl;

$R^2$ is selected from the group consisting of hydrogen, a $C_{1-4}$alkyl group or a $C_{1-4}$alkoxyl group that is unsubstituted or substituted by 1-2 $Q_2$ substituents, a formyl group that is substituted by a $Q_2$ substituent or $N(H)_m$, $Q_2$ is selected from the group consisting of halogen, hydroxyl, amino, cyano, a $C_{1-4}$alkyl group, a $C_{1-4}$alkoxyl group, a $C_{1-4}$alkylamino group, a di($C_{1-4}$alkyl)amino group, a $C_{1-4}$alkylcarbonyloxy group, a $C_{1-4}$alkylacylamino group, a $C_{1-4}$alkylsulfonyl group, a $C_{1-4}$alkylsulfinyl group, a $C_{1-4}$alkylsulfonylamino group, a $C_{3-6}$cycloalkyl group, an unsaturated $C_{5-7}$ cyclic hydrocarbyl and a saturated or unsaturated 5-8-membered heterocyclyl group, wherein the $C_{3-6}$cycloalkyl, the unsaturated $C_{5-7}$ cyclic hydrocarbyl and the saturated or unsaturated 5-8-membered heterocyclyl can be further substituted by 1-2 $Q_3$ substituents, $Q_3$ is selected from the group consisting of halogen, hydroxyl, amino, cyano, a $C_{1-4}$alkyl group, a $C_{1-4}$alkoxyl group, a $C_{1-4}$alkylamino group, a di($C_{1-4}$alkyl)amino group, a $C_{1-4}$alkylcarbonyloxy group, a $C_{1-4}$alkylacylamino group, a $C_{1-4}$alkylsulfonyl group, a $C_{1-4}$alkylsulfinyl group, a $C_{1-4}$alkylsulfonylamino group and a halogen-substituted $C_{1-4}$alkoxy group;

$R^3$ is selected from the group consisting of halogen, cyano, nitro, a $C_{1-4}$alkyl group, a $C_{1-4}$alkoxyl group, a $C_{1-4}$alkyl group or a $C_{1-4}$alkoxyl group that is substituted by halogen, a $C_{1-4}$alkylcarbonyloxy group, a $C_{1-4}$alkylacylamino group, a $C_{1-4}$alkylsulfonyl group, a $C_{1-4}$alkylsulfinyl group or a $C_{1-4}$alkylsulfonylamino group;

$R^4$, $R^5$ and $R^6$ are each independently selected from the group consisting of hydrogen, halogen, a $C_{1-4}$alkyl group, a $C_{1-4}$alkoxyl group, a $C_{1-4}$alkyl group or a $C_{1-4}$alkoxyl group that is substituted by halogen, a $C_{1-4}$alkylamino group or a di($C_{1-4}$alkyl)amino group; L is selected from the group consisting of a covalent bond, O, $S(O)_m$ or $N(H)_m$;
n is 1, 2 or 3; and
m is 0, 1 or 2.

In another preferable embodiment of the present compound of the general formula (I),
$R^1$ is selected from the group consisting of the following groups that are unsubstituted or substituted by 1-2 $Q_1$ substituents;

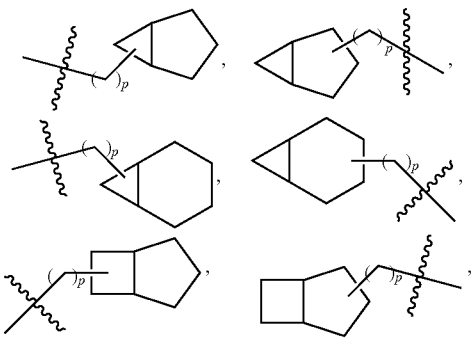

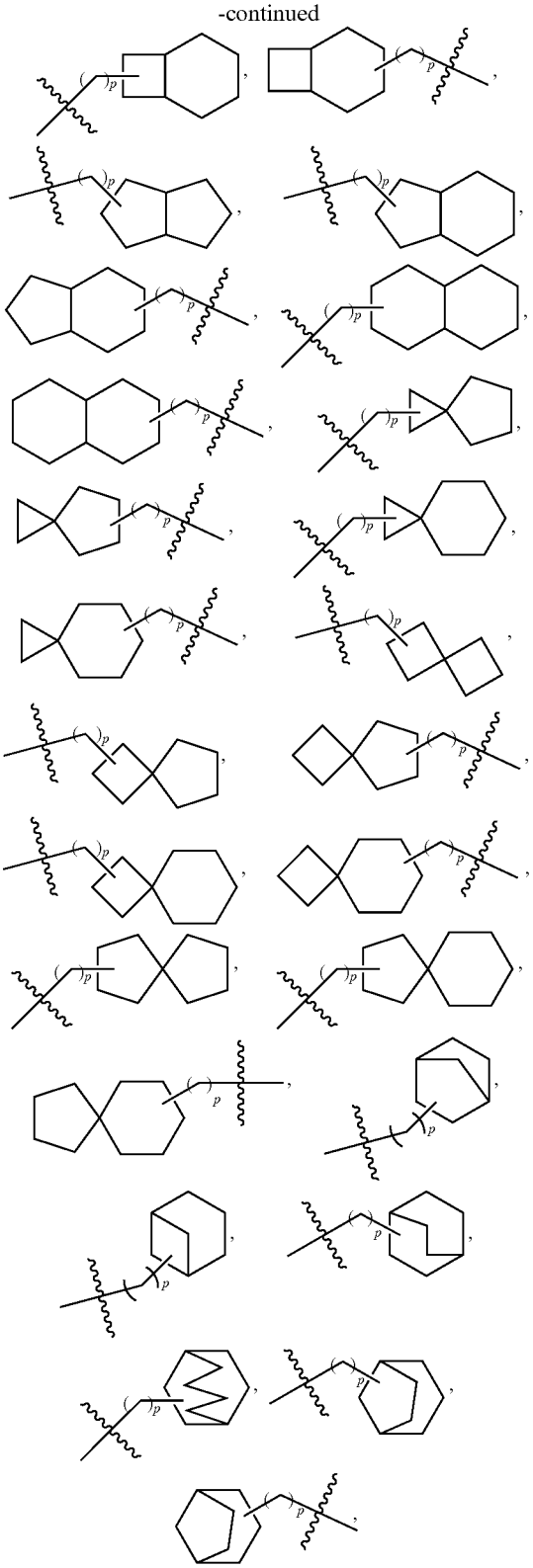

wherein 1-3 carbon atoms on the ring can be replaced with 1-3 hetero atoms and/or groups that can be identical or different and are selected from the group consisting of O, $S(O)_m$, $N(H)_m$, $NCH_3$ and $C(O)$, provided that after the replacement, O and $C(O)$ in the ring are not adjacent to each other, p is 0, 1 or 2, $Q_1$ is selected from the group consisting of halogen, hydroxyl, amino, carboxyl, a $C_{1-4}$alkyl group, a $C_{1-4}$alkoxyl group, a $C_{1-4}$alkylamino group, a di($C_{1-4}$alkyl)amino group and a $C_{3-6}$cycloalkyl group;

$R^2$ is selected from the group consisting of hydrogen, a $C_{1-4}$alkyl group that is unsubstituted or substituted by 1-2 $Q_2$ substituents, a formyl group that is substituted by a $Q_2$ substituent or $N(H)_m$, $Q_2$ is selected from the group consisting of halogen, hydroxyl, amino, a $C_{1-4}$alkyl group, a $C_{1-4}$alkoxyl group, a $C_{1-4}$alkylamino group, a di($C_{1-4}$alkyl)amino group, a $C_{1-4}$alkylcarbonyloxy group, a $C_{1-4}$alkylacylamino group, a $C_{1-4}$alkylsulfonyl group, a $C_{1-4}$alkylsulfonylamino group, a $C_{3-5}$cycloalkyl group and a saturated or unsaturated 5-8-membered heterocyclyl group, wherein the $C_{3-5}$cycloalkyl, the saturated or unsaturated 5-8-membered heterocyclyl can be substituted by 1-2 $Q_3$ substituents, $Q_3$ is selected from the group consisting of halogen, hydroxyl, amino, a $C_{1-4}$alkyl group, a $C_{1-4}$alkoxyl group, a $C_{1-4}$alkylamino group, a di($C_{1-4}$alkyl)amino group, a $C_{1-4}$alkylcarbonyloxy group, a $C_{1-4}$alkylacylamino group, a $C_{1-4}$alkylsulfonyl group, a $C_{1-4}$alkylsulfonylamino group and a halogen-substituted $C_{1-4}$alkoxy group;

$R^3$ is selected from the group consisting of fluoro, chloro, bromo, a $C_{1-4}$alkyl group or a $C_{1-4}$alkoxy group;

$R^4$, $R^5$ and $R^6$ are each independently selected from the group consisting of hydrogen, fluoro or chloro;

L is selected from the group consisting of a covalent bond, O, $S(O)_m$ or $N(H)_m$;

n is 1, 2 or 3; and m is 0, 1 or 2.

In another preferable embodiment of the present compound of the general formula (I), $R^1$ is selected from the group consisting of the following groups that are unsubstituted or substituted by 1-2 $Q_1$ substituents:

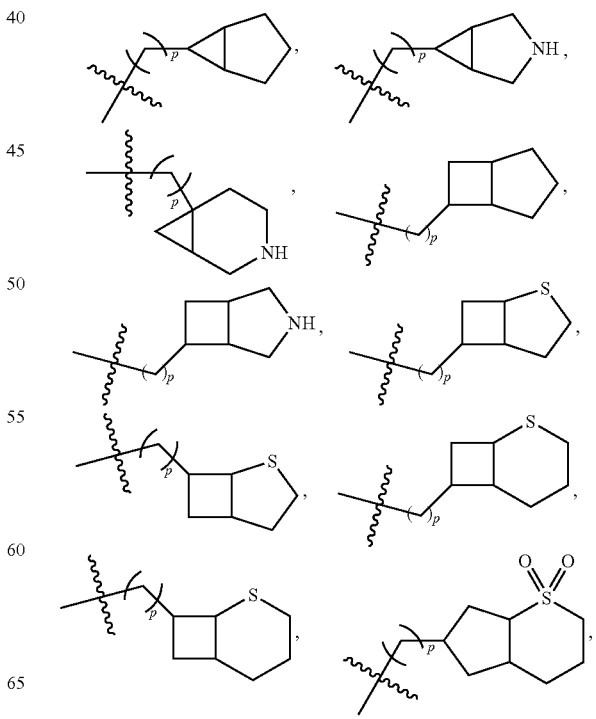

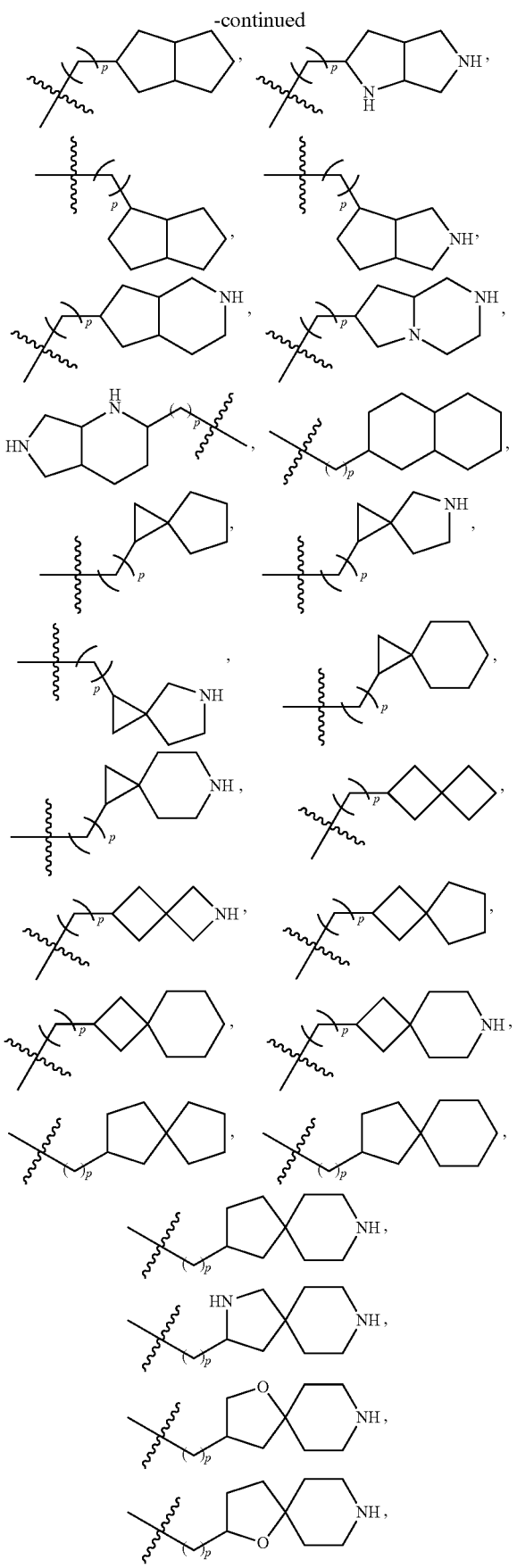
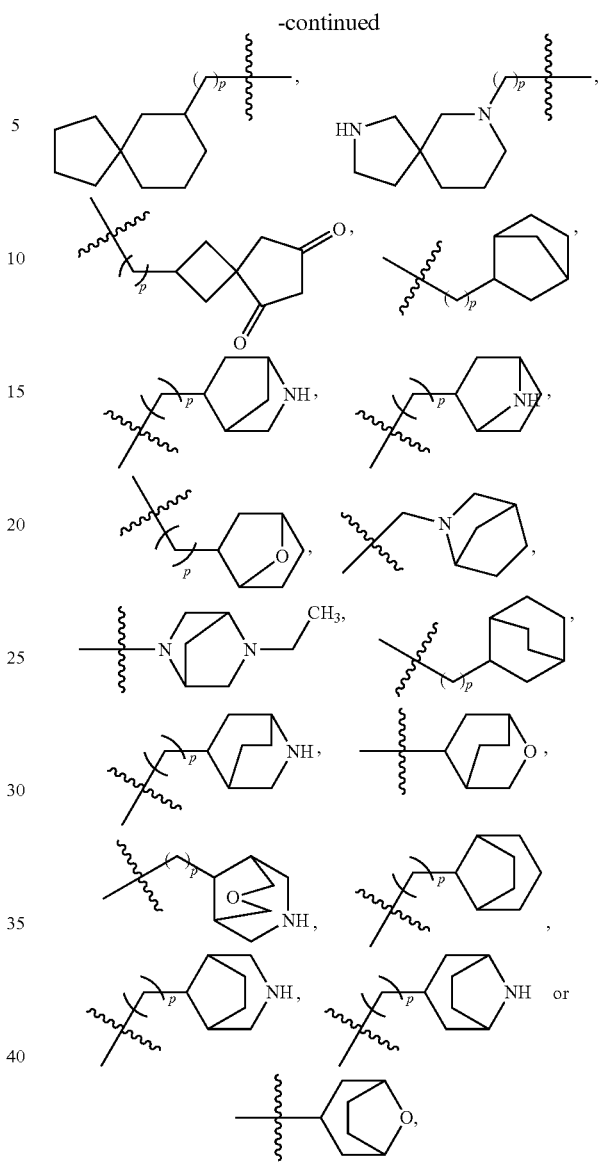

p is 0, 1 or 2, $Q_1$ is selected from the group consisting of halogen, amino, a $C_{1-4}$alkyl group, a $C_{1-4}$alkylamino group and a di($C_{1-4}$alkyl)amino group;

$R^2$ is selected from the group consisting of hydrogen, methyl that is unsubstituted or substituted by 1-2 $Q_2$ substituents or ethyl that is unsubstituted or substituted by 1-2 $Q_2$ substituents, a formyl group that is substituted by a $Q_2$ substituent or $N(H)_m$, $Q_2$ is selected from the group consisting of:

(1) halogen, hydroxyl, amino, a $C_{1-4}$alkoxyl group, a $C_{1-4}$alkylamino group, a di($C_{1-4}$alkyl)amino group, acetoxyl, acetamido, methylsulfonyl and methylsulfonylamino, (2) cyclopropyl, cyclopentyl, piperidinyl, piperazinyl, morpholinyl, pyrrolidinyl, furyl, thienyl, pyrrolyl, imidazolyl, thiazolyl, isothiazolyl, oxazolyl, pyridyl, pyrazinyl and pyrimidinyl, these $Q_2$ groups can be further substituted by 1-2 $Q_3$ substituents, $Q_3$ is selected from the group consisting of halogen, hydroxyl, amino, a $C_{1-4}$alkyl group, a $C_{1-4}$alkoxyl group, a $C_{1-4}$alkylamino group, a di($C_{1-4}$alkyl)amino group, a halogen-substituted $C_{1-4}$alkoxyl, acetoxyl, acetamido, methylsulfonyl and methylsulfonylamino;

$R^3$ is selected from the group consisting of fluoro or chloro;

$R^4$, $R^5$ and $R^6$ are hydrogen;

L is selected from the group consisting of a covalent bond or O;

n is 2; and m is 0, 1 or 2.

In another preferable embodiment of the present compound of the general formula (I), $R^1$ is selected from the group consisting of:

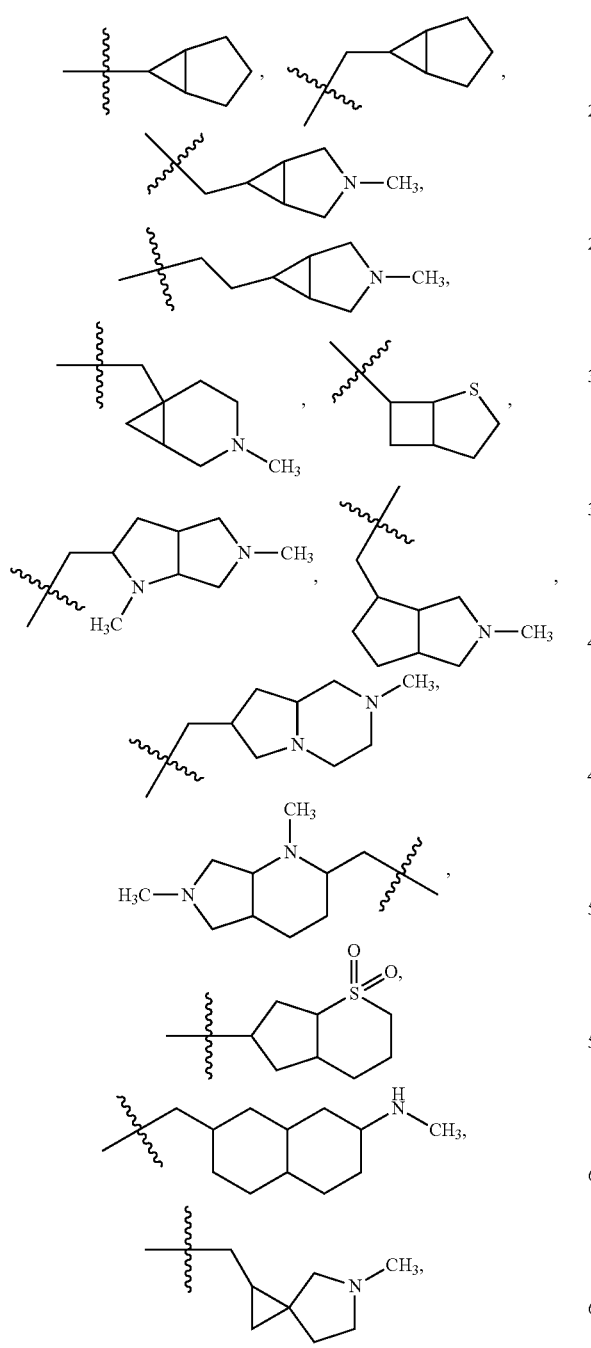

-continued

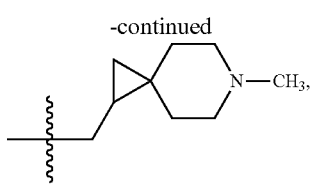
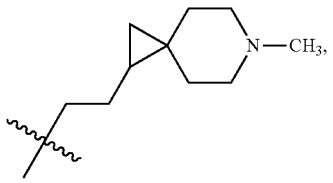
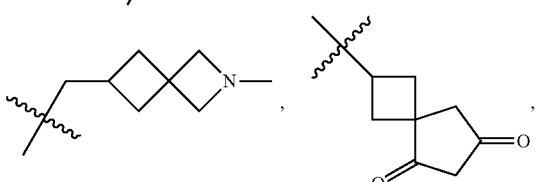
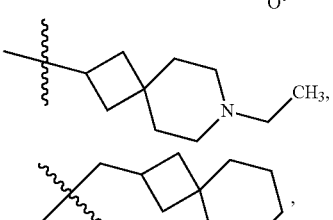
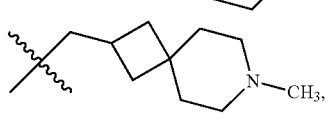
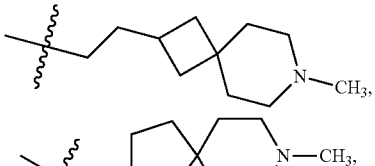
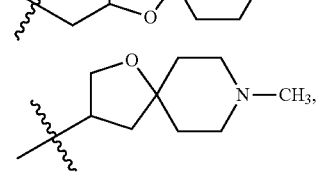
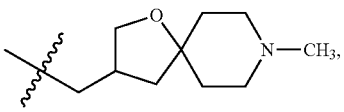
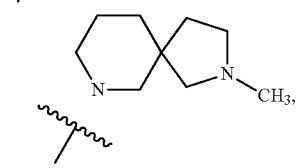
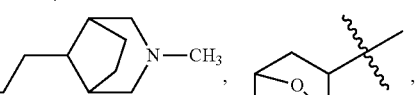
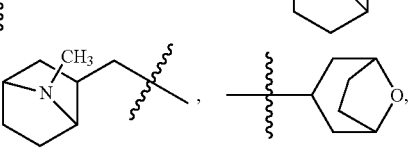

-continued

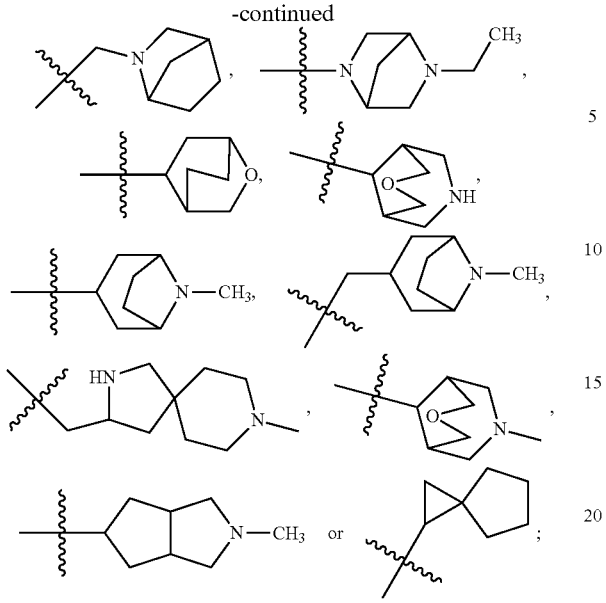

R² is selected from the group consisting of hydrogen, methyl that is unsubstituted or substituted by 1-2 Q₂ substituents or ethyl that is unsubstituted or substituted by 1-2 Q₂ substituents, Q₂ is selected from the group consisting of:

(1) methoxy and a di($C_{1-4}$alkyl)amino group, (2) piperidinyl, piperazinyl, morpholinyl, pyrrolidinyl, furyl, cyclopropyl, cyclopentyl, pyrrolyl, pyridyl, pyrimidinyl and thiazolyl, these Q₂ groups can be further substituted by 1-2 Q₃ substituents, Q₃ is selected from the group consisting of halogen, hydroxy, amino, a $C_{1-4}$alkyl group, a $C_{1-4}$alkoxyl group, a $C_{1-4}$alkylamino group, a di($C_{1-4}$alkyl)amino group and a halogen-substituted $C_{1-4}$alkoxy group;

R³ is selected from the group consisting of fluoro or chloro;

R⁴, R⁵ and R⁶ are hydrogen;

L is selected from the group consisting of a covalent bond or O; and n is 2.

In another preferable embodiment of the present compound of the general formula (I), R¹ is selected from the group consisting of:

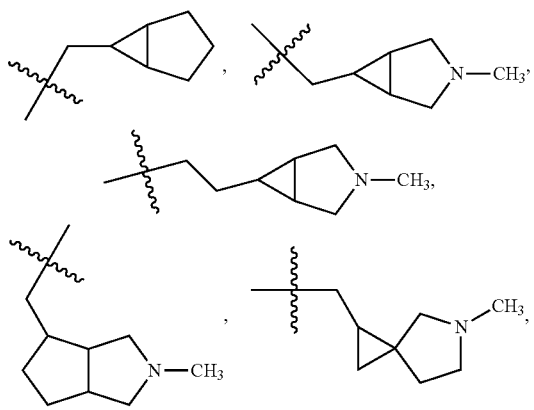

-continued

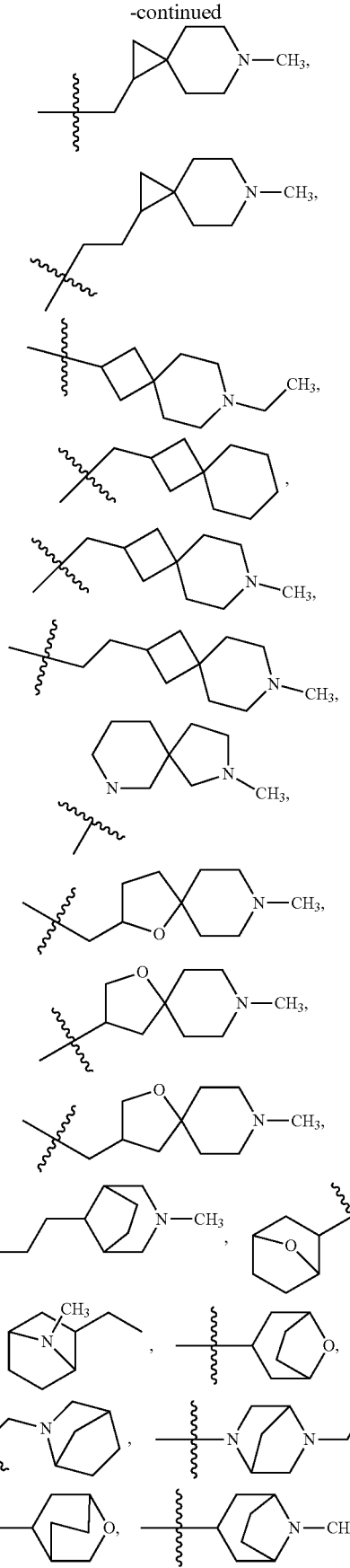

-continued

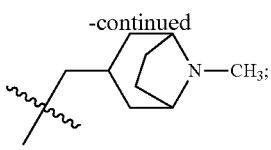

$R^2$ is selected from the group consisting of hydrogen, methyl that is unsubstituted or substituted by 1-2 $Q_2$ substituents or ethyl that is unsubstituted or substituted by 1-2 $Q_2$ substituents, $Q_2$ is selected from the group consisting of methoxy, dimethylamino, diethylamino, piperidinyl, piperazinyl and morpholinyl;
$R^3$ is selected from the group consisting of fluoro or chloro;
$R^4$, $R^5$ and $R^6$ are hydrogen;
L is selected from the group consisting of a covalent bond or O; and
n is 2.

The particularly preferable compound according to the present invention includes the following compounds and their pharmaceutically acceptable salts and stereoisomers:

| Compound | Name | Structure |
|---|---|---|
| 1 | (E)-N-[7-(8-oxabicyclo[3.2.1]octan-3-yloxy)-4-(3-chloro-4-fluorophenylamino)quinazolin-6-yl]-4-(piperidin-1-yl)-2-butenamide | 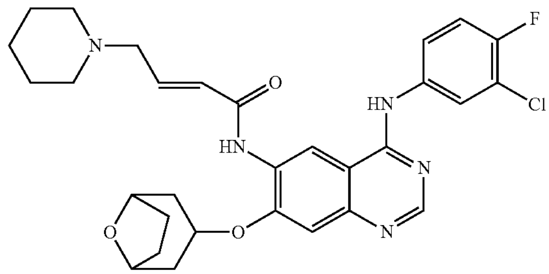 [SMILES: O=C(/C=C/CN1CCCCC1)Nc1cc2c(Nc3ccc(F)c(Cl)c3)ncnc2cc1OC1CC2CCC(C1)O2] |
| 2 | (E)-N-[7-(7-oxabicyclo[2.2.1]heptan-2-yloxy)-4-(3-chloro-4-fluorophenylamino)quinazolin-6-yl]-4-(piperidin-1-yl)-2-butenamide | 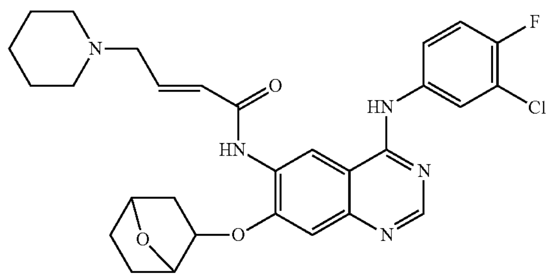 [SMILES: O=C(/C=C/CN1CCCCC1)Nc1cc2c(Nc3ccc(F)c(Cl)c3)ncnc2cc1OC1CC2CCC1O2] |
| 3 | (E)-N-[4-(3-chloro-4-fluorophenylamino)-7-(2-methyl-2,7-diazaspiro[4.5]decan-7-yl)quinazolin-6-yl]-4-(piperidin-1-yl)-2-butenamide | 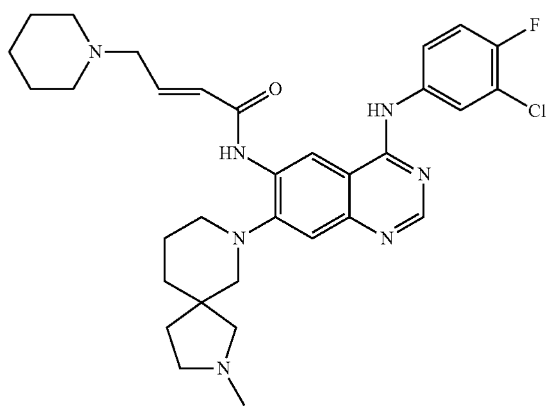 [SMILES: CN1CCC2(CCCN(c3cc4ncnc(Nc5ccc(F)c(Cl)c5)c4cc3NC(=O)/C=C/CN3CCCCC3)C2)C1] |
| 4 | N-[4-(3-chloro-4-fluorophenylamino)-7-(8-methyl-8-azabicyclo[3.2.1]octan-3-yloxy)quinazolin-6-yl]-acrylamide | 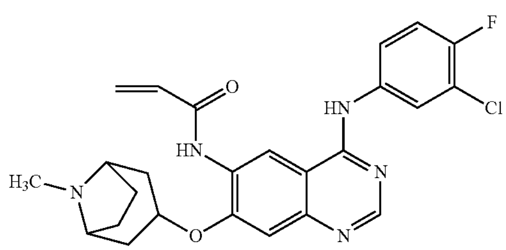 [SMILES: C=CC(=O)Nc1cc2c(Nc3ccc(F)c(Cl)c3)ncnc2cc1OC1CC2CCC(C1)N2C] |

-continued

| Compound | Name | Structure |
|---|---|---|
| 5 | N-[4-(3-chloro-4-fluorophenyl-amino)-7-(8-methyl-1-oxa-8-azaspiro[4.5]decan-3-yloxy)quinazolin-6-yl]-acrylamide | 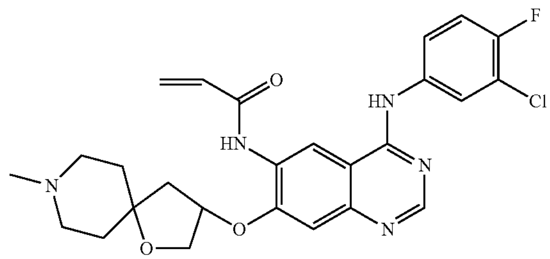 [SMILES: C=CC(=O)Nc1cc2c(Nc3ccc(F)c(Cl)c3)ncnc2cc1OC1COC2(CCN(C)CC2)C1] |
| 6 | N-[4-(3-chloro-4-fluorophenyl-amino)-7-((8-methyl-1-oxa-8-azaspiro[4.5]decan-3-yl)methoxy)quinazolin-6-yl]-acrylamide | 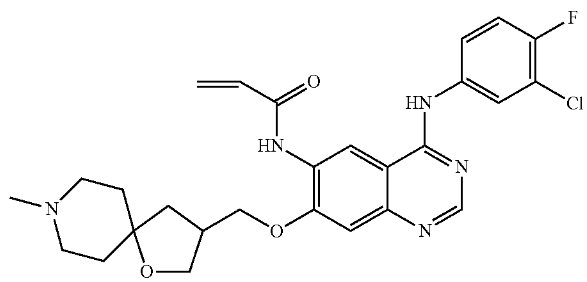 [SMILES: C=CC(=O)Nc1cc2c(Nc3ccc(F)c(Cl)c3)ncnc2cc1OCC1COC2(CCN(C)CC2)C1] |
| 7 | N-[4-(3-chloro-4-fluorophenyl-amino)-7-(8-methyl-1-oxa-8-azaspiro[4.5]decan-2-ylmethoxy)quinazolin-6-yl]acrylamide | 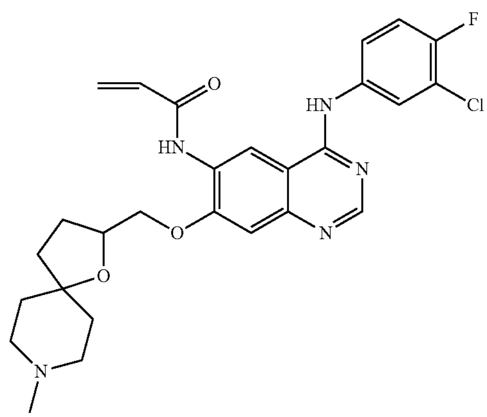 [SMILES: C=CC(=O)Nc1cc2c(Nc3ccc(F)c(Cl)c3)ncnc2cc1OCC1CCC2(CCN(C)CC2)O1] |
| 8 | N-[4-(3-chloro-4-fluorophenyl-amino)-7-(2-((1R,5S,6S)-3-methyl-3-azabicyclo[3.1.0]hexan-6-ylethoxy)quinazolin-6-yl]-acrylamide | 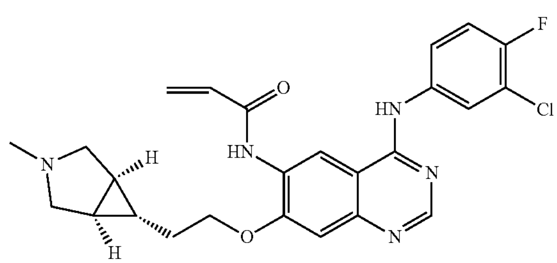 [SMILES: C=CC(=O)Nc1cc2c(Nc3ccc(F)c(Cl)c3)ncnc2cc1OCC[C@@H]1[C@H]2CN(C)C[C@@H]12] |
| 9 | N-[4-(3-chloro-4-fluorophenyl-amino)-7-((2-methyloctahydrocyclopenta[c]pyrrol-4-yl)methoxy)quinazolin-6-yl]-acrylamide | 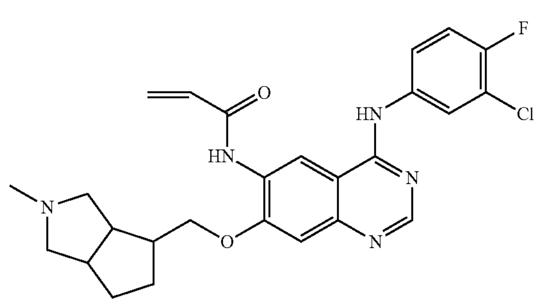 [SMILES: C=CC(=O)Nc1cc2c(Nc3ccc(F)c(Cl)c3)ncnc2cc1OCC1CCC2CN(C)CC12] |

-continued

| Compound | Name | Structure |
|---|---|---|
| 10 | N-[4-(3-chloro-4-fluorophenyl-amino)-7-((7-methyl-7-azabicyclo[2.2.1]heptan-2-yl)methoxy)quinazolin-6-yl]-acrylamide | 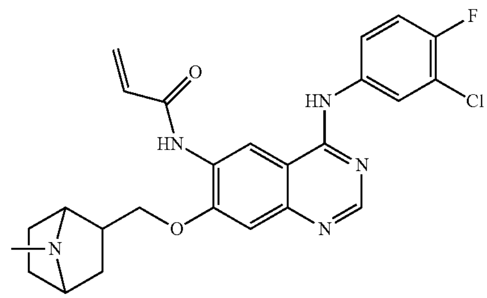 [SMILES: C=CC(=O)Nc1cc2c(Nc3ccc(F)c(Cl)c3)ncnc2cc1OCC1CC2CCC1N2C] |
| 11 | N-[4-(3-chloro-4-fluorophenyl-amino)-7-(2-(3-methyl-3-azabicyclo[3.2.1]octan-8-yl)ethoxy)quinazolin-6-yl]-acrylamide | 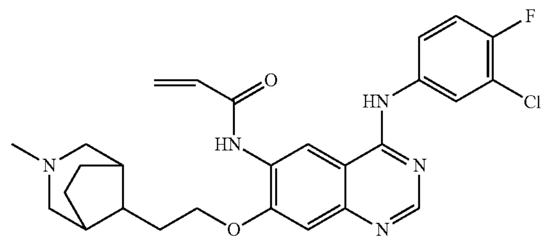 [SMILES: C=CC(=O)Nc1cc2c(Nc3ccc(F)c(Cl)c3)ncnc2cc1OCCC1C2CCC1CN(C)C2] |
| 12 | N-[4-(3-chloro-4-fluorophenyl-amino)-7-((5-methyl-5-azaspiro[2.4]heptan-1-yl)methoxy)quinazolin-6-yl]-acrylamide | 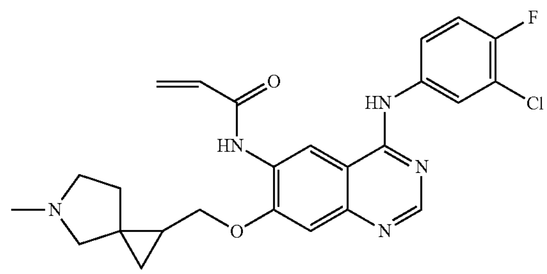 [SMILES: C=CC(=O)Nc1cc2c(Nc3ccc(F)c(Cl)c3)ncnc2cc1OCC1CC12CCN(C)C2] |
| 13 | N-[4-(3-chloro-4-fluorophenyl-amino)-7-((6-methyl-6-azaspiro[2.5]octan-1-yl)methoxy)quinazolin-6-yl]-acrylamide | 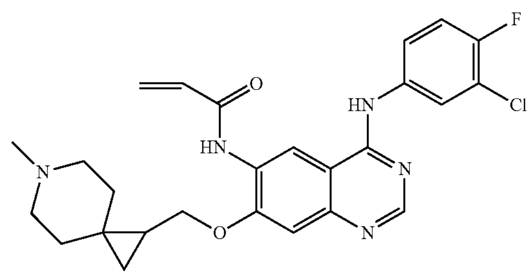 [SMILES: C=CC(=O)Nc1cc2c(Nc3ccc(F)c(Cl)c3)ncnc2cc1OCC1CC12CCN(C)CC2] |
| 14 | N-[4-(3-chloro-4-fluorophenyl-amino)-7-(2-(6-methyl-6-azaspiro[2.5]octan-1-yl)ethoxy)quinazolin-6-yl]-acrylamide | 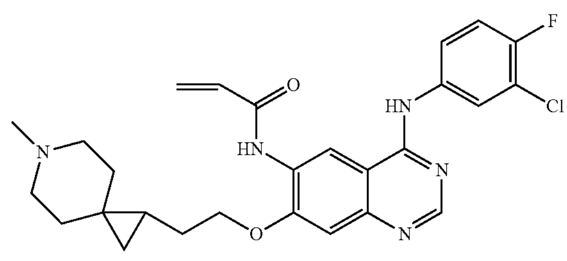 [SMILES: C=CC(=O)Nc1cc2c(Nc3ccc(F)c(Cl)c3)ncnc2cc1OCCC1CC12CCN(C)CC2] |
| 15 | (E)-N-[4-(3-chloro-4-fluorophenyl-amino)-7-(2-((1R,5S,6S)-3-methyl-3-azabicyclo[3.1.0]hexan-6-yl)ethoxy)quinazolin-6-yl]-2-butenamide | 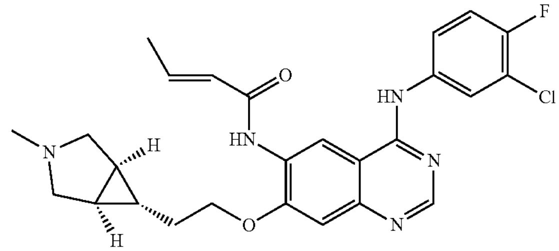 [SMILES: C/C=C/C(=O)Nc1cc2c(Nc3ccc(F)c(Cl)c3)ncnc2cc1OCC[C@@H]1[C@H]2CN(C)C[C@@H]12] |

-continued

| Compound | Name | Structure |
|---|---|---|
| 16 | (E)-N-[4-(3-chloro-4-fluorophenyl-amino)-7-((7-methyl-7-azaspiro[3.5]nonan-2-yl)methoxy)quinazolin-6-yl]-2-butenamide | 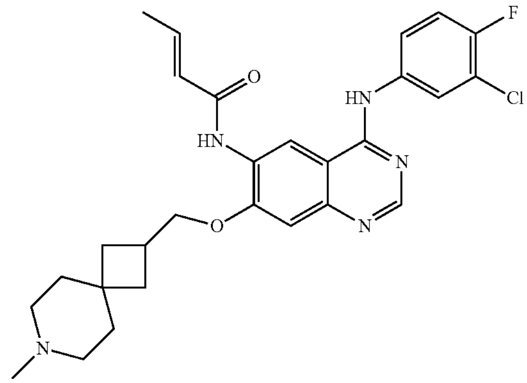 [SMILES: C/C=C/C(=O)Nc1cc2c(Nc3ccc(F)c(Cl)c3)ncnc2cc1OCC1CC2(CCN(C)CC2)C1] |
| 17 | (E)-N-[4-(3-chloro-4-fluorophenyl-amino)-7-((7-methyl-7-azaspiro[3.5]nonan-2-yl)methoxy)quinazolin-6-yl]-2-pentenamide | 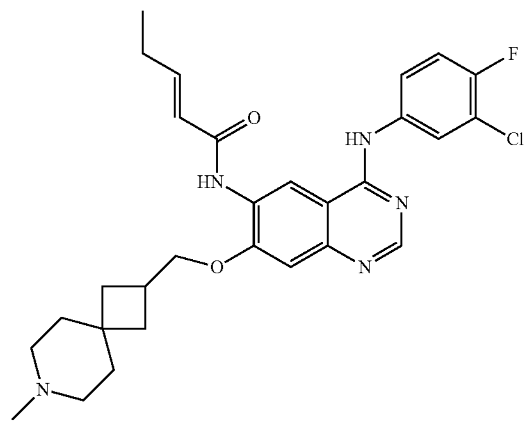 [SMILES: CC/C=C/C(=O)Nc1cc2c(Nc3ccc(F)c(Cl)c3)ncnc2cc1OCC1CC2(CCN(C)CC2)C1] |
| 18 | N-[4-(3-chloro-4-fluorophenyl-amino)-7-((7-methyl-7-azaspiro[3.5]nonan-2-yl)methoxy)quinazolin-6-yl]-acrylamide | 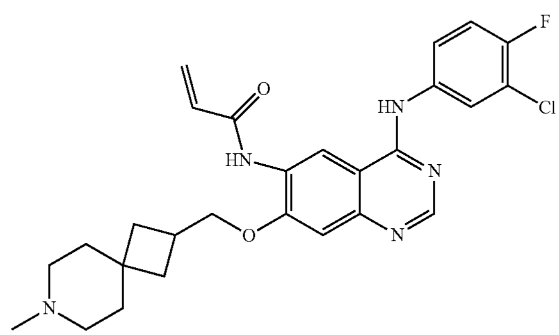 [SMILES: C=CC(=O)Nc1cc2c(Nc3ccc(F)c(Cl)c3)ncnc2cc1OCC1CC2(CCN(C)CC2)C1] |
| 19 | N-[4-(3-chloro-4-fluorophenyl-amino)-7-(2-(7-methyl-7-azaspiro[3.5]nonan-2-yl)ethoxy)quinazolin-6-yl]-acrylamide | 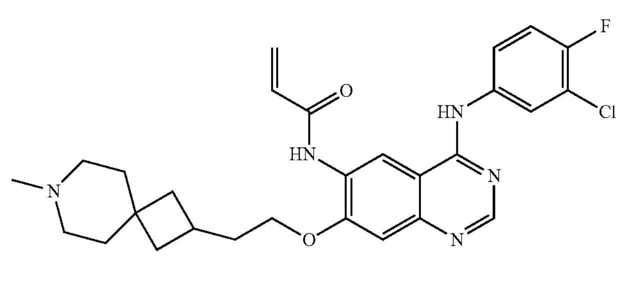 [SMILES: C=CC(=O)Nc1cc2c(Nc3ccc(F)c(Cl)c3)ncnc2cc1OCCC1CC2(CCN(C)CC2)C1] |

| Compound | Name | Structure |
|---|---|---|
| 20 | (E)-N-(4-(3-chloro-4-fluorophenyl-amino)-7-((7-methyl-7-azaspiro[3.5]nonan-2-yl)methoxy)quinazolin-6-yl)-4-dimethylamino-2-butenamide | 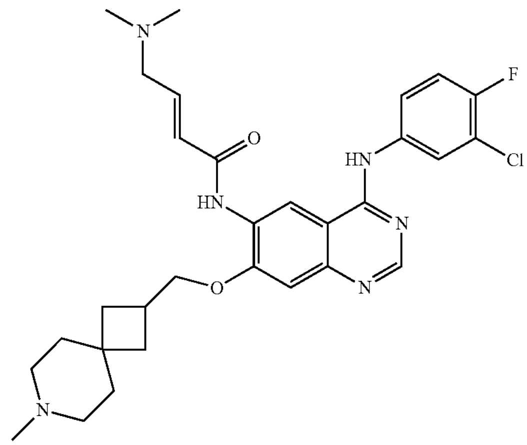 [SMILES: CN(C)C/C=C/C(=O)Nc1cc2c(Nc3ccc(F)c(Cl)c3)ncnc2cc1OCC1CC2(CCN(C)CC2)C1] |
| 21 | (E)-N-[4-(3-chloro-4-fluorophenyl-amino)-7-((2-(3-methyl-3-aza-bicyclo[3.1.0]-6-hexyl)-ethoxy)quinazolin-6-yl)-4-dimethylamino]-crotonamide | 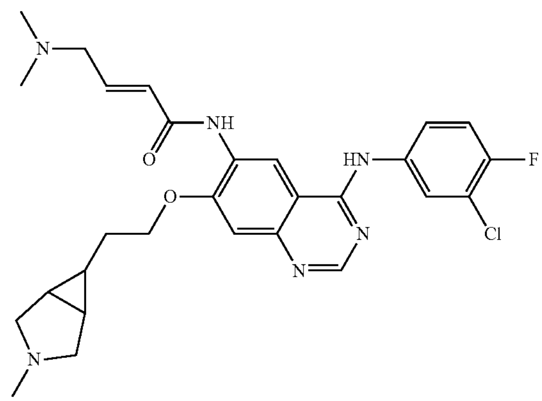 [SMILES: CN(C)C/C=C/C(=O)Nc1cc2c(Nc3ccc(F)c(Cl)c3)ncnc2cc1OCCC1C2CN(C)CC12] |
| 22 | (E)-N-[4-(3-chloro-4-fluorophenyl-amino)-7-(((spiro[3.5]octan-2-yl)methoxy)quinazolin-6-yl)-4-di-methylamino]-crotonamide | 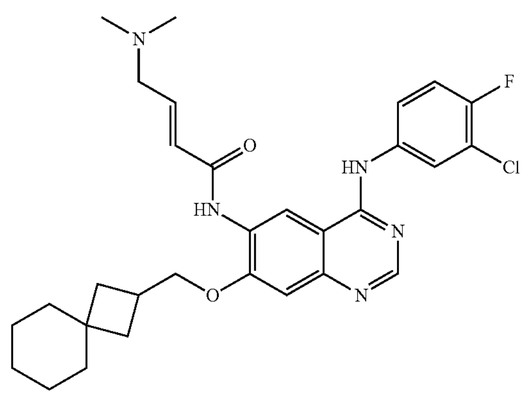 [SMILES: CN(C)C/C=C/C(=O)Nc1cc2c(Nc3ccc(F)c(Cl)c3)ncnc2cc1OCC1CC2(CCCCC2)C1] |
| 23 | (E)-N-(7-(bicyclo[3.1.0]hexan-6-ylmethoxy)-4-(3-chloro-4-fluoro-phenylamino)quinazolin-6-yl)-4-(dimethylamino)but-2-enamide | 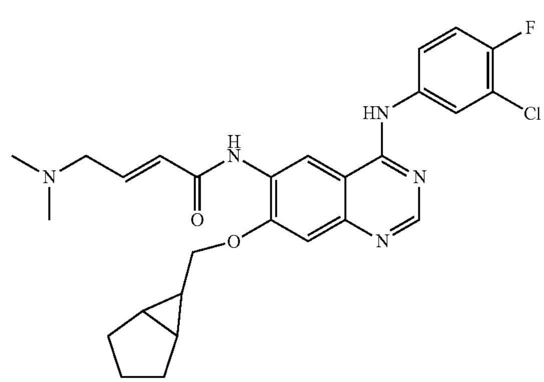 [SMILES: CN(C)C/C=C/C(=O)Nc1cc2c(Nc3ccc(F)c(Cl)c3)ncnc2cc1OCC1C2CCCC21] |

In an embodiment of the preparation of the present compound of the general formula (I), the present compound of the general formula (I) can be prepared by the following specific steps: Reaction Procedure:

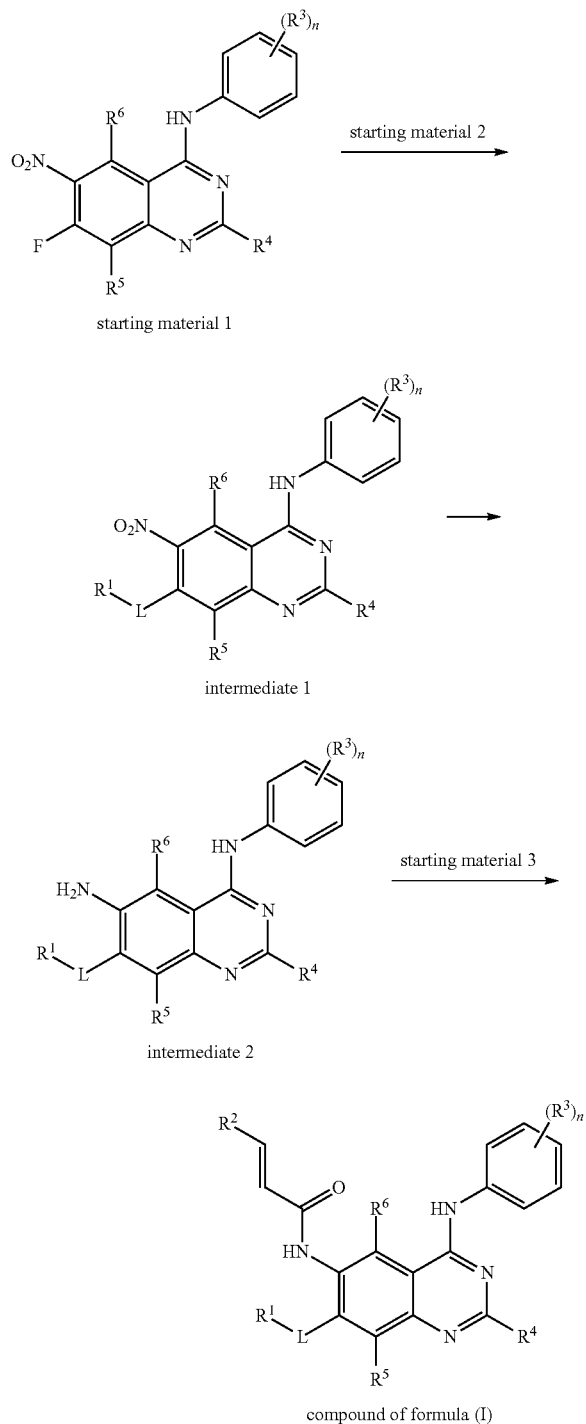

In the above Reaction Procedure, $R^1$, $R^2$, $R^3$, $R^4$, $R^5$, $R^6$, L and n are as defined hereinbefore; the starting material 1 is synthesized according to the methodology provided in US 2005/0250761 A1, the starting material 2=$R^1$-LH; the starting material 3=$R^2$CH=CH—C(O)Cl or $R^2$CH=CH—COOH, 1. Preparation of Intermediate 1

(1) Starting material 2 is dissolved in a non-protonic polar solvent (e.g. THF (tetrahydrofuran), DMF (dimethylformamide), acetonitrile or dioxane). To the mixture is added an alkali (e.g. NaH, potassium carbonate, triethylamine or DIEA (diisopropylethylamine)) in batch under stirring. Then to the mixture is added the solid of Starting material 1. The reaction is carried out at room temperature or under heating to reflux for several hours.

(2) The reaction is cooled to room temperature. Water is added. The mixture is filtered. The filtered cake is dried in vacuum to produce the Intermediate 1. Alternatively, the reaction is cooled to room temperature. Water is added. The mixture is extracted with an organic solvent (e.g. ethyl acetate, dichloromethane or chloroform). Then the organic layer is evaporated to dryness to produce the Intermediate 1.

2. Preparation of Intermediate 2

(1) Intermediate 1 is added in batch to a solvent (e.g. ethanol or THF and the like) optionally containing an acid (e.g. acetic acid or diluted hydrochloric acid and the like). Then an reducing agent (e.g. Fe powder, Zn powder, Pd/C or Raney-Ni and the like) is added. The reaction is carried out at room temperature or under heating.

(2) After the completion of reaction, the reaction mixture is cooled to room temperature, and extracted with an organic solvent (e.g. dichloromethane, ethyl acetate or chloroform and the like). The organic layer is evaporated to dryness. The resulting crude product can be purified by a column chromatography (a silica gel column or a preparative chromatography column) to produce Intermediate 2.

3. Preparation of Compound of Formula (I)

(1) Intermediate 2 is dissolved in an organic solvent (e.g. THF, dichloromethane, acetonitrile or DMF and the like). To the mixture are successively added an organic base (e.g. triethylamine or DIEA and the like) and Starting material 3. The mixture is stirred at room temperature for several hours to react. Alternatively Intermediate 2, Starting material 3 and an organic base (e.g. DIEA or triethylamine and the like) are dissolved in an organic solvent (e.g. dichloromethane, DMF, THF, acetonitrile or DMF and the like). An condensing agent (e.g. HATU (2-(7-azobenzotriazol-1-yl)-N,N,N',N'-tetramethyluronium hexafluorophosphate), EDC (1-ethyl-3-(3-dimethylaminopropyl)carbodiimide) or DCC(N,N'-dicyclohexylcarbodiimide) and the like) are added.

(2) Water is added to the reaction mixture, and the mixture is extracted with an organic solvent (e.g. dichloromethane, ethyl acetate or chloroform and the like). The organic layers are combined. The resulting residue is purified by a column chromatography (a silica gel column or a preparative chromatography column) to produce Compound of formula (I).

The present compound of general formula (I) and a pharmaceutically acceptable salt and a stereoisomer thereof can be administered to a mammal, e.g. human orally, parenterally (intravenously, intramuscularly, subcutaneously or rectally and the like), pulmonarily, and locally. The daily dosage of the present compound can be about 1 to about 1000 mg.

The present compound of formula (I) or a pharmaceutically acceptable salt, or a stereoisomer thereof can be administered alone or in combination with other therapeutical agents, in particularly a second therapeutical agent selected from the group consisting of an antineoplastic agent and an immunosuppressive agent. Said second therapeutical agent is selected from the group consisting of antimetabolite, including but not limited to e.g. capecitabine, gemcitabine and the like; a growth factor inhibitor, including but not limited to e.g. pazopanib, imatinib and the like; an antibody, including but not limited to e.g. herceptin, bevacizumab and the like; a mitotic inhibitor, including but not limited to e.g. paclitaxel, vinorelbine, docetaxel, doxorubicin and the like; antineoplastic hormone, including but not limited to e.g. letrozole, tamoxifen, fulvestrant and the like; alkylating agent, including but not limited to e.g. cyclophosphamide, carmustine and the like; a metal platinum, including but not limited to e.g. carboplatin, cisplatin, oxaliplatin and the like; topoisomerase inhibitor, including but not limited to e.g. topotecan and the like; immunosuppressant, including but not limited to e.g. everolimus and the like. All of components to be administered can be administered at the same time or successively and separately in a form of the single formulation or in a combination of the divided formulations.

The present compound of formula (I), a pharmaceutically acceptable salt thereof or a stereoisomer thereof can be used to treat a hyperplasia disease and a chronic obstructive pulmonary disease. The hyperplasia disease includes cancerous disease and non-cancerous disease. The cancerous disease is selected from the group consisting of cerebroma, lung cancer, nonsmall-cell lung cancer, squamous cell, bladder carcinoma, gastric cancer, ovarian cancer, peritoneal cancer, pancreatic cancer, mammary cancer, head and neck cancer, cervical cancer, endometrial cancer, colorectal cancer, liver cancer, renal carcinoma, adenocarcinoma of esophagus, esophageal squamous cell cancer, solid tumor, non-Hodgkin lymphoma, central nervous system tumor (glioma, gliobastona multiforme, glioma sarcomatosum), prostate carcinoma or thyroid carcinoma; the non-cancerous disease is for example benign hyperplasia of skin or prostate.

The present invention also provides a pharmaceutical composition, containing the present compound of general formula (I) or a pharmaceutically acceptable salt, or a stereoisomer thereof as described above and one or more pharmaceutically acceptable carriers and/or diluents. Said composition can be prepared by mixing the present compound of general formula (I) or a pharmaceutically acceptable salt, or a stereoisomer thereof and one or more conventional pharmaceutically acceptable carrier and/or diluent. Said composition can be prepared into any clinically or pharmaceutically acceptable dosage form to administer orally, parenteral, pulmonary or locally to the patient in need thereof.

For the oral administration, the present compound of general formula (I) or a pharmaceutically acceptable salt, or a stereoisomer thereof can be formulated into a conventional solid preparation, such as tablet, capsule, pill, granule, powder and the like; or the oral liquid preparation, such as an oral solution, an oral suspension, a syrup and the like. For preparing the oral preparation, suitable filler, binder, disintegrant, lubricant, diluent and the like can be added. Conventional filler includes starch, sugar powder, calcium phosphate, calcium sulfate dihydrate, dextrin, microcrystalline cellulose, lactose, pregelatinized starch, mannitol and the like. Conventional binder includes sodium carboxymethylcellulose, PVP-K30, hydroxypropyl cellulose, starch paste, methyl cellulose, ethyl cellulose, hypromellose, gelatinized starch and the like. Conventional disintegrant includes dry starch, polyvinylpolypyrrolidone (cPVP), croscarmellose sodium, sodium carboxymethyl starch, low-substituted hydroxypropyl cellulose and the like. Conventional lubricant includes magnesium stearate, talc powder, sodium dodecylsulfate, gum acacia and the like. Conventional diluent includes water, ethanol, glycerin and the like.

For the parenteral administration, according to the conventional method, the present compound of general formula (I) or a pharmaceutically acceptable salt, or a stereoisomer thereof can be formulated into an injectable preparation, including an injection solution, a sterile injection powder and a concentrated injection solution. For preparing the injectable preparation, a conventional method in the pharmaceutical production can be used, and an aqueous solvent or a nonaqueous solvent can be used. The most commonly used aqueous solvent is water for injection. 0.9% aqueous NaCl solution or other suitable aqueous solution can also be used. The most commonly used nonaqueous solvent is vegetable oil, such as soy oil for injection. The aqueous solution of ethanol, propylene glycol, polyethylene glycol or the like can also be used. For preparing the injectable preparation, an additive can be optionally added, depending on the nature of drug. The additive includes an osmotic regulator, a pH-value regulator, a solubilizer, a filler, an antioxidant, a bacteriostatic agent, an emulsifier, a suspending agent or the like.

For the rectal, pulmonary or local administration, the present compound of general formula (I) or a pharmaceutically acceptable salt, or a stereoisomer thereof can be formulated into a suppository, an inhalant, a spraying agent, an ointment, a cream, a gel, a powder, a lotion, a drop, a transdermal patch and the like according to the conventional method.

It is demonstrated that the present invention has an excellent antineoplastic effect. The present invention is therefore expected to have a good therapeutic effect on a hyperplasia disease and a chronic obstructive pulmonary disease and reduce the formation of drug resistance. In addition, it is easy to prepare the present compound; the present invention has a stable quality, and therefore the present invention is apt to be produced on the industrial scale.

BEST MODE OF CARRYING OUT THE INVENTION

The following examples are intended to illustrate the invention and are not to be construed as being limitations thereon. All of the technical solutions that can be accomplished based on the above disclosure fall in the scope of the present invention.

In the examples, the used starting materials are commercially available, for example, from Jingyan Chemicals (Shanghai); Titan chemical (Shanghai); Darui (Shanghai); Ouhechem (Beijing); Tetranov Biopharm (Zhengzhou); Guanghan Bio-Tech (Sichuan); Accela ChemBio (Shanghai); Alfa Aesar (Tianjin); TCI (Shanghai), J&K (Beijing); and Bepharm (Shanghai).

For convenience, the following well-known abbreviations are used hereinafter to describe the compounds.
DMF: dimethylformamide
THF: tetrahydrofuran
DIPEA/DIEA: diisopropylethylamine
EA: ethyl acetate
EtOH: ethanol
DCM: dichloromethane
MeOH: methanol
HATU: 2-(7-azobenzotriazol-1-yl)-N,N,N',N'-tetramethyluronium hexafluorophosphate
DCC: N,N-dicyclohexylcarbodiimide
EDC: 1-ethyl-3-(3-dimethylaminopropyl)carbodiimide
DMAP: 4-dimethylaminopyridine

I. Preparation Examples for the Present Compound

N-(4-(3-chloro-4-fluorophenyl))-7-fluoro-6nitroquinazolin-4-amine, as the starting material for the present compound, was prepared according to US 2005/0250761 A1:

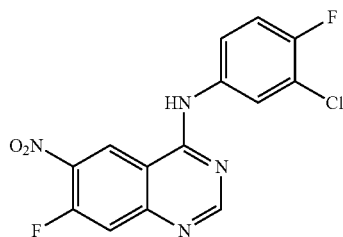 [SMILES: O=[N+]([O-])c1cc2c(Nc3ccc(F)c(Cl)c3)ncnc2cc1F]

The steps were as follows:
Reaction Procedures:

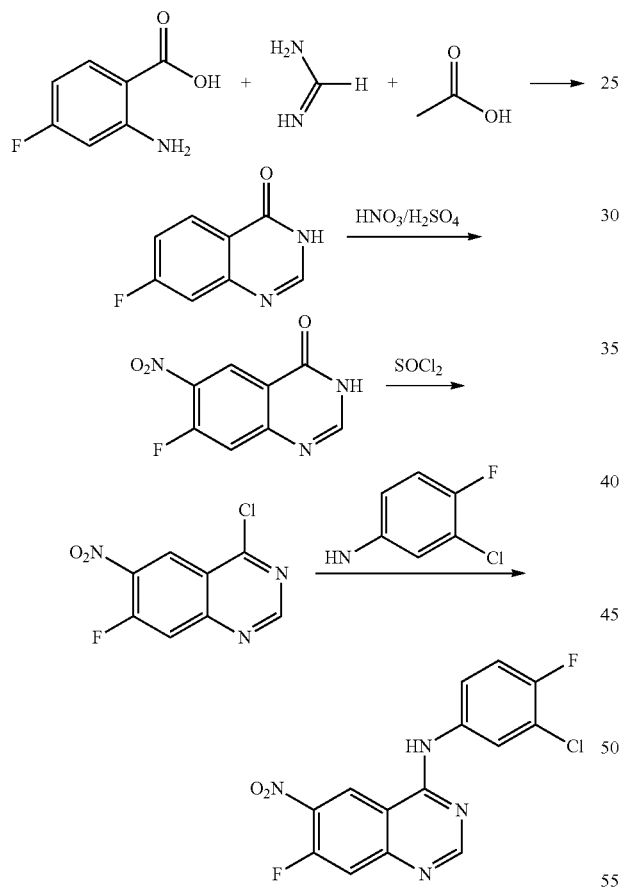

2-amino-4-fluorobenzoic acid, acetic acid and formamidine were reacted under heating to reflux in the presence of 2-methoxyethanol to produce 7-fluoro-3H-quinazolin-4-one. The resulting product was nitrified to produce 7-fluoro-6-nitro-3H-quinazolin-4-one, which was treated with thionyl chloride to produce 4-chloro-6nitro-7-fluoro-3H-quinazoline. The resulting product was dissolved in isopropanol, 4-fluoro-3-chlorophenylamine was added to produce N-(4-(3-chloro-4-fluorophenyl))-7-fluoro-6nitroquinazolin-4-amine.

Example 1 Preparation of (E)-N-[7-(8-oxabicyclo[3.2.1]octan-3-yloxy)-4-(3-chloro-4-fluorophenylamino)quinazolin-6-yl]-4-(piperidin-1-yl)-2-butenamide (Compound 1)

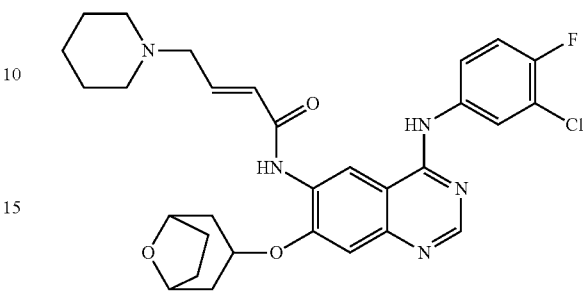

(1) Prepration of 7-(8-oxabicyclo[3.2.1]octan-3-yloxy)-N-(4-(3-chloro-4-fluorophenyl))-6-nitroquinazolin-4-amine

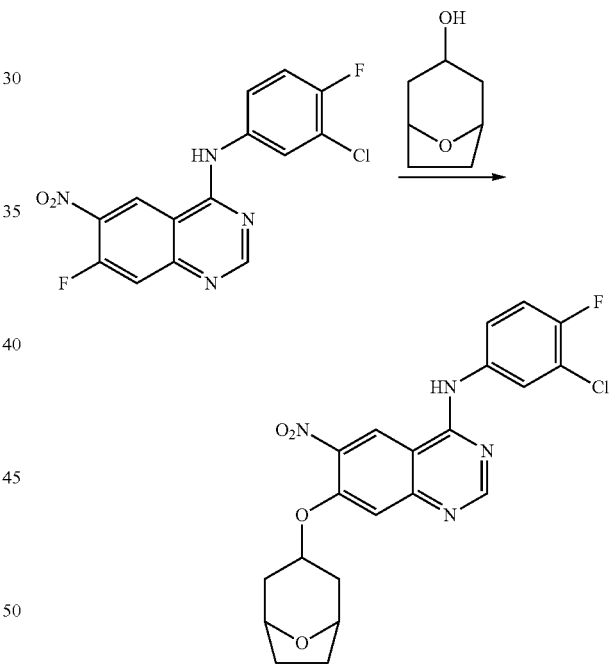

To a round-bottom flask containing NaH (468 mg, 12 mmol) was added DMF (20 mL) under an ice bath, and then was added dropwise a solution of 8-oxabicyclo[3.2.1]octan-3-ol (1.0 g, 7.8 mmol) in DMF (2 mL). The mixture was stirred for 30 min. Then N-(4-(3-chloro-4-fluorophenyl))-7-fluoro-6-nitroquinazolin-4-amine (1.75 g, 5.2 mmol) was added in batch thereto. The mixture was warmed up spontaneously to room temperature and reacted overnight. Water (60 mL-80 mL) was added. The precipitate was formed and filtered by suction to produce a solid, which was dried in vacuum to produce 7-(8-oxabicyclo[3,2,1]octan-3-yloxy)-N-(4-(3-chloro-4-fluorophenyl))-6-nitroquinazolin-4-amine (2.3 g) in a yield of 100%.

(2) Preparation of 7-(8-oxabicyclo[3.2.1]octan-3-yloxy)-N-(4-(3-chloro-4-fluorophenyl))quinazolin-4,6-diamine

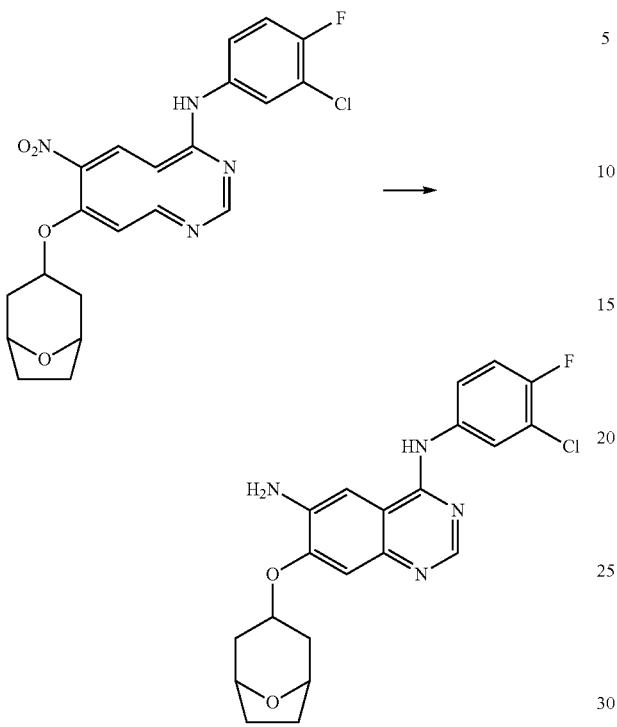

7-(8-oxabicyclo[3.2.1]octan-3-yloxy)-N-(4-(3-chloro-4-fluorophenyl))-6-nitroquinazolin-4-amine (2.3 g, 5.2 mmol) was dissolved in a mixed solution (120 mL) of glacial acetic acid and ethanol (glacial acetic acid/ethanol=1/3). Then Fe powder (2.04 g, 36.4 mmol) was added. The mixture was warmed up spontaneously to room temperature and reacted overnight. The reaction was filtered by suction, and ethanol was removed in vacuum. An appropriate amount of water was added. The mixture was neutralized with a saturated sodium bicarbonate solution until the mixture became neutral. The mixture was extracted with ethyl acetate. The organic layer was concentrated to produce a crude product, which was purified by a silica gel column chromatography (eluted with DCM/methanol=10/1) to produce 7-(8-oxabicyclo[3.2.1]octan-3-yloxy)-N-(4-(3-chloro-4-fluorophenyl))quinazolin-4,6-diamine 500 mg in a yield of 23%.

(3) Preparation of (E)-N-[7-(8-oxabicyclo[3.2.1]octan-3-yloxy)-4-(3-chloro-4-fluorophenylamino)quinazolin-6-yl]-4-bromo-2-butenamide

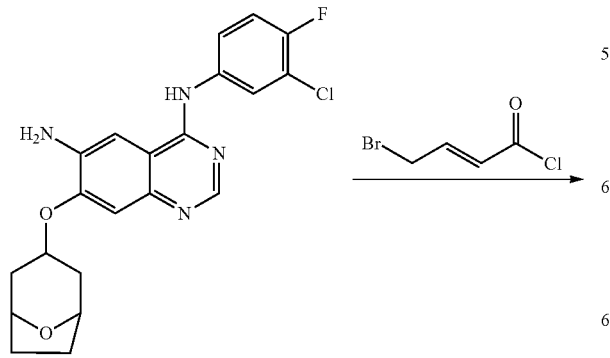

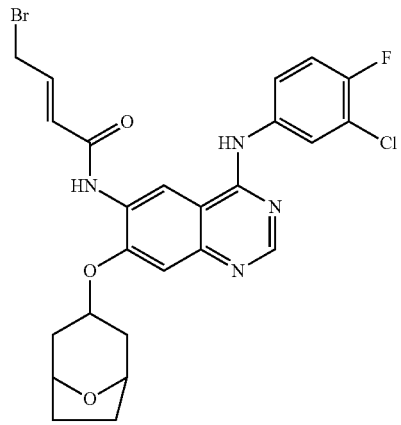

7-(8-oxabicyclo[3.2.1]octan-3-yloxy)-N-(4-(3-chloro-4-fluorophenyl))quinazolin-4,6-diamine (500 mg, 1.2 mmol) was dissolved in dichloromethane (20 mL). To the mixture were successively added triethylamine (976 mg) and 4-bromo-2-butenoyl chloride (275 mg, 1.5 mmol). The mixture was stirred at room temperature for 12 h. An appropriate amount of water was added to the reaction. The reaction was extracted with ethyl acetate. The organic layer was dried over anhydrous sodium sulphate and concentrated to produce a crude product, which was directly used in the next step without purification.

(4) Preparation of (E)-N-[7-(8-oxabicyclo[3.2.1]octan-3-yloxy)-4-(3-chloro-4-fluorophenylamino)quinazolin-6-yl]-4-(piperidin-1-yl)-2-butenamide

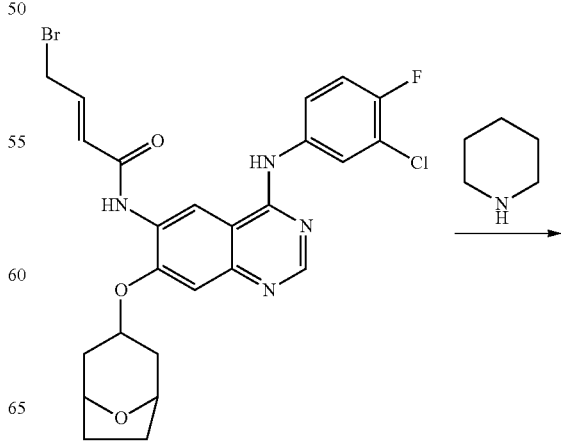

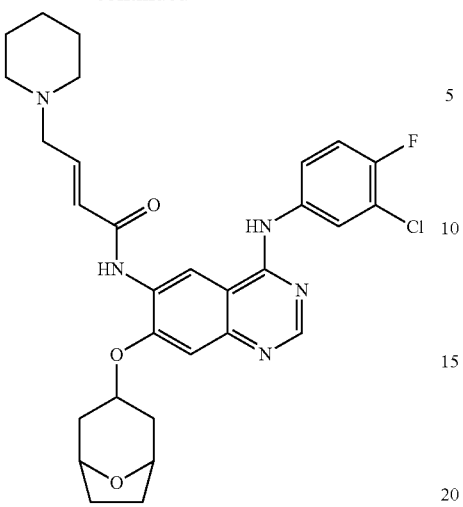

The product from the previous step, (E)-N-[7-(8-oxabicyclo[3.2.1]octan-3-yloxy)-4-(3-chloro-4-fluorophenylamino)quinazolin-6-yl]-4-bromo-2-butenamide was dissolved in acetonitrile (20 mL). Piperidine (205 mg, 2.4 mmol) and cesium carbonate (787 mg, 2.4 mmol) were added. The reaction was conducted at 40° C. for 12 h under stirring. An appropriate amount of water was added to the reaction. The reaction was extracted with dichloromethane. The organic layer was dried over anhydrous sodium sulphate, concentrated, and purified by a silica gel column chromatography (eluted with dichloromethane/methanol=5/1) to produce (E)-N-[7-(8-oxabicyclo[3.2.1]octan-3-yloxy)-4-(3-chloro-4-fluorophenylamino)quinazolin-6-yl]-4-(piperidin-1-yl)-2-butenamide 20 mg) in a yield of 3%.

Molecular formula: $C_{30}H_{33}ClFN_5O_3$

Mass spectrum (m/e): 566.3 (M+1) 283.6 (M/2)

$^1$HNMR: (400 MHz, CDCl$_3$) δ9.13 (s, 1H), 8.67 (s, 1H), 8.10 (s, 1H), 8.00 (d, 1H), 7.54 (m, 2H), 7.18 (t, 1H), 7.07 (m, 1H), 6.22 (d, 1H), 4.98 (m, 1H), 4.60 (m, 2H), 3.25 (m, 2H), 2.51 (m, 4H), 2.23 (m, 4H), 1.88-2.03 (m, 10H).

Example 2 Preparation of (E)-N-[7-(7-oxabicyclo[2.2.1]heptan-2-yloxy)-4-(3-chloro-4-fluorophenylamino)quinazolin-6-yl]-4-(piperidin-1-yl)-2-butenamide (Compound 2)

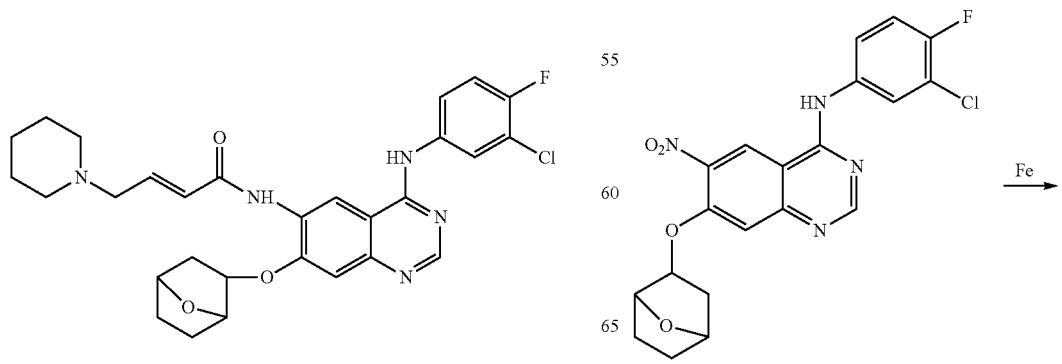

(1) Preparation of 7-(7-oxabicyclo[2.2.1]heptan-2-yloxy)-N-(4-(3-chloro-4-fluorophenyl))-6-nitroquinazolin-4-amine

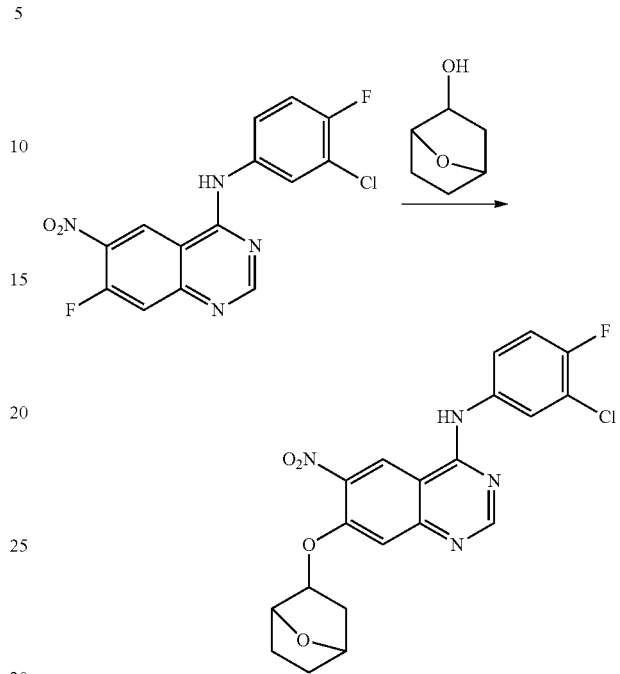

To a round-bottom flask containing NaH (531 mg, 22 mmol) was added DMF (20 mL) under an ice bath, and then was added dropwise a solution of 7-oxabicyclo[2.2.1]heptan-2-ol (1.0 g, 8.8 mmol) in DMF (2 mL). The mixture was stirred for 30 min. Then N-(4-(3-chloro-4-fluorophenyl))-7-fluoro-6-nitroquinazolin-4-amine (1.98 g, 5.9 mmol) was added in batch. The mixture was warmed up spontaneously to room temperature and reacted overnight. Water (60 mL-80 mL) was added. The precipitate was formed and filtered by suction to produce a filtered cake, which was dried in vacuum to produce 7-(7-oxabicyclo[2.2.1]heptan-2-yloxy)-N-(4-(3-chloro-4-fluorophenyl))-6-nitroquinazolin-4-amine (2.5 g) in a yield of 100%.

(2) Preparation of 7-(7-oxabicyclo[2.2.1]heptan-2-yloxy)-N-(4-(3-chloro-4-fluorophenyl))quinazolin-4,6-diamine

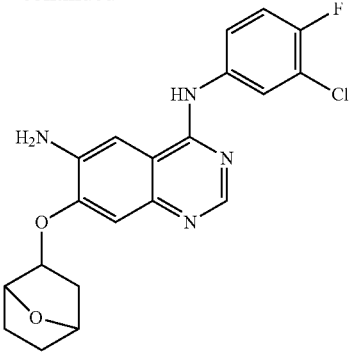

7-(7-oxabicyclo[2.2.1]heptan-2-yloxy)-N-(4-(3-chloro-4-fluorophenyl))-6-nitroquinazolin-4-amine (2.5 g, 5.8 mmol) was dissolved in a mixed solution (120 mL) of glacial acetic acid and ethanol (glacial acetic acid/ethanol=1/3). Then Fe powder (2.28 g, 40.7 mmol) was added. The mixture was warmed up spontaneously to room temperature and reacted overnight. The reaction was filtered by suction, and ethanol was removed in vacuum. An appropriate amount of water was added. The mixture was neutralized with a saturated sodium bicarbonate solution until the mixture became neutral. The mixture was extracted with ethyl acetate. The organic layer was concentrated to produce a crude product, which was purified by a silica gel column chromatography (eluted with DCM/methanol=10/1) to produce 7-(7-oxabicyclo[2.2.1]heptan-2-yloxy)-N-(4-(3-chloro-4-fluorophenyl))quinazolin-4,6-diamine 600 mg) in a yield of 25%.

(3) Preparation of (E)-N-[7-(7-oxabicyclo[2.2.1]heptan-2-yloxy)-4-(3-chloro-4-fluorophenylamino)quinazolin-6-yl]-4-bromo-2-butenamide

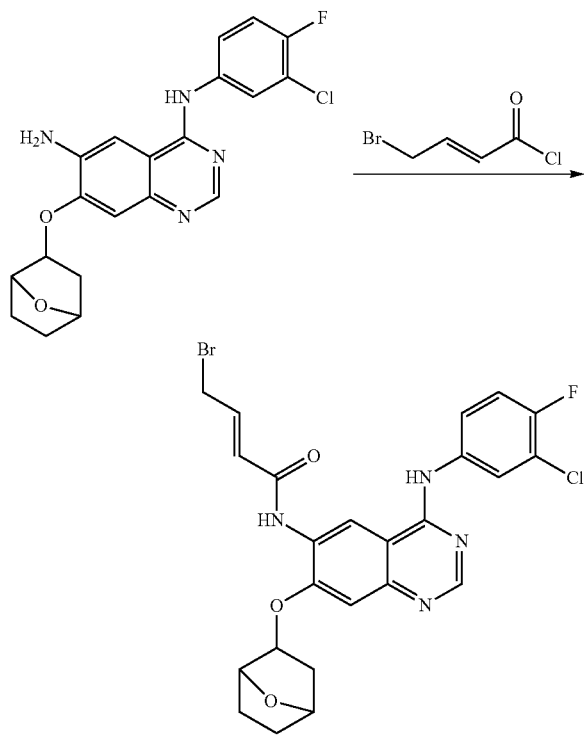

7-(7-oxabicyclo[2.2.1]heptan-2-yloxy)-N-(4-(3-chloro-4-fluorophenyl))quinazolin-4,6-diamine (600 mg, 1.5 mmol) was dissolved in dichloromethane (20 mL). To the mixture were successively added triethylamine (1.21 g) and 4-bromo-2-butenoyl chloride (366 mg, 2.0 mmol). The mixture was stirred at room temperature for 12 h. An appropriate amount of water was added to the reaction. The reaction was extracted with ethyl acetate. The organic layer was dried over anhydrous sodium sulphate and concentrated to produce a crude product, which was directly used in the next step without purification.

(4) Preparation of (E)-N-[7-(7-oxabicyclo[2.2.1]heptan-2-yloxy)-4-(3-chloro-4-fluorophenylamino)quinazolin-6-yl]-4-(piperidin-1-yl)-2-butenamide

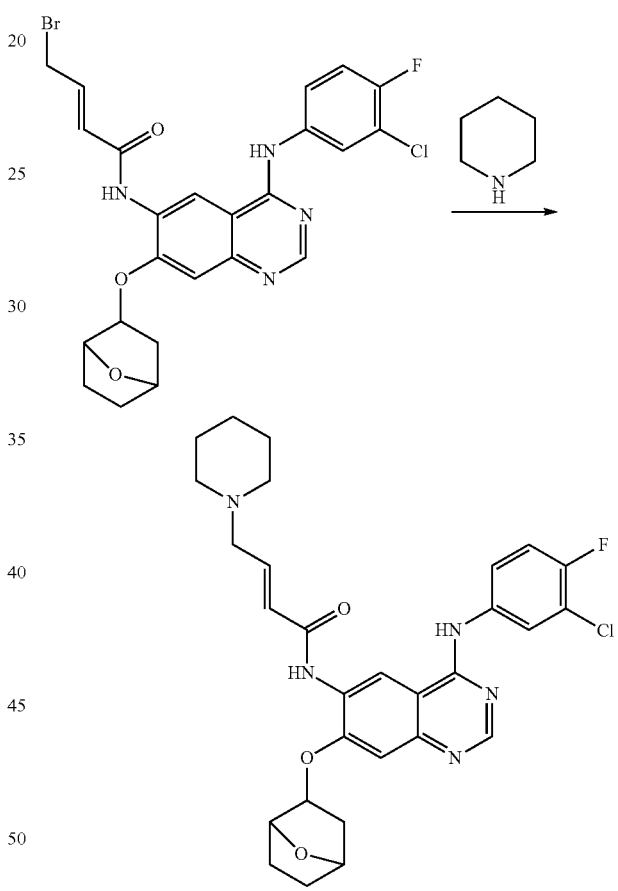

The product from the previous step, (E)-N-[7-(7-oxabicyclo[2.2.1]heptan-2-yloxy)-4-(3-chloro-4-fluorophenylamino)quinazolin-6-yl]-4-bromo-2-butenamide was dissolved in acetonitrile (20 mL). Piperidine (255 mg, 3.0 mmol) and cesium carbonate (978 mg, 3.0 mmol) were added. The reaction was conducted at 40° C. for 12 h under stirring. An appropriate amount of water was added to the reaction. The reaction was extracted with dichloromethane. The organic layer was dried over anhydrous sodium sulphate, concentrated, and purified by a silica gel column chromatography (eluted with dichloromethane/methanol=5/1) to produce (E)-N-[7-(7-oxabicyclo[2.2.1]heptan-2-yloxy)-4-(3-chloro-4-fluorophenylamino)quinazolin-6-yl]-4-(piperidin-1-yl)-2-butenamide (25 mg) in a yield of 3%.

Molecular formula: $C_{29}H_{31}ClFN_5O_3$

Mass spectrum (m/e): 552.2 (M+1)

$^1$HNMR: (400 MHz, CDCl$_3$) δ9.13 (s, 1H), 8.65 (s, 1H), 8.20 (s, 1H), 7.97 (d, 1H), 7.72 (s, 1H), 7.54 (m, 1H), 7.18 (m, 2H), 6.23 (d, 1H), 4.80 (m, 2H), 4.64 (m, 1H), 3.23 (m, 2H), 2.49 (m, 4H), 2.20 (m, 2H), 1.88-2.03 (m, 10H).

Example 3 Preparation of (E)-N-[4-(3-chloro-4-fluorophenylamino)-7-(2-methyl-2,7-diazaspiro[4.5]decan-7-yl)quinazolin-6-yl]-4-(piperidin-1-yl)-2-butenamide (Compound 3)

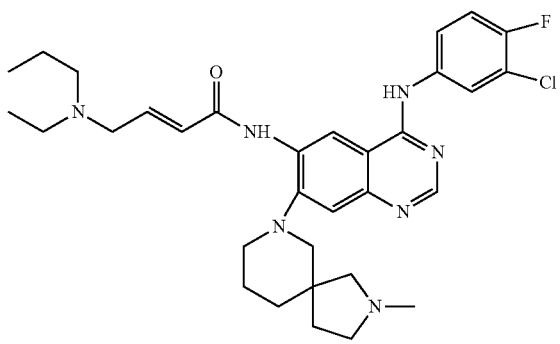 [SMILES: CCCN(CC)C/C=C/C(=O)Nc1cc2c(Nc3ccc(F)c(Cl)c3)ncnc2cc1N1CCCC2(CCN(C)C2)C1]

(1) Preparation of N-(4-(3-chloro-4-fluorophenyl))-7-(2-methyl-2,7-diazaspiro[4.5]decan-7-yl)-6-nitroquinazolin-4-amine

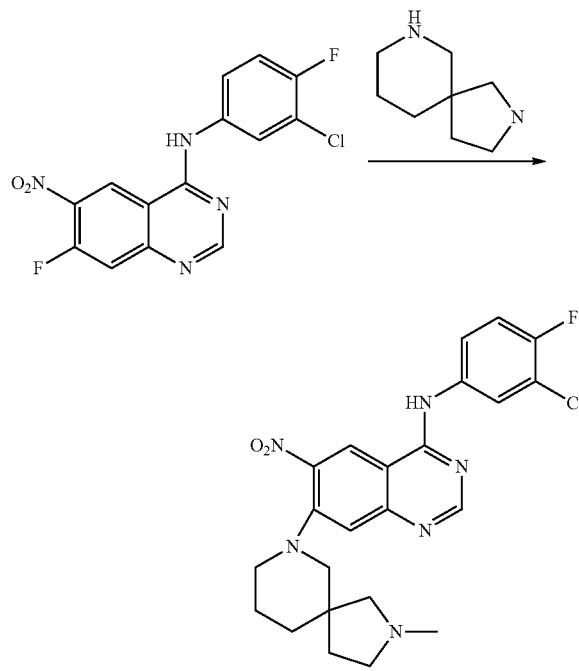

2-methyl-2,7-diazaspiro[4.5]decane (500 mg, 3.2 mmol), potassium carbonate (1.0 g, 7.2 mmol) and N-(4-(3-chloro-4-fluorophenyl))-7-fluoro-6-nitroquinazolin-4-amine (560 mg, 1.7 mmol) were dissolved in acetonitrile (20 mL). The mixture was added to 82° C. and reacted for 4 h. The reaction was cooled to room temperature. Water (30 mL) was added. The reaction was extracted with ethyl acetate. The organic layer was dried over anhydrous sodium sulphate, filtered, and concentrated. The concentrate was purified by a silica gel column chromatography (eluted with dichloromethane/methanol=40/1) to produce N-(4-(3-chloro-4-fluorophenyl))-7-(2-methyl-2,7-diazaspiro[4.5]decan-7-yl)-6-nitroquinazolin-4-amine (600 mg) in a yield of 75%.

(2) Preparation of N-(4-(3-chloro-4-fluorophenyl))-7-(2-methyl-2,7-diazaspiro[4.5]decan-7-yl)quinazolin-4,6-diamine

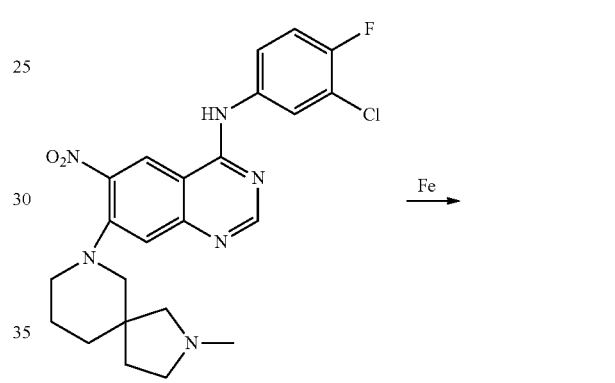

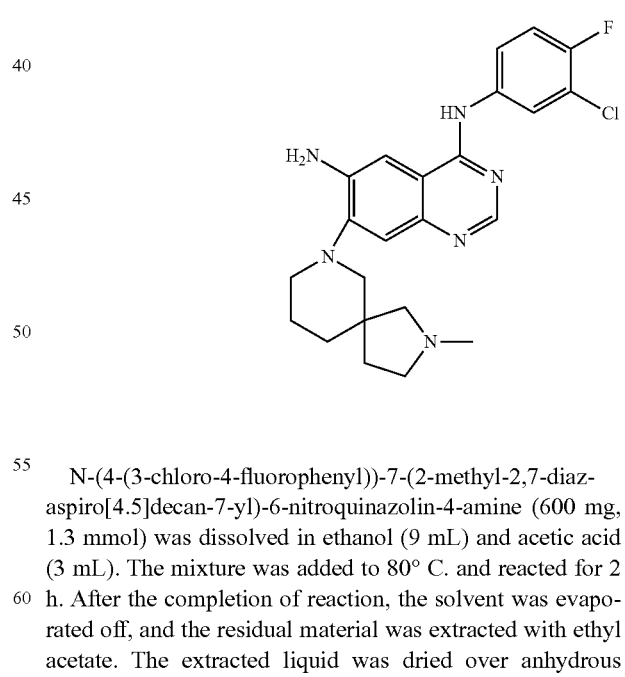

N-(4-(3-chloro-4-fluorophenyl))-7-(2-methyl-2,7-diazaspiro[4.5]decan-7-yl)-6-nitroquinazolin-4-amine (600 mg, 1.3 mmol) was dissolved in ethanol (9 mL) and acetic acid (3 mL). The mixture was added to 80° C. and reacted for 2 h. After the completion of reaction, the solvent was evaporated off, and the residual material was extracted with ethyl acetate. The extracted liquid was dried over anhydrous sodium sulphate and concentrated to dryness to produce N-(4-(3-chloro-4-fluorophenyl))-7-(2-methyl-2,7-diazaspiro[4.5]decan-7-yl)quinazolin-4,6-diamine (500 mg) in a yield of 87%.

(3) Preparation of (E)-N-[4-(3-chloro-4-fluorophenylamino)-7-(2-methyl-2,7-diazaspiro[4.5]decan-7-yl)quinazolin-6-yl]-4-bromo-2-butenamide

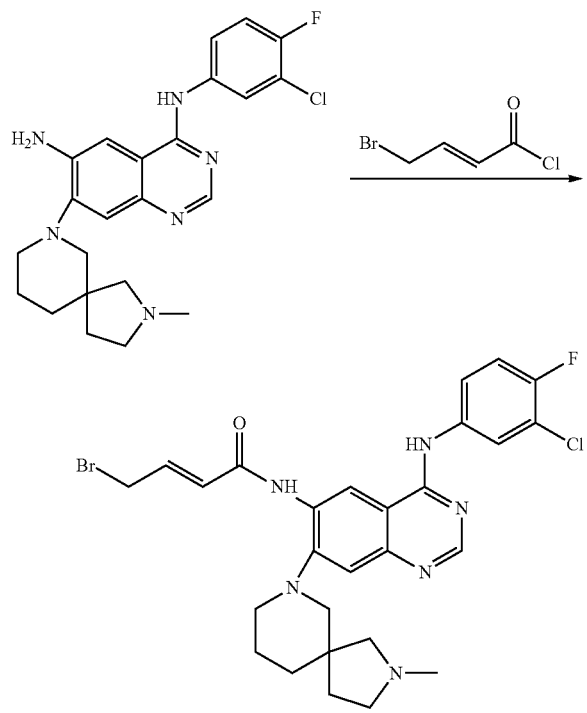

N-(4-(3-chloro-4-fluorophenyl))-7-(2-methyl-2,7-diazaspiro[4.5]decan-7-yl)quinazolin-4,6-diamine (500 mg, 1.1 mmol) and (E)-4-bromo-2-butenoyl chloride (1.1 g, 6 mmol) was dissolved in THF (20 mL). To the mixture was successively added DIPEA (2 mL). The mixture was stirred at room temperature for 1 h. To the solution was added water (30 mL). The solution was extracted with ethyl acetate. The organic layers were combined and dried over anhydrous sodium sulphate, and evaporated to dryness. The resulting solid was purified by a silica gel column chromatography (eluted with dichloromethane/methanol=60/1) to produce (E)-N-[4-(3-chloro-4-fluorophenylamino)-7-(2-methyl-2,7-diazaspiro[4.5]decan-7-yl)quinazolin-6-yl]-4-bromo-2-butenamide (230 mg) in a yield of 36%.

(4) Preparation of (E)-N-[4-(3-chloro-4-fluorophenylamino)-7-(2-methyl-2,7-diazaspiro[4.5]decan-7-yl)quinazolin-6-yl]-4-(piperidin-1-yl)-2-butenamide

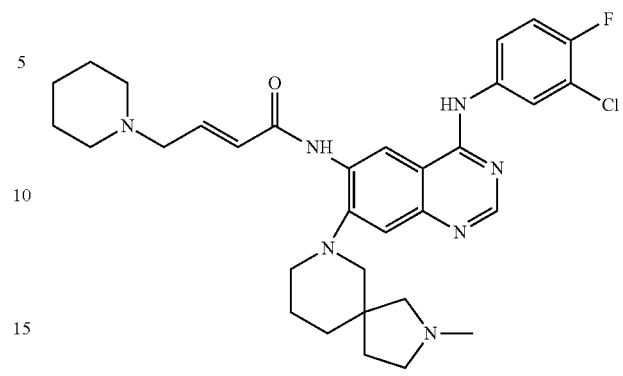

(E)-N-[4-(3-chloro-4-fluorophenylamino)-7-(2-methyl-2,7-diazaspiro[4.5]decan-7-yl)quinazolin-6-yl]-4-bromo-2-butenamide (240 mg, 0.4 mmol), piperidine (70 mg, 0.8 mmol) and potassium carbonate (110 mg, 0.8 mmol) were dissolved in acetonitrile (20 mL). The mixture was reacted at 50° C. for 8 h. After the completion of reaction, to the reaction mixture was added an appropriate amount of water. The reaction was extracted with ethyl acetate. The organic layer was dried over anhydrous sodium sulphate and filtered. The filtrate was concentrated. The concentrate was purified by a silica gel column chromatography (eluted with dichloromethane/methanol=15/1) to produce (E)-N-[4-(3-chloro-4-fluorophenylamino)-7-(2-methyl-2,7-diazaspiro[4.5]decan-7-yl)quinazolin-6-yl]-4-(piperidin-1-yl)-2-butenamide (18 mg) in a yield of 8%.

Molecular formula: $C_{32}H_{39}ClFN_7O$

Mass spectrum (m/e): 592.3 (M+1), 296.6 (M/2)

$^1$HNMR: (400 MHz, CDCl$_3$) δ9.00 (s, 1H), 8.74 (s, 1H), 8.65 (s, 1H), 8.06 (s, 1H), 7.99 (d, 1H), 7.58 (s, 1H), 7.58 (s, 1H), 7.08 (m, 2H), 6.16 (d, 1H), 3.21 (d, 2H), 2.90-3.20 (m, 7H), 2.46-2.78 (m, 5H), 2.38 (s, 3H), 1.28-1.79 (m, 12H).

Example 4 Preparation of N-[4-(3-chloro-4-fluorophenylamino)-7-(8-methyl-8-azabicyclo[3.2.1]octan-3-yloxy)quinazolin-6-yl]-acrylamide (Compound 4)

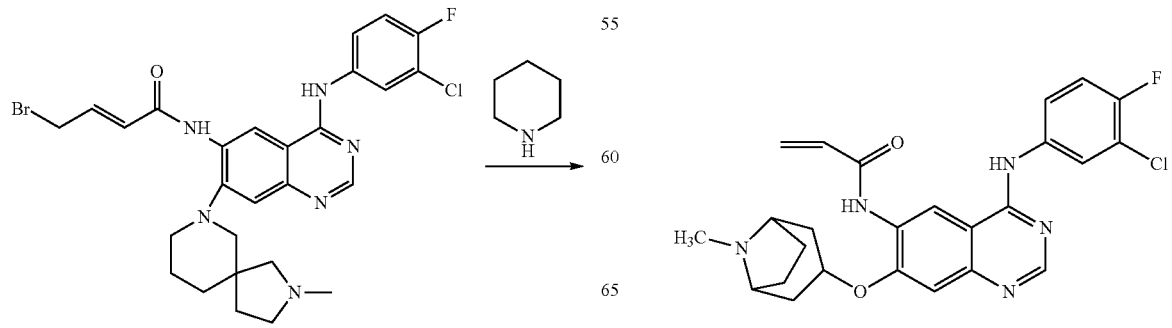

(1) Preparation of N-(4-(3-chloro-4-fluorophenyl))-7-(8-methyl-8-azabicyclo[3.2.1]octan-3-yloxy)-6-nitroquinazolin-4-amine

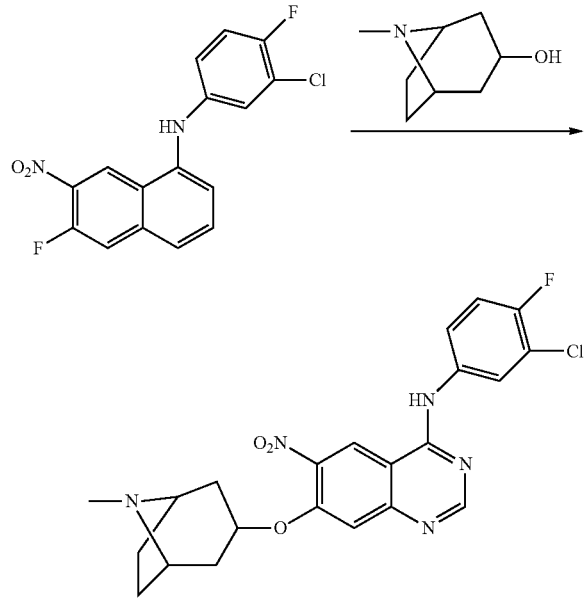

8-methyl-8-azabicyclo[3.2.1]octan-3-ol (0.7 g, 5 mmol) was dissolved in DMF (20 mL). 60% sodium hydride (0.4 g, 10 mmol) was added in batch in an ice bath under an atmosphere of $N_2$. The mixture was moved to an atmosphere of room temperature and stirred for 1 h. N-(4-(3-chloro-4-fluorophenyl))-7-fluoro-6-nitroquinazolin-4-amine (1.12 g, 3.3 mmol) was added. The mixture was stirred at 50° C. overnight. After the completion of reaction, water (50 mL) was added. The mixture was extracted with EA. The organic layer was rotary-evaporated to dryness under a reduced pressure to produce N-(4-(3-chloro-4-fluorophenyl))-7-(8-methyl-8-azabicyclo[3.2.1]octan-3-yloxy)-6-nitroquinazolin-4-amine (560 mg) in a yield of 37%.

(2) Preparation of N-(4-(3-chloro-4-fluorophenyl))-7-(8-methyl-8-azabicyclo[3.2.1]octan-3-yloxy)quinazolin-4,6-diamine

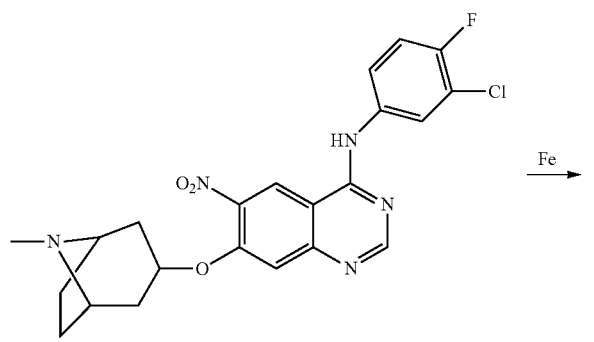

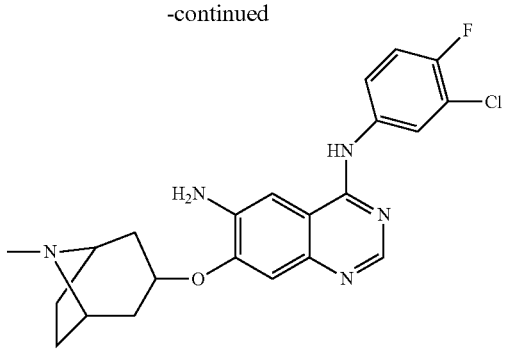

N-(4-(3-chloro-4-fluorophenyl))-7-(8-methyl-8-azabicyclo[3.2.1]octan-3-yloxy)-6-nitroquinazolin-4-amine (560 mg, 1.22 mmol) was dissolved in a mixed solvent (20 mL) of acetic acid and ethanol ($CH_3COOH$/EtOH=1/3). Then Fe powder (343 mg, 6.12 mmol) was added. The mixture was warmed up to 70° C. and stirred for 1 h. After the completion of reaction, the mixture was rotary-evaporated under a reduced pressure to remove EtOH. Water (30 mL) was added. The mixture was extracted with EA, and adjusted with 1 mol/L NaOH solution until the mixture became basic. The mixture was extracted with EA. The organic layer was rotary-evaporated to dryness under a reduced pressure to produce N-(4-(3-chloro-4-fluorophenyl))-7-(8-methyl-8-azabicyclo[3.2.1]octan-3-yloxy)quinazolin-4,6-diamine (360 mg) in a yield of 69%.

(3) Preparation of N-[4-(3-chloro-4-fluorophenylamino)-7-(8-methyl-8-azabicyclo[3.2.1]octan-3-yloxy)quinazolin-6-yl]-acrylamide

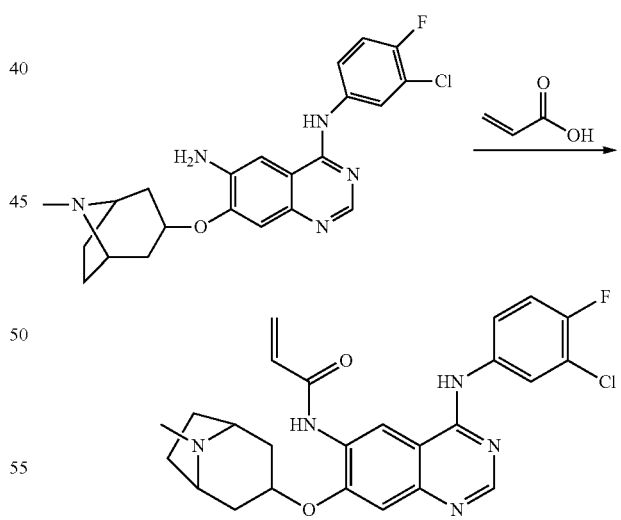

Acrylic acid (243 mg, 3.37 mmol) was dissolved in DMF (10 mL). To the resulting mixture was added DMAP (162 mg, 1.35 mmol), N-(4-(3-chloro-4-fluorophenyl))-7-(8-methyl-8-azabicyclo[3.2.1]octan-3-yloxy)quinazolin-4,6-diamine (360 mg, 0.84 mmol) and EDC (193 mg, 1.01 mmol) under an ice bath. The mixture was stirred at room temperature overnight. After the completion of reaction, water (50 mL) was added. The mixture was extracted with EA. The organic layer was rotary-evaporated to dryness under a reduced pressure. The residue was washed with diethyl ether to produce N-[4-(3-chloro-4-fluorophenylamino)-7-(8-methyl-8-azabicyclo[3.2.1]octan-3-yloxy)quinazolin-6-yl]-acrylamide (54 mg) in a yield of 13%.

Molecular formula: $C_{25}H_{25}ClFN_5O_2$

Mass spectrum (m/e): 482.2 (M+1), 241.6 (M/2)

$^1$HNMR: (400 MHz, DMSO-d$_6$) δ9.78 (s, 1H), 9.55 (s, 1H), 8.72 (s, 1H), 8.52 (s, 1H), 8.14 (d, 1H), 7.80 (d, 1H), 7.41 (t, 1H), 7.11 (s, 1H), 6.58 (m, 1H), 6.30 (d, 1H), 5.80 (d, 1H), 4.83 (m, 1H), 3.03 (m, 2H), 2.12 (s, 3H), 2.10 (m, 2H), 1.88 (m, 6H).

Example 5 Preparation of N-[4-(3-chloro-4-fluorophenylamino)-7-(8-methyl-1-oxa-8-azaspiro[4.5]decan-3-yloxy)quinazolin-6-yl]-acrylamide (Compound 5)

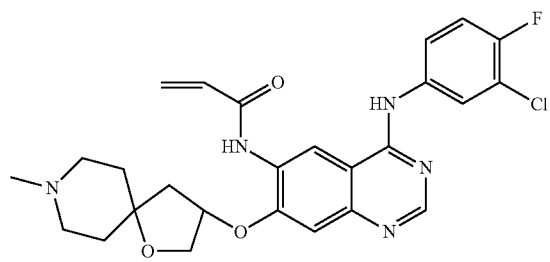

(1) Preparation of N-(4-(3-chloro-4-fluorophenyl))-7-(8-methyl-1-oxa-8-azaspiro[4.5]decan-3-yloxy)-6-nitroquinazolin-4-amine

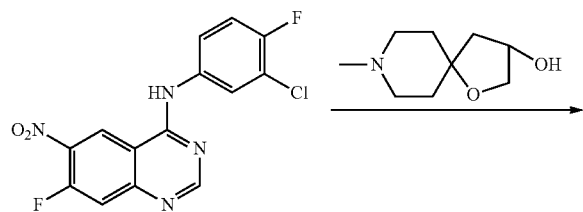

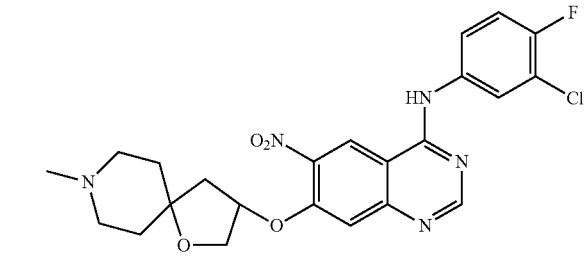

8-methyl-1-oxa-8-azaspiro[4.5]decan-3-ol (0.4 g, 2.5 mmol) was dissolved in DMF (60 mL). 60% sodium hydride (0.4 g, 10 mmol) was added in batch in an ice bath under an atmosphere of $N_2$. The mixture was moved to an atmosphere of room temperature and stirred for 1 h. N-(4-(3-chloro-4-fluorophenyl))-7-fluoro-6-nitroquinazolin-4-amine (1.12 g, 3.3 mmol) was added. The mixture was stirred at 50° C. overnight. After the completion of reaction, water (50 mL) was added. The mixture was extracted with EA. The organic layer was rotary-evaporated to dryness under a reduced pressure to produce N-(4-(3-chloro-4-fluorophenyl))-7-(8-methyl-1-oxa-8-azaspiro[4.5]decan-3-yloxy)-6-nitroquinazolin-4-amine (1.0 g) in a yield of 82%.

(2) Preparation of N-(4-(3-chloro-4-fluorophenyl))-7-(8-methyl-1-oxa-8-azaspiro[4.5]decan-3-yloxy)quinazolin-4,6-diamine

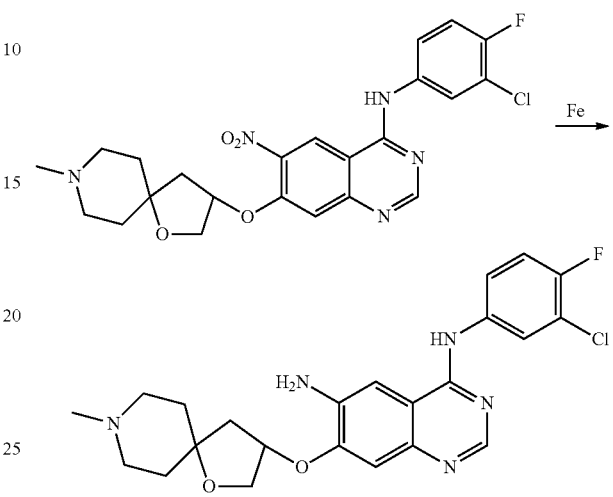

N-(4-(3-chloro-4-fluorophenyl))-7-(8-methyl-1-oxa-8-azaspiro[4.5]decan-3-yloxy)-6-nitroquinazolin-4-amine (1.0 g, 2.05 mmol) was dissolved in a mixed solvent (80 mL) of acetic acid and ethanol (CH$_3$COOH/EtOH=1/3). To the mixture was added Fe powder (1.5 g, 26 mmol). The mixture was warm up to 70° C. and stirred for 1 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduced pressure to produce N-(4-(3-chloro-4-fluorophenyl))-7-(8-methyl-1-oxa-8-azaspiro[4.5]decan-3-yloxy)quinazolin-4,6-diamine (400 mg) in a yield of 43%.

(3) Preparation of N-[4-(3-chloro-4-fluorophenylamino)-7-(8-methyl-1-oxa-8-azaspiro[4.5]decan-3-yloxy)quinazolin-6-yl]-acrylamide

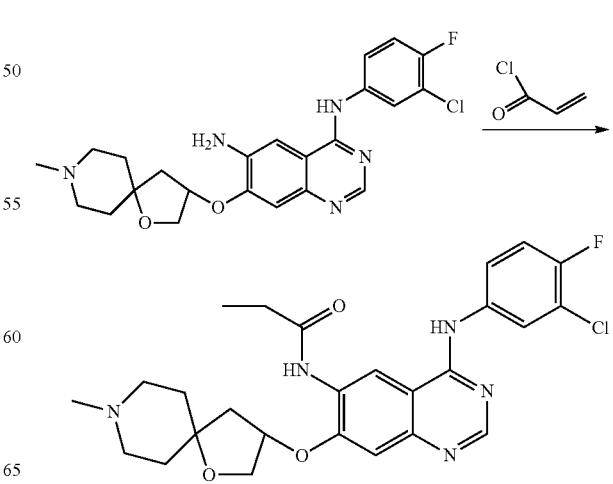

N-(4-(3-chloro-4-fluorophenyl))-7-(8-methyl-1-oxa-8-azaspiro[4.5]decan-3-yloxy)quinazolin-4,6-diamine (400 mg, 0.9 mmol) was dissolved in DCM (20 mL). To the resulting mixture were added triethylamine (0.3 mL) and acryloyl chloride (81 mg, 0.9 mmol). The mixture was stirred at room temperature for 30 min. After the completion of reaction, water (50 mL) was added. The mixture was extracted with EA. The organic layer was rotary-evaporated to dryness under a reduced pressure. The residue was purified by a silica gel column chromatography (eluted with dichloromethane/methanol=5/1) to produce N-[4-(3-chloro-4-fluorophenylamino)-7-(8-methyl-1-oxa-8-azaspiro[4.5]decan-3-yloxy)quinazolin-6-yl]-acrylamide (100 mg) in a yield of 22%.

Molecular formula: $C_{26}H_{27}ClFN_5O_3$

Mass spectrum (m/e): 512.2 (M+1), 256.6 (M/2)

$^1$HNMR: (400 MHz, CDCl$_3$) δ9.15 (s, 1H), 8.64 (s, 1H), 7.98 (s, 1H), 7.96 (d, 1H), 7.55 (m, 2H), 7.16 (t, 1H), 7.12 (s, 1H), 6.50 (d, 1H), 6.35 (m, 1H), 5.92 (d, 1H), 5.20 (m, 1H), 4.23 (m, 2H), 3.07 (m, 1H), 2.96 (m, 2H), 2.64 (s, 3H), 2.38 (m, 4H), 2.04 (d, 1H), 1.84 (d, 1H), 1.44 (t, 1H).

Example 6 Preparation of N-[4-(3-chloro-4-fluorophenylamino)-7-((8-methyl-1-oxa-8-azaspiro[4.5]decan-3-yl)methoxy)quinazolin-6-yl]-acrylamide (Compound 6)

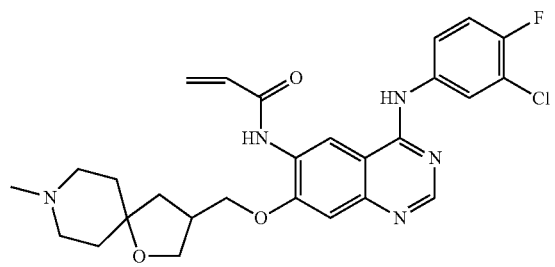 [SMILES: C=CC(=O)Nc1cc2c(Nc3ccc(F)c(Cl)c3)ncnc2cc1OCC1COC2(CCN(C)CC2)C1]

(1) Preparation of N-(4-(3-chloro-4-fluorophenyl))-7-((8-methyl-1-oxa-8-azaspiro[4.5]decan-3-yl)methoxy)-6-nitroquinazolin-4-amine

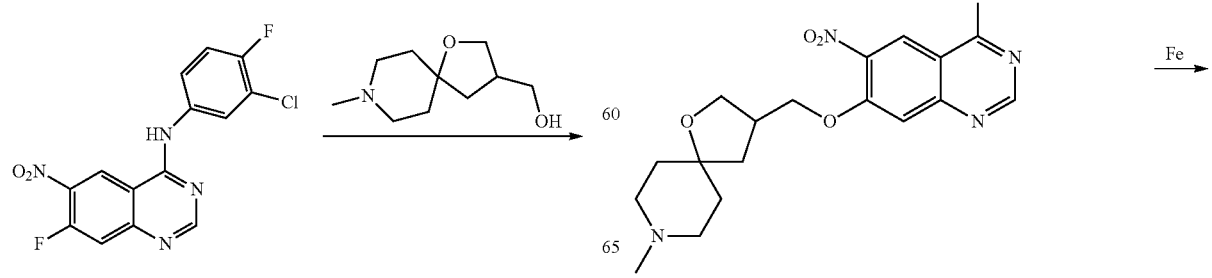

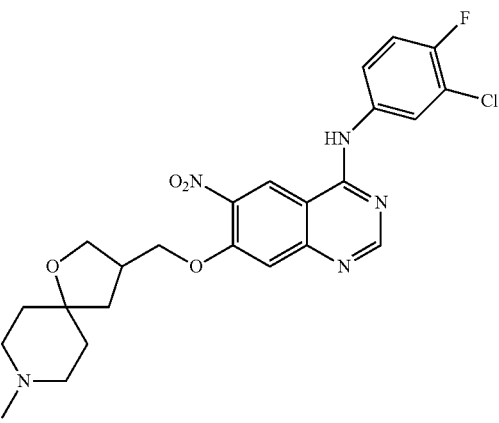

(8-methyl-1-oxa-8-azaspiro[4.5]decan-3-yl)methanol (300 mg, 1.08 mmol) was dissolved in DMF (20 mL). 60% sodium hydride (97 mg, 2.43 mmol) was added in batch in an ice bath under an atmosphere of N2. The mixture was moved to an atmosphere of room temperature and stirred for 1 h. N-(4-(3-chloro-4-fluorophenyl))-7-fluoro-6-nitroquinazolin-4-amine (362 mg, 1.08 mmol) was added. The mixture was stirred at 50° C. overnight. After the completion of reaction, a large quantity of water was added. The mixture was filtered, and the filtered cake was dried in vacuum to produce N-(4-(3-chloro-4-fluorophenyl))-7-((8-methyl-1-oxa-8-azaspiro[4.5]decan-3-yl)methoxy)-6-nitroquinazolin-4-amine (516 mg) in a yield of 95%.

(2) Preparation of N-(4-(3-chloro-4-fluorophenyl))-7-((8-methyl-1-oxa-8-azaspiro[4.5]decan-3-yl)methoxy)quinazolin-4,6-diamine

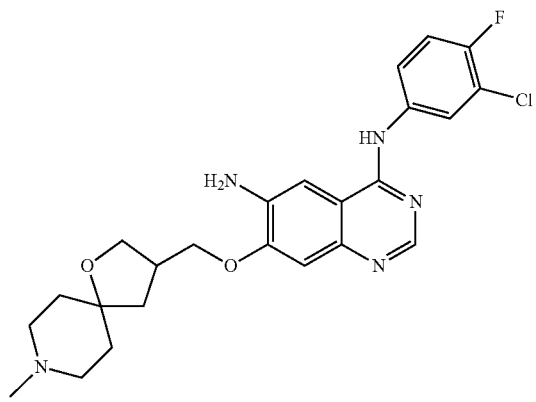

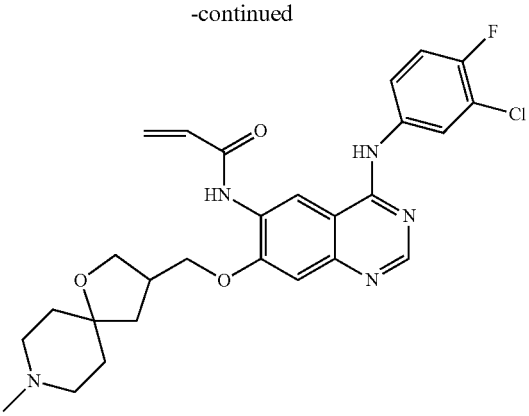

N-(4-(3-chloro-4-fluorophenyl))-7-((8-methyl-1-oxa-8-azaspiro[4.5]decan-3-yl)methoxy)-6-nitroquinazolin-4-amine (516 mg, 1.03 mmol) was dissolved in a mixed solvent (60 mL) of acetic acid and ethanol (CH₃COOH/EtOH=1/3). To the mixture was added Fe powder (346 mg, 6.18 mmol). The mixture was stirred at room temperature for 12 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was concentrated, and the resulting residue was purified by a silica gel column chromatography (eluted with dichloromethane/methanol=10/1) to produce N-(4-(3-chloro-4-fluorophenyl))-7-((8-methyl-1-oxa-8-azaspiro[4.5]decan-3-yl)methoxy)quinazolin-4,6-diamine (100 mg) in a yield of 21%.

(3) Preparation of N-[4-(3-chloro-4-fluorophenylamino)-7-((8-methyl-1-oxa-8-azaspiro[4.5]decan-3-yl)methoxy)quinazolin-6-yl]-acrylamide In a reaction flask, N-(4-(3-chloro-4-fluorophenyl))-7-((8-methyl-1-oxa-8-azaspiro[4.5]decan-3-yl)methoxy)quinazolin-4,6-diamine (100 mg, 0.21 mmol) was dissolved in dichloromethane (10 mL). The mixture was cooled down to 0° C. Triethylamine (42 mg, 0.42 mmol) was added to the reaction flask. Acryloyl chloride (17 mg, 0.19 mmol) was dissolved in DCM (1 mL). The resulting solution was slowly added to the reaction flask. The mixture was reacted at room temperature for 30 min. The reaction was washed with distilled water (10 mL) triple, and distillated at a reduced pressure to remove dichloromethane to produce a crude yellow powdery product, which was purified by a silica gel column chromatography (eluted with DCM/MeOH=15/1) to produce a pale-yellow powdery solid N-[4-(3-chloro-4-fluorophenylamino)-7-((8-methyl-1-oxa-8-azaspiro[4.5]decan-3-yl)methoxy)quinazolin-6-yl]-acrylamide (15 mg) in a yield of 14%.

Molecular formula: $C_{27}H_{29}ClFN_5O_3$

Mass spectrum (m/e): 526.2 (M+1), 263.6 (M/2)

¹HNMR: (400 MHz, CDCl₃) δ9.10 (s, 1H), 8.63 (s, 1H), 8.32 (s, 1H), 7.86 (d, 1H), 7.74 (s, 1H), 7.48 (d, 1H), 7.15 (s, 1H), 7.10 (m, 1H), 6.48 (d, 1H), 6.38 (m, 1H), 5.86 (d, 1H), 4.18 (t, 2H), 4.08 (t, 1H), 3.87 (t, 1H), 2.91 (s, H), 2.60 (m, 4H), 2.36 (m, 3H), 2.13 (t, 1H), 1.80-2.11 (m, 4H), 1.60 (m, 1H).

Example 7 Preparation of N-[4-(3-chloro-4-fluorophenylamino)-7-(8-methyl-1-oxa-8-azaspiro[4.5]decan-2-ylmethoxy)quinazolin-6-yl]-acrylamide (Compound 7)

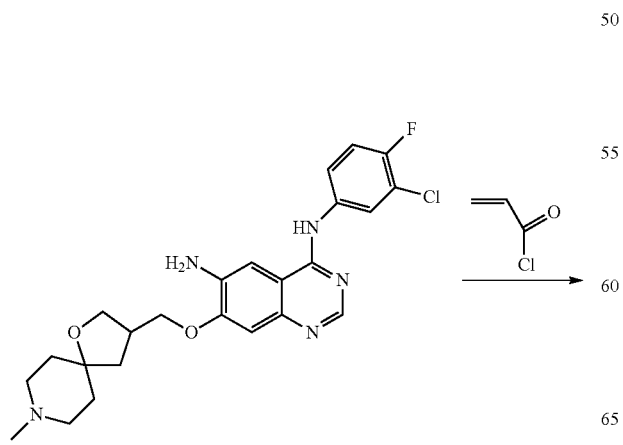

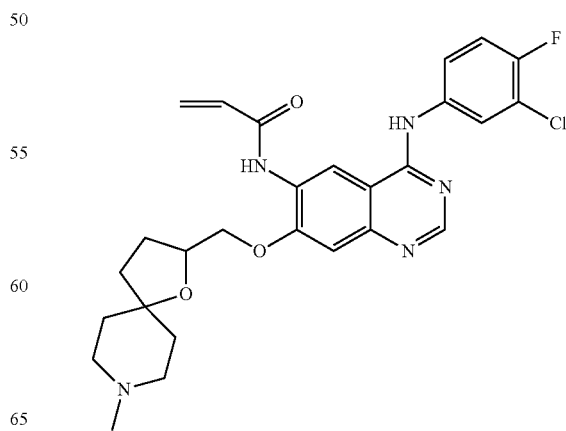

(1) Preparation of N-(4-(3-chloro-4-fluorophenyl))-7-(8-methyl-1-oxa-8-azaspiro[4.5]decan-2-yl-methoxy)-6-nitroquinazolin-4-amine

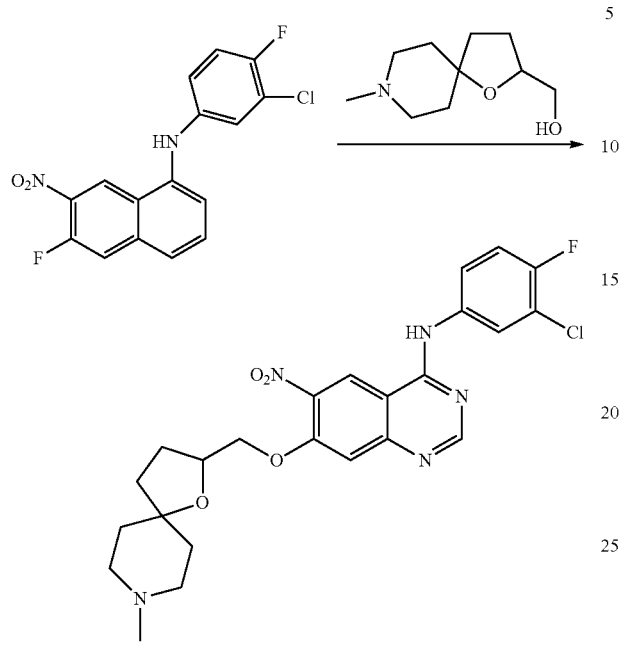

8-methyl-1-oxa-8-azaspiro[4.5]decan-2-ylmethanol (280 mg, 1.5 mmol) was dissolved in DMF (20 mL). 60% sodium hydride (1.1 g, 27 mmol) was added in batch in an ice bath under an atmosphere of $N_2$. The mixture was moved to an atmosphere of room temperature and stirred for 1 h. N-(4-(3-chloro-4-fluorophenyl))-7-fluoro-6-nitroquinazolin-4-amine (508 mg, 1.5 mmol) was added. The mixture was stirred at 50° C. overnight. After the completion of reaction, water (50 mL) was added. The mixture was extracted with EA. The organic layer was rotary-evaporated to dryness under a reduced pressure to produce N-(4-(3-chloro-4-fluorophenyl))-7-(8-methyl-1-oxa-8-azaspiro[4.5]decan-2-ylmethoxy)-6-nitroquinazolin-4-amine (380 mg) in a yield of 50%.

(2) Preparation of N-(4-(3-chloro-4-fluorophenyl))-7-(8-methyl-1-oxa-8-azaspiro[4.5]decan-2-ylmethoxy)quinazolin-4,6-diamine

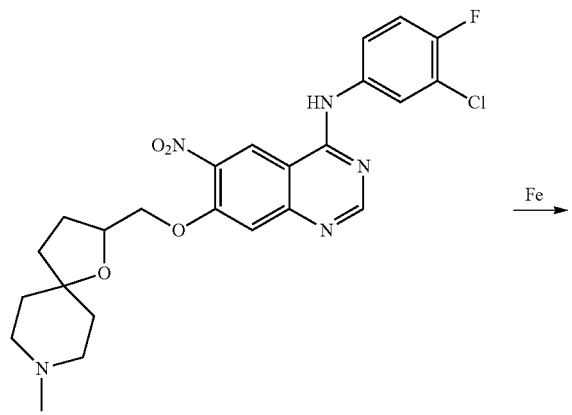

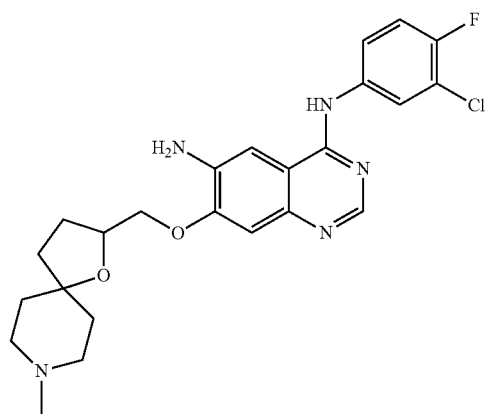

N-(4-(3-chloro-4-fluorophenyl))-7-(8-methyl-1-oxa-8-azaspiro[4.5]decan-2-ylmethoxy)-6-nitroquinazolin-4-amine (380 mg, 0.76 mmol) was dissolved in a mixed solvent (8 mL) of acetic acid and ethanol (CH₃COOH/EtOH=1/3). To the mixture was added Fe powder (343 mg, 6.12 mmol). The mixture was warm up to 70° C. and stirred for 1 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduce pressure. The resulting residue was purified by a silica gel column chromatography (eluted with dichloromethane/methanol=15/1) to produce N-(4-(3-chloro-4-fluorophenyl))-7-(8-methyl-1-oxa-8-azaspiro[4.5]decan-2-ylmethoxy)quinazolin-4,6-diamine (180 mg) in a yield of 50%.

(3) Preparation of N-[4-(3-chloro-4-fluorophenylamino)-7-(8-methyl-1-oxa-8-azaspiro[4.5]decan-2-ylmethoxy) quinazolin-6-yl]-acrylamide

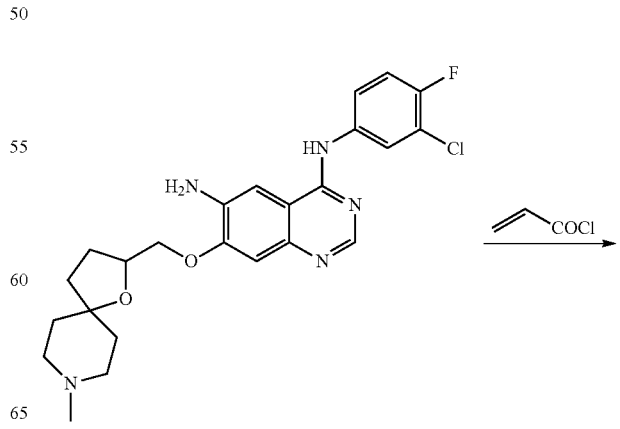

55
-continued

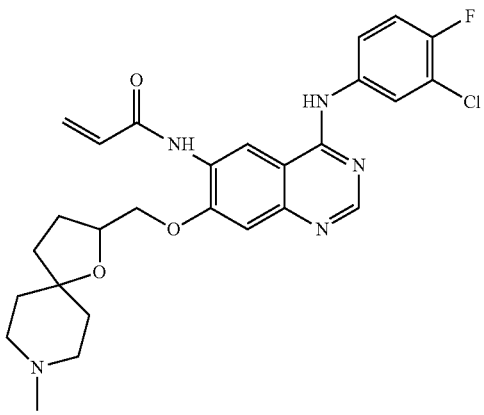

N-(4-(3-chloro-4-fluorophenyl))-7-(8-methyl-1-oxa-8-azaspiro[4.5]decan-2-ylmethoxy)quinazolin-4,6-diamine (175 mg, 0.38 mmol) was dissolved in dichloromethane (30 mL). Triethylamine (77 mg) was added. Acryloyl chloride (31 mg, 0.34 mmol) was added dropwise under an ice bath. The mixture was stirred at room temperature for 0.5 h. After the completion of reaction, water (50 mL) was added. The mixture was extracted with EA. The organic layer was rotary-evaporated to dryness under a reduced pressure. The resulting residue was purified by a silica gel column chromatography (eluted with dichloromethane/methanol=20/1) to produce N-[4-(3-chloro-4-fluorophenylamino)-7-(8-methyl-1-oxa-8-azaspiro[4.5]decan-2-ylmethoxy) quinazolin-6-yl]-acrylamide (14 mg) in a yield of 8%.

Molecular formula: $C_{27}H_{29}ClFN_5O_3$

Mass spectrum (m/e): 526.2 (M+1), 263.7 (M/2)

$^1$HNMR (400 MHz, CDCl$_3$) δ8.92 (s, 1H), 8.55 (s, 1H), 7.98 (d, 1H), 7.62 (d, 1H), 7.20 (s, 1H), 7.13 (t, 1H), 6.47 (d, 2H), 5.86 (d, 1H), 4.47 (m, 1H), 4.24 (d, 1H), 4.10 (t, 1H), 3.05 (m, 4H), 2.49 (s, 3H), 1.78-1.97 (m, 8H).

Example 8 Preparation of N-[4-(3-chloro-4-fluorophenylamino)-7-(2-((1R,5S,6S)-3-methyl-3-azabicyclo[3.1.0]hexan-6-ylethoxy)quinazolin-6-yl]-acrylamide (Compound 8)

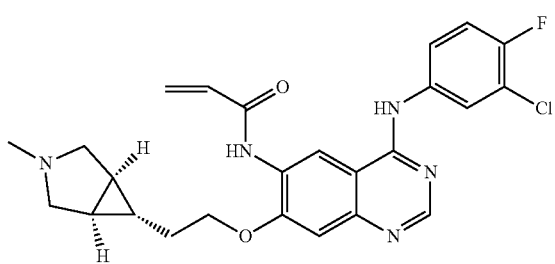 [SMILES: C=CC(=O)Nc1cc2c(Nc3ccc(F)c(Cl)c3)ncnc2cc1OCC[C@@H]1[C@H]2CN(C)C[C@@H]12]

56

(1) Preparation of N-(4-(3-chloro-4-fluorophenyl))-7-(2-((1R,5S,6S)-3-methyl-3-azabicyclo[3.1.0]hexan-6-ylethoxy)-6-nitroquinazolin-4-amine

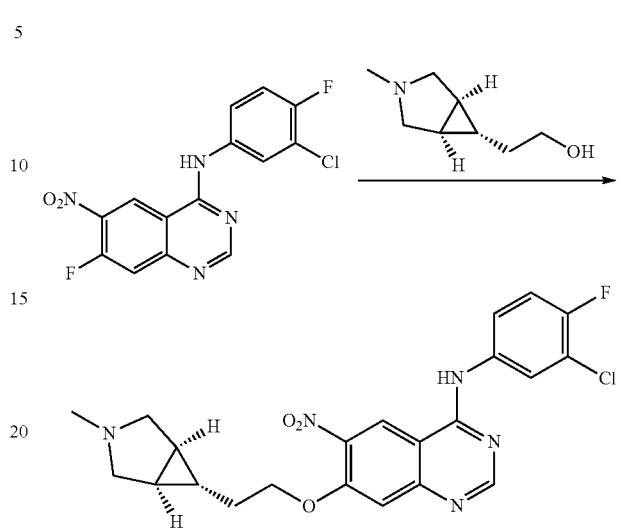

2-((1R,5S,6S)-3-methyl-3-azabicyclo[3.1.0]hexan-6-ylethanol (0.2 g, 1.4 mmol) was dissolved DMF (10 mL). 60% sodium hydride (1.12 g, 2.8 mmol) was added in batch in an ice bath under an atmosphere of N$_2$. The mixture was moved to an atmosphere of room temperature and stirred for 30 min. N-(4-(3-chloro-4-fluorophenyl))-7-fluoro-6-nitroquinazolin-4-amine (470 mg, 1.4 mmol) was added. The mixture was stirred at 50° C. overnight. After the completion of reaction, water (50 mL) was added. The mixture was extracted with EA. The organic layer was rotary-evaporated to dryness under a reduced pressure to produce N-(4-(3-chloro-4-fluorophenyl))-7-2-((1R,5S,6S)-3-methyl-3-azabicyclo[3.1.0]hexan-6-ylethoxy)-6-nitroquinazolin-4-amine (500 mg) in a yield of 78%.

(2) Preparation of N-(4-(3-chloro-4-fluorophenyl))-7-2-((1R,5S,6S)-3-methyl-3-azabicyclo[3.1.0]hexan-6-ylethoxy)quinazolin-4,6-diamine

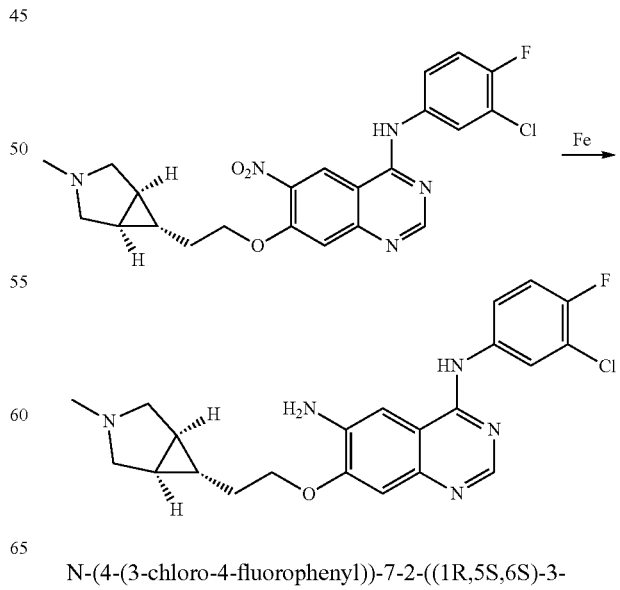

N-(4-(3-chloro-4-fluorophenyl))-7-2-((1R,5S,6S)-3-methyl-3-azabicyclo[3.1.0]hexan-6-ylethoxy)-6-nitroquinazolin-4-amine (500 mg, 1.1 mmol) was dissolved in a mixed solvent of EtOH (10 mL) and CH₃COOH (3 mL). To the mixture was added Fe powder (343 mg, 6.12 mmol). The reaction was conducted at room temperature 12 h under stirring. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduced pressure. The resulting residue was purified by a silica gel column chromatography (eluted with dichloromethane/methanol=10/1) to produce N-(4-(3-chloro-4-fluorophenyl))-7-(2-((1R,5S,6S)-3-methyl-3-azabicyclo[3.1.0]hexan-6-ylethoxy)quinazolin-4,6-diamine (200 mg) in a yield of 43%.

(3) Preparation of N-[4-(3-chloro-4-fluorophenylamino)-7-(2-((1R,5S,6S)-3-methyl-3-azabicyclo[3.1.0]hexan-6-ylethoxy)quinazolin-6-yl]-acrylamide

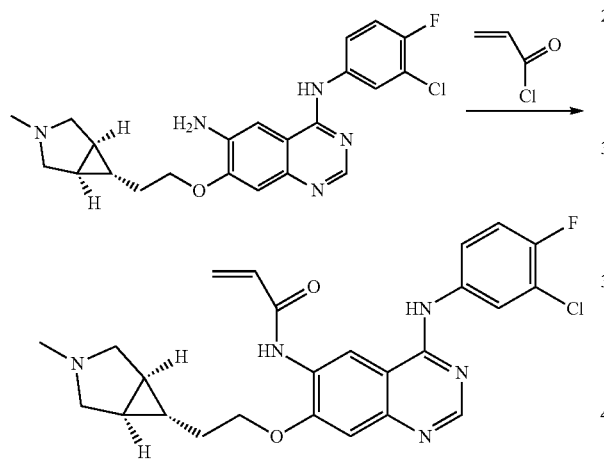

N-(4-(3-chloro-4-fluorophenyl))-7-(2-((1R,5S,6S)-3-methyl-3-azabicyclo[3.1.0]hexan-6-ylethoxy)quinazolin-4,6-diamine (200 mg, 0.47 mmol) was dissolved in dichloromethane (20 mL). Triethylamine (200 mg) and acryloyl chloride (43 mg, 0.47 mmol) were added under an ice bath. The mixture was stirred at room temperature for 30 min. After the completion of reaction, water (50 mL) was added. The mixture was extracted with EA. The organic layer was rotary-evaporated to dryness under a reduced pressure. The resulting residue was purified by a silica gel column chromatography (eluted with dichloromethane/methanol=5/1) to produce N-[4-(3-chloro-4-fluorophenylamino)-7-(2-((1R,5S,6S)-3-methyl-3-azabicyclo[3.1.0]hexan-6-ylethoxy)quinazolin-6-yl]-acrylamide 40 mg) in a yield of 18%.

Molecular formula: $C_{25}H_{25}ClFN_5O_2$

Mass spectrum (m/e): 482.2 (M+1), 241.6 (M/2)

¹HNMR (400 MHz, CDCl₃) δ9.15 (s, 1H), 8.94 (s, 1H), 8.60 (s, 1H), 7.89 (s, 1H), 7.83 (d, 1H), 7.58 (d, 1H), 7.22 (t, 1H), 7.05 (m, 1H), 6.49 (d, 1H), 5.86 (d, 1H), 4.38 (t, 2H), 3.78 (d, 2H), 3.10 (d, 2H), 2.80 (s, 3H), 2.39 (m, 1H), 1.83 (m, 2H), 1.74 (m, 2H).

Example 9 Preparation of N-[4-(3-chloro-4-fluorophenylamino)-7-((2-methyloctahydrocyclopenta[c]pyrrol-4-yl)methoxy)quinazolin-6-yl]-acrylamide (Compound 9)

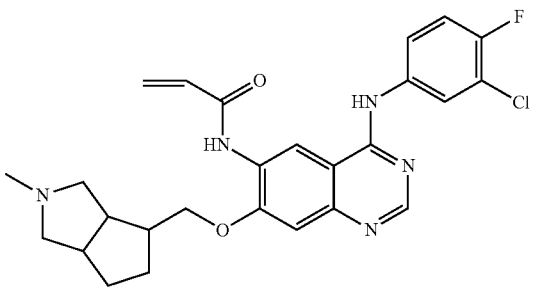 [SMILES: C=CC(=O)Nc1cc2c(Nc3ccc(F)c(Cl)c3)ncnc2cc1OCC1CCC2CN(C)CC12]

(1) Preparation of N-(4-(3-chloro-4-fluorophenyl))-7-((2-methyloctahydrocyclopenta[c]pyrrol-4-yl)methoxy)-6-nitroquinazolin-4-amine (2-methyloctahydrocyclopenta[c]pyrrol-4-yl)methanol (380 mg, 2.45 mmol) was dissolved in DMF (20 mL). 60% sodium hydride (1.6 g, 40 mmol) was added in batch in an ice bath under an atmosphere of N₂. The mixture was moved to an atmosphere of room temperature and stirred for 1 h. N-(4-(3-chloro-4-fluorophenyl))-7-fluoro-6-nitroquinazolin-4-amine (1.08 g, 3.2 mmol) was added. The mixture was stirred at 50° C. overnight. After the completion of reaction, water (50 mL) was added. The mixture was extracted with EA. The organic layer was rotary-evaporated to dryness under a reduced pressure to produce N-(4-(3-chloro-4-fluorophenyl))-7-((2-methyloctahydrocyclopenta[c]pyrrol-4-yl)methoxy)-6-nitroquinazolin-4-amine (318 mg) in a yield of 28%.

(2) N-(4-(3-chloro-4-fluorophenyl))-7-((2-methyloctahydrocyclopenta[c]pyrrol-4-yl)methoxy)quinazolin-4,6-diamine

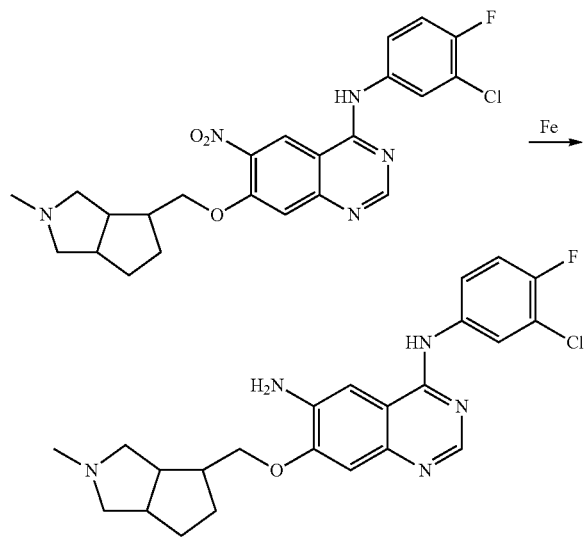

N-(4-(3-chloro-4-fluorophenyl))-7-((2-methyloctahydrocyclopenta[c]pyrrol-4-yl)methoxy)-6-nitroquinazolin-4-amine (318 mg, 0.68 mmol) was dissolved in a mixed solvent (8 mL) of acetic acid and ethanol (CH₃COOH/EtOH=1/3). To the mixture was added Fe powder (200 mg, 3.57 mmol). The mixture was warmed up to 70° C. and stirred for 1.5 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduce pressure. The residue was purified by a silica gel column chromatography (eluted with dichloromethane/methanol=15/1) to produce N-(4-(3-chloro-4-fluorophenyl))-7-((2-methyloctahydrocyclopenta[c]pyrrol-4-yl)methoxy)quinazolin-4,6-diamine (90 mg) in a yield of 30%.

(3) Preparation of N-[4-(3-chloro-4-fluorophenylamino)-7-((2-methyloctahydrocyclopenta[c]pyrrol-4-yl)methoxy)quinazolin-6-yl]-acrylamide

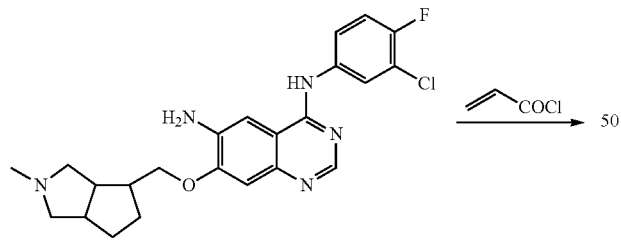

N-(4-(3-chloro-4-fluorophenyl))-7-((2-methyloctahydrocyclopenta[c]pyrrol-4-yl)methoxy)quinazolin-4,6-diamine (80 mg, 0.18 mmol) was dissolved in dichloromethane (30 mL). Triethylamine (40 mg) was added. Acryloyl chloride (16 mg, 0.18 mmol) was added dropwise under an ice bath. The mixture was stirred at room temperature for 0.5 h. After the completion of reaction, water (50 mL) was added. The mixture was extracted with EA. The organic layer was rotary-evaporated to dryness under a reduced pressure. The resulting residue was purified by a silica gel column chromatography (eluted with dichloromethane/methanol=20/1) to produce N-[4-(3-chloro-4-fluorophenylamino)-7-((2-methyloctahydrocyclopenta[c]pyrrol-4-yl)methoxy)-acrylamide 20 mg) in a yield of 22%.

Molecular formula: $C_{26}H_{27}ClFN_5O_2$

Mass spectrum (m/e): 496.3 (M+1), 248.7 (M/2)

¹HNMR (400 MHz, CDCl₃) δ8.79 (s, 1H), 8.56 (s, 1H), 7.96 (d, 1H), 7.61 (d, 1H), 7.29 (s, 1H), 7.15 (m, 1H), 6.70 (m, 1H), 6.51 (d, 1H), 5.85 (d, 1H), 4.18 (m, 1H), 4.10 (m, 1H), 3.41-3.95 (m, 2H), 3.38 (d, 1H), 3.03-3.12 (m, 4H), 2.82 (s, 3H), 2.15 (s, 3H), 1.22 (m, 3H).

Example 10 Preparation of N-[4-(3-chloro-4-fluorophenylamino)-7-((7-methyl-7-azabicyclo[2.2.1]heptan-2-yl)methoxy) quinazolin-6-yl]-acrylamide (Compound 10)

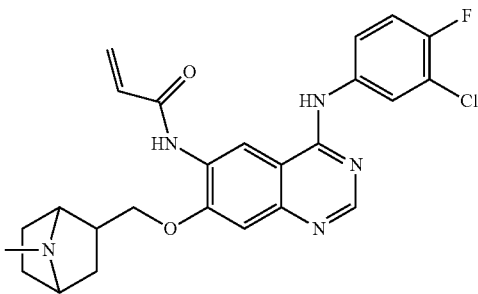 [SMILES: C=CC(=O)Nc1cc2c(Nc3ccc(F)c(Cl)c3)ncnc2cc1OCC1CC2CCC1N2C]

(1) Preparation of N-(4-(3-chloro-4-fluorophenyl))-7-((7-methyl-7-azabicyclo[2.2.1]heptan-2-yl)methoxy)-6-nitroquinazolin-4-amine

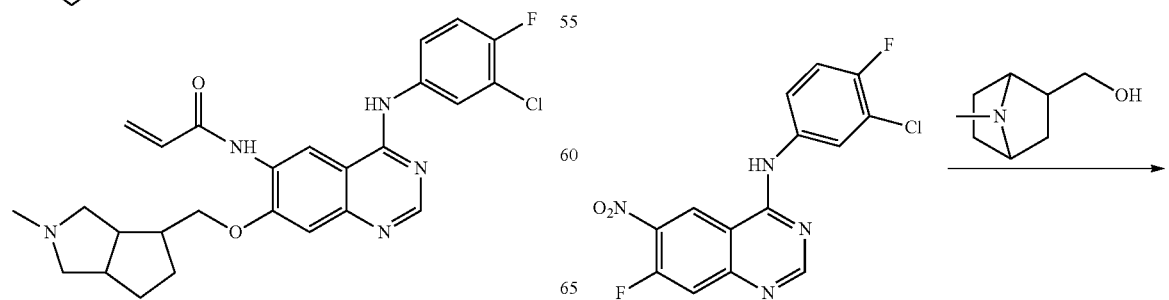

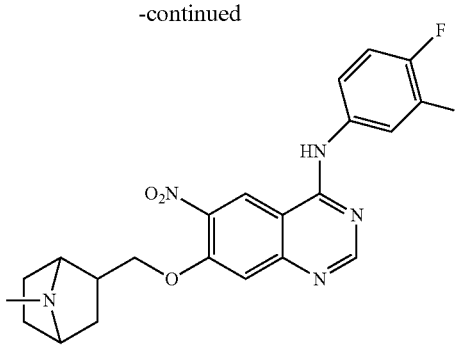

(7-methyl-7-azabicyclo[2.2.1]heptan-2-yl)methanol (283 mg, 2.0 mmol) was dissolved in DMF (10 mL). 60% sodium hydride (160 g, 4.0 mmol) was added in batch in an ice bath under an atmosphere of N2. The mixture was moved to an atmosphere of room temperature and stirred for 1 h. N-(4-(3-chloro-4-fluorophenyl))-7-fluoro-6-nitroquinazolin-4-amine (1.13 g, 3.0 mmol) was added. The mixture was stirred at 50° C. overnight. After the completion of reaction, water (50 mL) was added. The mixture was extracted with EA. The organic layer was rotary-evaporated to dryness under a reduced pressure. The resulting residue was purified by a silica gel column chromatography (eluted with dichloromethane/methanol=8/1) to produce N-(4-(3-chloro-4-fluorophenyl))-7-((7-methyl-7-azabicyclo[2.2.1]heptan-2-yl)methoxy)-6-nitroquinazolin-4-amine (427 mg) in a yield of 47%.

(2) Preparation of N-(4-(3-chloro-4-fluorophenyl))-7-((7-methyl-7-azabicyclo[2.2.1]heptan-2-yl)methoxy)quinazolin-4,6-diamine

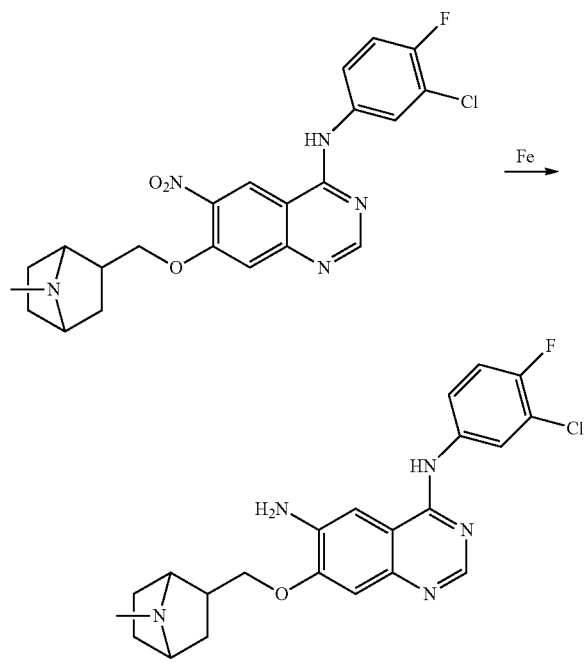

N-(4-(3-chloro-4-fluorophenyl))-7-((7-methyl-7-azabicyclo[2.2.1]heptan-2-yl)methoxy)-6-nitroquinazolin-4-amine (427 mg, 0.93 mmol) was dissolved in a mixed solvent (28 mL) of acetic acid and ethanol (CH$_3$COOH/EtOH=1/3). To the mixture was added Fe powder (312 mg, 5.58 mmol). The mixture was warm up to 70° C. and stirred for 1 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduced pressure to produce N-(4-(3-chloro-4-fluorophenyl))-7-((7-methyl-7-azabicyclo[2.2.1]heptan-2-yl)methoxy)quinazolin-4,6-diamine (157 mg) in a yield of 40%.

(3) Preparation of N-[4-(3-chloro-4-fluorophenylamino)-7-((7-methyl-7-azabicyclo[2.2.1]heptan-2-yl)methoxy) quinazolin-6-yl]-acrylamide

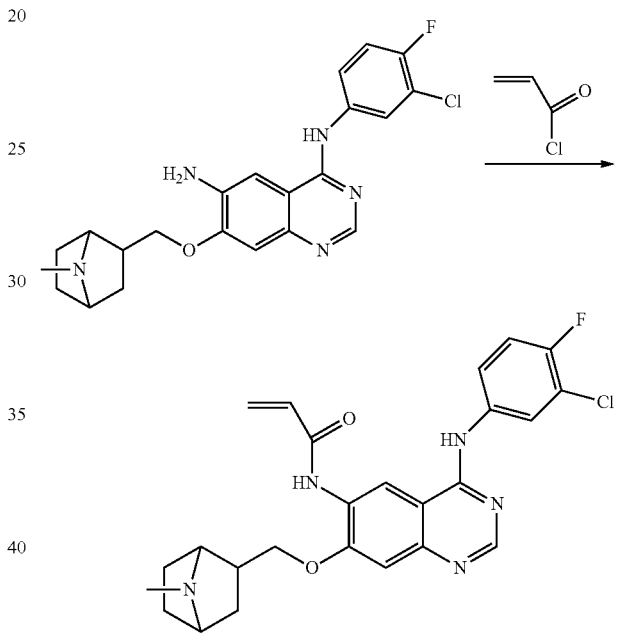

N-(4-(3-chloro-4-fluorophenyl))-7-((7-methyl-7-azabicyclo[2.2.1]heptan-2-yl)methoxy)quinazolin-4,6-diamine (157 mg, 0.37 mmol) was dissolved in dichloromethane (10 mL). Triethylamine (111 mg, 1.10 mmol) and acryloyl chloride (33 mg, 0.37 mmol) were added under an ice bath. The mixture was stirred at room temperature overnight. After the completion of reaction, water (50 mL) was added. The mixture was extracted with EA. The organic layer was rotary-evaporated to dryness under a reduced pressure. The resulting residue was purified by a silica gel column chromatography (eluted with dichloromethane/methanol=15/1) to produce N-[4-(3-chloro-4-fluorophenylamino)-7-((7-methyl-7-azabicyclo[2.2.1]heptan-2-yl)methoxy) quinazolin-6-yl]-acrylamide 20 mg) in a yield of 11%.

Molecular formula: $C_{25}H_{25}ClFN_5O_2$

Mass spectrum (m/e): 482.2 (M+1), 241.7 (M/2)

$^1$HNMR (400 MHz, CDCl$_3$) δ9.08 (s, 1H), 8.64 (s, 1H), 8.16 (s, 1H), 7.88 (m, 2H), 7.51 (d, 1H), 7.24 (s, 1H), 7.10 (t, 1H), 6.48 (d, 1H), 6.38 (m, 1H), 5.88 (d, 1H), 4.22 (m, 1H), 4.10 (t, 1H), 3.56 (s, 1H), 3.44 (s, 1H), 2.94 (m, 1H), 2.46 (s, 3H), 2.25 (m, 1H), 1.99 (m, 1H), 1.70 (m, 1H), 1.68 (m, 1H), 1.41 (m, 1H), 1.05 (m, 1H).

Example 11 Preparation of N-[4-(3-chloro-4-fluorophenylamino)-7-(2-(3-methyl-3-azabicyclo[3.2.1]octan-8-yl)ethoxy)quinazolin-6-yl]-acrylamide (Compound 11)

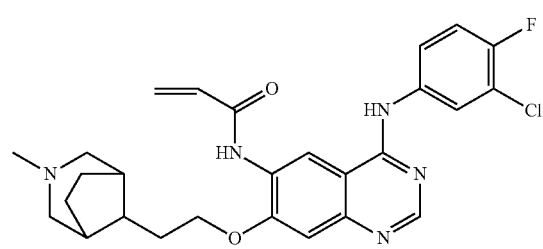 [SMILES: C=CC(=O)Nc1cc2c(Nc3ccc(F)c(Cl)c3)ncnc2cc1OCCC1C2CCC1CN(C)C2]

(1) Preparation of N-(4-(3-chloro-4-fluorophenyl))-7-(2-(3-methyl-3-azabicyclo[3.2.1]octan-8-yl)ethoxy)-6-nitroquinazolin-4-amine

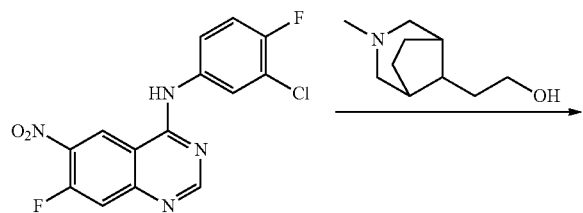

2-(3-methyl-3-azabicyclo[3.2.1]octan-8-yl)ethanol (338 mg, 2 mmol) was dissolved in DMF (20 mL). 60% sodium hydride (0.4 g, 10 mmol) was added in batch in an ice bath under an atmosphere of $N_2$. The mixture was moved to an atmosphere of room temperature and stirred for 1 h. N-(4-(3-chloro-4-fluorophenyl))-7-fluoro-6-nitroquinazolin-4-amine (1.12 g, 3.3 mmol) was added. The mixture was stirred at 50° C. overnight. After the completion of reaction, water (50 mL) was added. The mixture was extracted with EA. The organic layer was rotary-evaporated to dryness under a reduced pressure to produce N-(4-(3-chloro-4-fluorophenyl))-7-(2-(3-methyl-3-azabicyclo[3.2.1]octan-8-yl)ethoxy)-6-nitroquinazolin-4-amine (560 mg) in a yield of 58%.

(2) Preparation of N-(4-(3-chloro-4-fluorophenyl))-7-(2-(3-methyl-3-azabicyclo[3.2.1]octan-8-yl)ethoxy)quinazolin-4,6-diamine

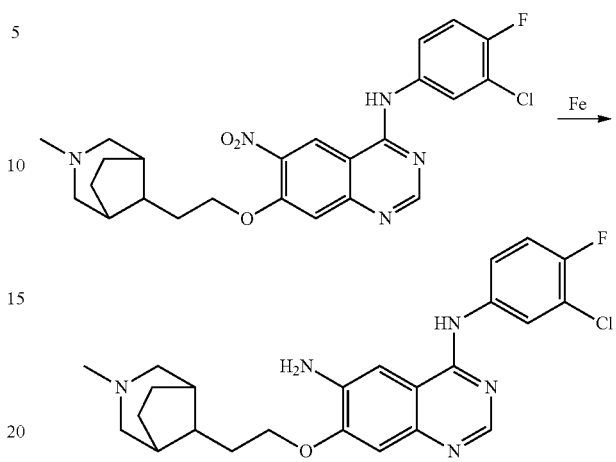

N-(4-(3-chloro-4-fluorophenyl))-7-(2-(3-methyl-3-azabicyclo[3.2.1]octan-8-yl)ethoxy)-6-nitroquinazolin-4-amine (560 mg, 1.15 mmol) was dissolved in a mixed solvent (20 mL) of acetic acid and ethanol ($CH_3COOH/EtOH=1/3$). To the mixture was added Fe powder (343 mg, 6.12 mmol). The mixture was warmed up to 70° C. and stirred for 1 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduced pressure to produce N-(4-(3-chloro-4-fluorophenyl))-7-(2-(3-methyl-3-azabicyclo[3.2.1]octan-8-yl)ethoxy)quinazolin-4,6-diamine (360 mg) in a yield of 69%.

(3) Preparation of N-[4-(3-chloro-4-fluorophenylamino)-7-(2-(3-methyl-3-azabicyclo[3.2.1]octan-8-yl)ethoxy)quinazolin-6-yl]-acrylamide

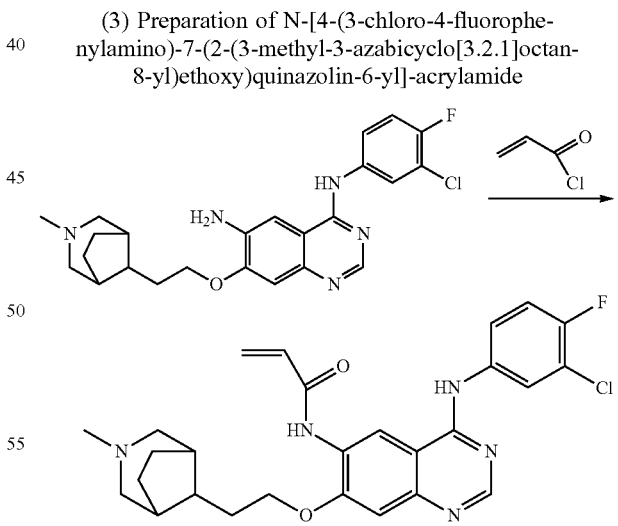

N-(4-(3-chloro-4-fluorophenyl))-7-(2-(3-methyl-3-azabicyclo[3.2.1]octan-8-yl)ethoxy)quinazolin-4,6-diamine (360 mg, 0.79 mmol) and triethylamine (112 mg) were dissolved in dichloromethane (20 mL). Acryloyl chloride (71 mg, 0.79 mmol) was added dropwise. The mixture was stirred at room temperature for 1 h. After the completion of reaction, water (50 mL) was added. The mixture was extracted with EA, and rotary-evaporated to dryness under a reduced pressure. The residue was washed with diethyl ether to produce N-[4-(3- chloro-4-fluorophenylamino)-7-(2-(3-methyl-3-azabicyclo[3.2.1]octan-8-yl)ethoxy)quinazolin-6-yl]-acrylamide (34 mg) in a yield of 8%.

Molecular formula: $C_{27}H_{29}ClFN_5O_2$

Mass spectrum (m/e): 510.3 (M+1), 255.8 (M/2)

$^1$HNMR (400 MHz, CDCl$_3$) δ9.13 (s, 1H), 8.67 (s, 1H), 8.15 (s, 1H), 7.94 (d, 1H), 7.61 (s, 1H), 7.53 (d, 1H), 7.15 (t, 1H), 6.50 (d, 1H), 6.34 (m, 1H), 5.90 (d, 1H), 4.29 (m, 2H), 2.69 (t, 1H), 2.66 (d, 1H), 2.50 (s, 3H), 1.27-2.35 (m, 11H).

Example 12 Preparation of N-[4-(3-chloro-4-fluorophenylamino)-7-((5-methyl-5-azaspiro[2.4]heptan-1-yl)methoxy)quinazolin-6-yl]-acrylamide (Compound 12)

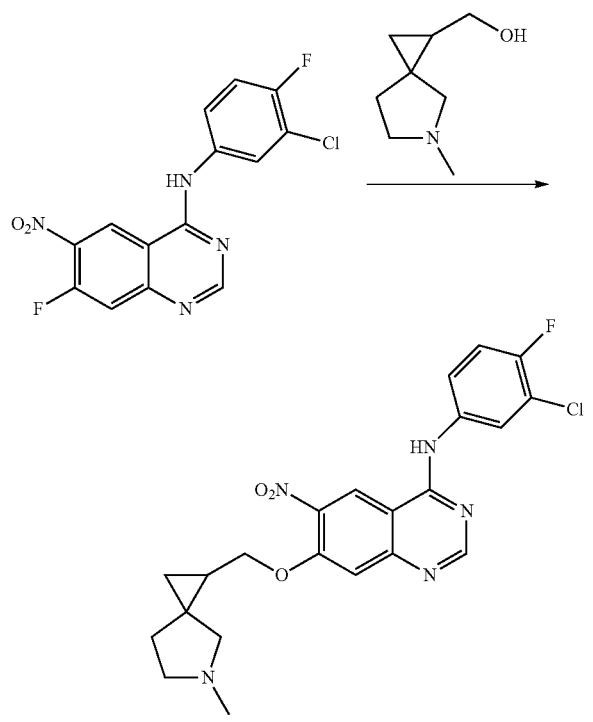

(1) Preparation of N-(4-(3-chloro-4-fluorophenyl))-7-((5-methyl-5-azaspiro[2.4]heptan-1-yl)methoxy)-6-nitroquinazolin-4-amine

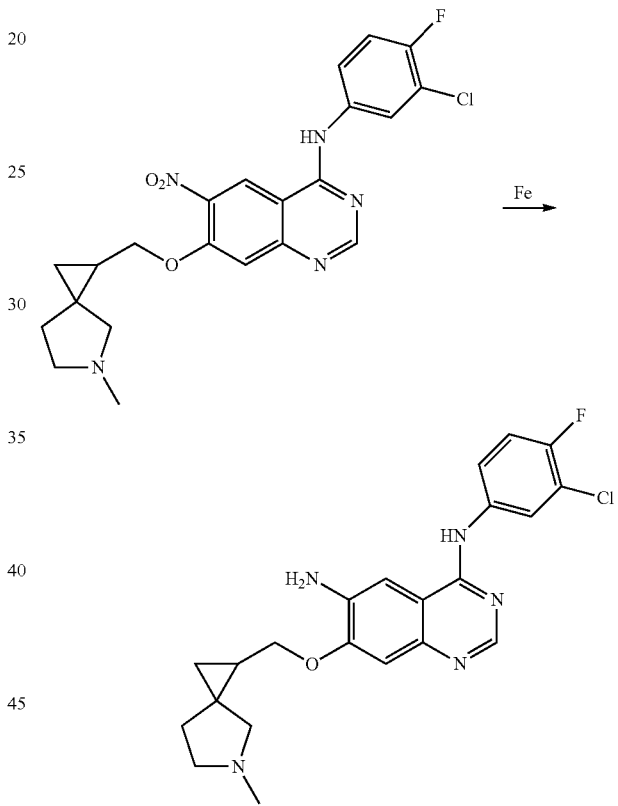

(5-methyl-5-azaspiro[2.4]heptan-1-yl)methanol (370 mg, 2.62 mmol) was dissolved in DMF (20 mL). 60% sodium hydride (157 mg, 3.93 mmol) was added in batch in an ice bath under an atmosphere of N2. The mixture was moved to an atmosphere of room temperature and stirred for 1 h. N-(4-(3-chloro-4-fluorophenyl))-7-fluoro-6-nitroquinazolin-4-amine (588 mg, 1.75 mmol) was added. The mixture was stirred at room temperature overnight. After the completion of reaction, water (20 mL) was added. The mixture was filtered. The filtered cake was dried in vacuum to produce N-(4-(3-chloro-4-fluorophenyl))-7-((5-methyl-5-azaspiro[2.4]heptan-1-yl)methoxy)-6-nitroquinazolin-4-amine (690 mg) in a yield of 86%.

(2) Preparation of N-(4-(3-chloro-4-fluorophenyl))-7-((5-methyl-5-azaspiro[2.4]heptan-1-yl)methoxy)quinazolin-4,6-diamine N-(4-(3-chloro-4-fluorophenyl))-7-((5-methyl-5-azaspiro[2.4]heptan-1-yl)methoxy)-6-nitroquinazolin-4-amine (69 mg, 1.51 mmol) was dissolved in a mixed solvent (60 mL) of acetic acid and ethanol (CH$_3$COOH/EtOH=1/3). To the mixture was added Fe powder (507 mg, 9.06 mmol). The mixture was warm up to 30° C. and stirred for 12 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduce pressure. The resulting residue was purified by a silica gel column chromatography (eluted with dichloromethane/methanol=10/1) to produce N-(4-(3-chloro-4-fluorophenyl))-7-((5-methyl-5-azaspiro[2.4]heptan-1-yl)methoxy)quinazolin-4,6-diamine (100 mg) in a yield of 15%.

(3) Preparation of N-[4-(3-chloro-4-fluorophenylamino)-7-((5-methyl-5-azaspiro[2.4]heptan-1-yl)methoxy)quinazolin-6-yl]-acrylamide

Example 13 Preparation of N-[4-(3-chloro-4-fluorophenylamino)-7-((6-methyl-6-azaspiro[2.5]octan-1-yl)methoxy)quinazolin-6-yl]-acrylamide (Compound 13)

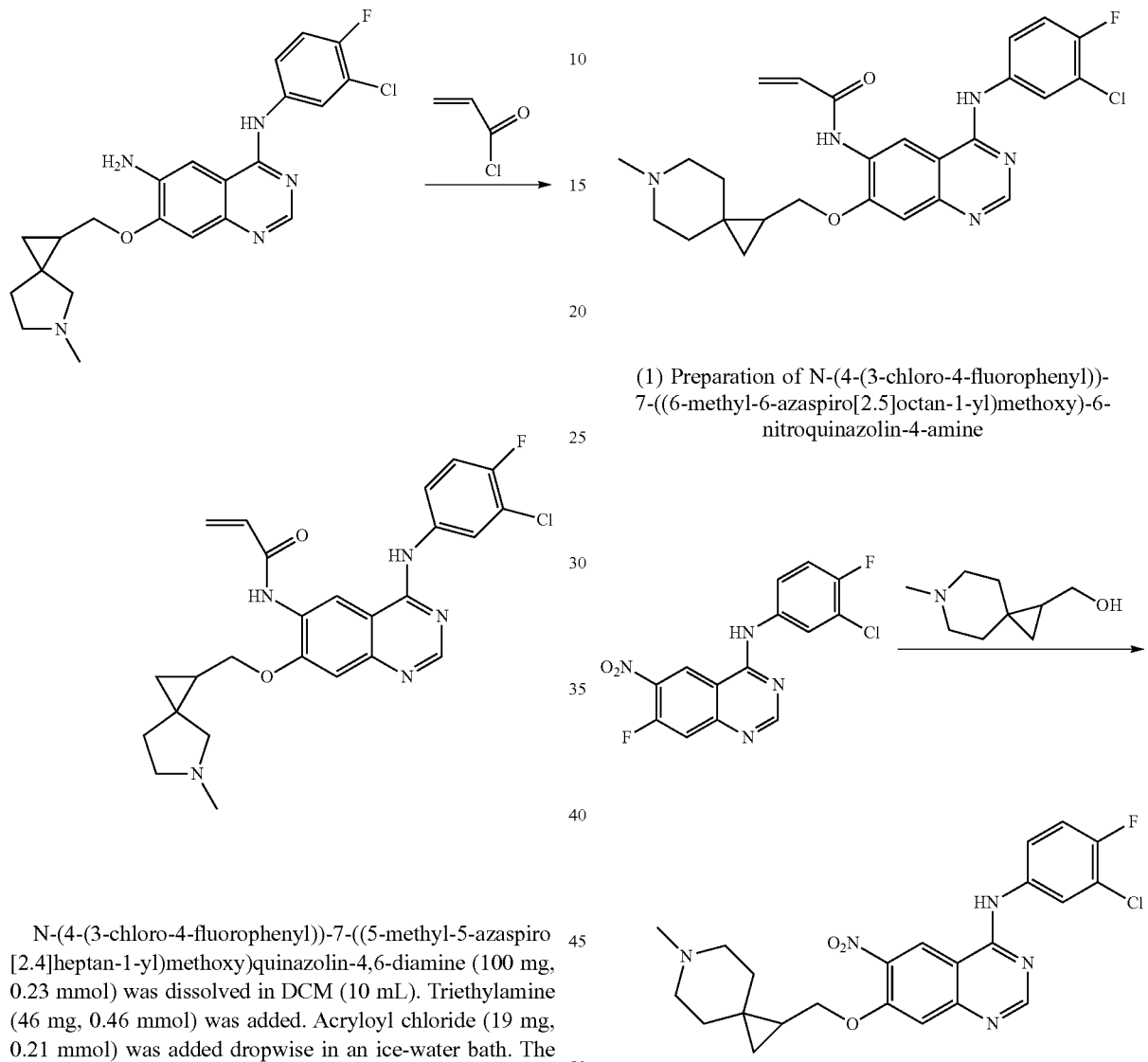

(1) Preparation of N-(4-(3-chloro-4-fluorophenyl))-7-((6-methyl-6-azaspiro[2.5]octan-1-yl)methoxy)-6-nitroquinazolin-4-amine N-(4-(3-chloro-4-fluorophenyl))-7-((5-methyl-5-azaspiro[2.4]heptan-1-yl)methoxy)quinazolin-4,6-diamine (100 mg, 0.23 mmol) was dissolved in DCM (10 mL). Triethylamine (46 mg, 0.46 mmol) was added. Acryloyl chloride (19 mg, 0.21 mmol) was added dropwise in an ice-water bath. The mixture was stirred at room temperature for 30 min. After the completion of reaction, water (50 mL) was added. The mixture was extracted with EA, and rotary-evaporated to dryness under a reduce pressure. The resulting residue was purified by a silica gel column chromatography (eluted with dichloromethane/methanol=15/1) to produce N-[4-(3-chloro-4-fluorophenylamino)-7-((5-methyl-5-azaspiro[2.4]heptan-1-yl)methoxy)quinazolin-6-yl]-acrylamide (14 mg) in a yield of 14%.

Molecular formula: $C_{25}H_{25}ClFN_5O_2$

Mass spectrum (m/e): 482.3 (M+1), 241.6 (M/2)

$^1$HNMR (400 MHz, CDCl$_3$) δ9.35 (s, 1H), 9.00 (s, 1H), 8.60 (s, 1H), 7.98 (s, 1H), 7.78 (d, 1H), 7.54 (d, 1H), 6.95 (m, 2H), 6.52 (m, 2H), 5.83 (m, 1H), 4.57 (m, 1H), 3.65 (m, 1H), 0.68-3.23 (m, 12H).

(6-methyl-6-azaspiro[2.5]octan-1-yl)methanol (400 mg, 2.58 mmol) was dissolved in DMF (20 mL). 60% sodium hydride (230 mg, 3.87 mmol) was added in batch in an ice bath under an atmosphere of N$_2$. The mixture was moved to an atmosphere of room temperature and stirred for 1 h. N-(4-(3-chloro-4-fluorophenyl))-7-fluoro-6-nitroquinazolin-4-amine (954 mg, 2.83 mmol) was added. The mixture was stirred at room temperature overnight. After the completion of reaction, water (20 mL) was added. The mixture was filtered. The filtered cake was dried in vacuum to produce N-(4-(3-chloro-4-fluorophenyl))-7-((6-methyl-6-azaspiro[2.5]octan-1-yl)methoxy)-6-nitroquinazolin-4-amine (300 mg) in a yield of 25%.

(2) Preparation of N-(4-(3-chloro-4-fluorophenyl))-7-((6-methyl-6-azaspiro[2.5]octan-1-yl)methoxy)quinazolin-4,6-diamine

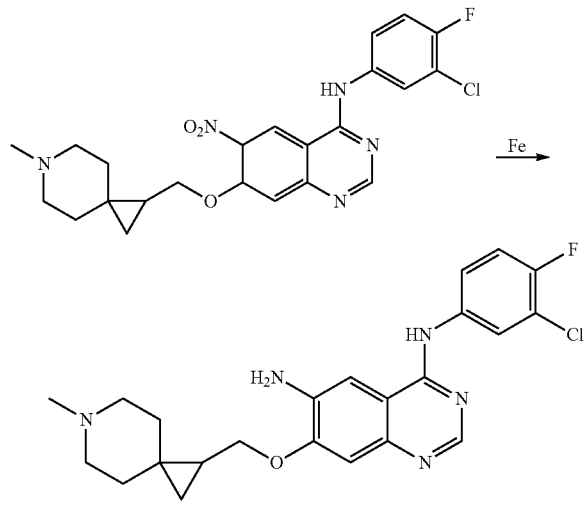

N-(4-(3-chloro-4-fluorophenyl))-7-((6-methyl-6-azaspiro[2.5]octan-1-yl)methoxy)-6-nitroquinazolin-4-amine (300 mg, 0.64 mmol) was dissolved in a mixed solvent (60 mL) of acetic acid and ethanol ($CH_3COOH/EtOH=1/3$). To the mixture was added Fe powder (177 mg, 3.18 mmol). The mixture was warmed up to 30° C. and stirred for 12 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduced pressure to produce N-(4-(3-chloro-4-fluorophenyl))-7-((6-methyl-6-azaspiro[2.5]octan-1-yl)methoxy)quinazolin-4,6-diamine (200 mg) in a yield of 71%.

(3) Preparation of N-[4-(3-chloro-4-fluorophenylamino)-7-((6-methyl-6-azaspiro[2.5]octan-1-yl)methoxy)quinazolin-6-yl]-acrylamide

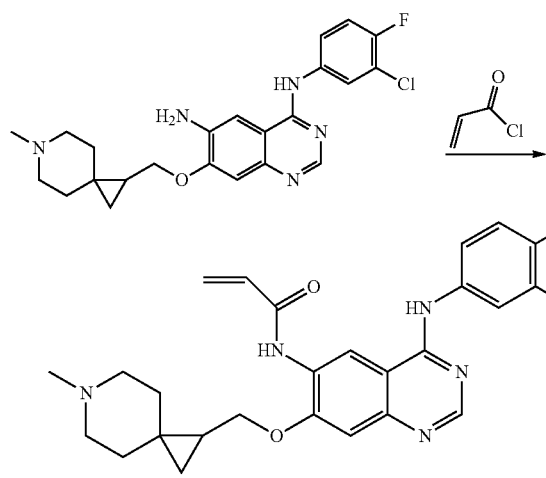

N-(4-(3-chloro-4-fluorophenyl))-7-((6-methyl-6-azaspiro[2.5]octan-1-yl)methoxy)quinazolin-4,6-diamine (200 mg, 0.45 mmol) was dissolved in DCM (10 mL). Triethylamine (46 mg, 0.46 mmol) was added. Acryloyl chloride (39 mg, 0.43 mmol) was added dropwise in an ice-water bath. The mixture was stirred at room temperature for 30 min. After the completion of reaction, water (50 mL) was added. The mixture was extracted with EA. The organic layer was rotary-evaporated to dryness under a reduced pressure. The resulting residue was purified by a silica gel column chromatography (eluted with dichloromethane/methanol=15/1) to produce N-[4-(3-chloro-4-fluorophenylamino)-7-((6-methyl-6-azaspiro[2.5]octan-1-yl)methoxy)quinazolin-6-yl]-acrylamide 25 mg) in a yield of 12%.

Molecular formula: $C_{26}H_{27}ClFN_5O_2$

Mass spectrum (m/e): 496.2 (M+1), 248.6 (M/2)

$^1$HNMR (400 MHz, CDCl$_3$) δ9.13 (s, 1H), 8.66 (s, 1H), 8.32 (s, 1H), 7.97 (d, 1H), 7.66 (s, 1H), 7.55 (d, 1H), 7.25 (s, 1H), 7.17 (t, 1H), 6.52 (d, 1H), 6.42 (m, 1H), 5.90 (d, 1H), 4.39 (m, 1H), 4.07 (t, 1H), 2.69 (m, 2H), 2.55 (m, 2H), 2.40 (s, 3H), 2.04 (s, 1H), 1.80 (m, 2H), 1.56 (m, 2H), 1.30 (m, 2H).

Example 14 Preparation of N-[4-(3-chloro-4-fluorophenylamino)-7-(2-(6-methyl-6-azaspiro[2.5]octan-1-yl)ethoxy)quinazolin-6-yl]-acrylamide (Compound 14)

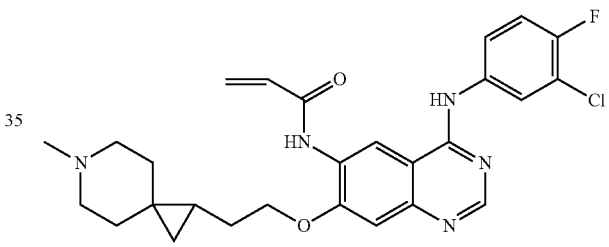

(1) Preparation of N-(4-(3-chloro-4-fluorophenyl))-7-(2-(6-methyl-6-azaspiro[2.5]octan-1-yl)ethoxy)-6-nitroquinazolin-4-amine

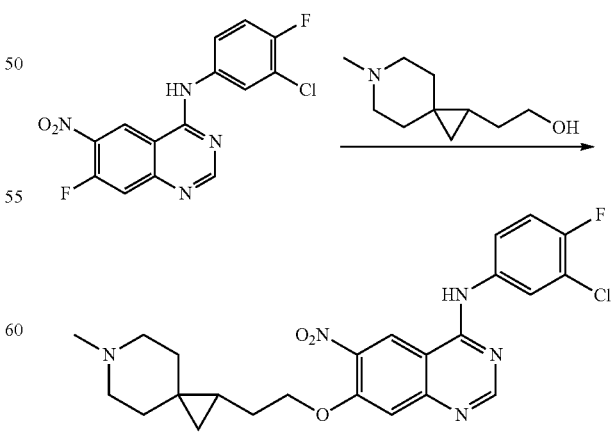

2-(6-methyl-6-azaspiro[2,5]octan-1-yl)ethanol (9 g, 53 mmol) was dissolved in DMF (200 mL). 60% sodium hydride (10 g, 0.25 mol) was added in batch in an ice bath under an atmosphere of $N_2$. The mixture was moved to an atmosphere of room temperature and stirred for 1 h. N-(4-(3-chloro-4-fluorophenyl))-7-fluoro-6-nitroquinazolin-4-amine (18 g, 53 mmol) was added. The mixture was stirred at room temperature overnight. After the completion of reaction, water (20 mL) was added. The mixture was filtered. The filtered cake was purified by a silica gel column chromatography (eluted with dichloromethane/methanol=20/1) to produce N-(4-(3-chloro-4-fluorophenyl))-7-(2-(6-methyl-6-azaspiro[2.5]octan-1-yl)ethoxy)-6-nitroquinazolin-4-amine (17.0 g) in a yield of 66%.

(2) Preparation of N-(4-(3-chloro-4-fluorophenyl))-7-(2-(6-methyl-6-azaspiro[2.5]octan-1-yl)ethoxy)quinazolin-4,6-diamine

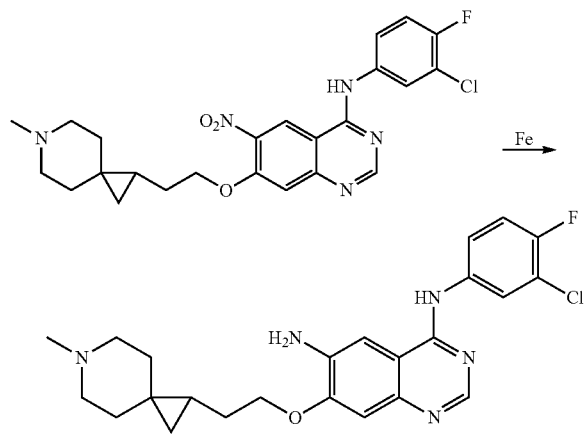

N-(4-(3-chloro-4-fluorophenyl))-7-(2-(6-methyl-6-azaspiro[2.5]octan-1-yl)ethoxy)-6-nitroquinazolin-4-amine (17 g, 35 mmol) was dissolved in a mixed solvent (300 mL) of acetic acid and ethanol ($CH_3COOH$/EtOH=1/3). To the mixture was added Fe powder (13.6 g, 243 mmol). The mixture was stirred at room temperature for 12 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduce pressure. The resulting residue was purified by a silica gel column chromatography (eluted with dichloromethane/methanol=20/1) to produce N-(4-(3-chloro-4-fluorophenyl))-7-(2-(6-methyl-6-azaspiro[2.5]octan-1-yl)ethoxy)quinazolin-4,6-diamine (8.2 g) in a yield of 51%.

(3) Preparation of N-[4-(3-chloro-4-fluorophenylamino)-7-(2-(6-methyl-6-azaspiro[2.5]octan-1-yl)ethoxy)quinazolin-6-yl]-acrylamide

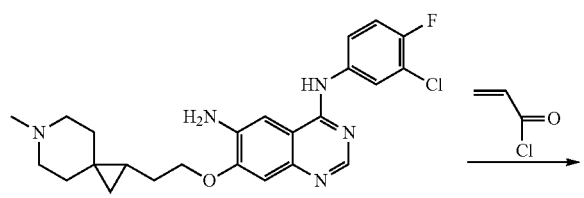

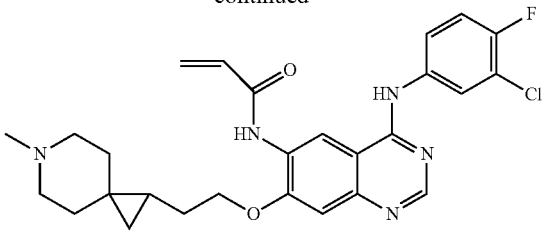

N-(4-(3-chloro-4-fluorophenyl))-7-(2-(6-methyl-6-azaspiro[2.5]octan-1-yl)ethoxy)quinazolin-4,6-diamine (300 mg, 6.6 mmol) was dissolved in DCM (50 mL). Triethylamine (2.0 g, 145 mmol) was added. Acryloyl chloride (600 mg, 6.7 mmol) was added dropwise in an ice-water bath. The mixture was stirred at room temperature for 30 min. After the completion of reaction, water (50 mL) was added. The mixture was extracted with EA. The organic layer was rotary-evaporated to dryness under a reduced pressure. The resulting residue was purified by a silica gel column chromatography (eluted with dichloromethane/methanol=30/1) to produce N-[4-(3-chloro-4-fluorophenylamino)-7-(2-(6-methyl-6-azaspiro[2.5]octan-1-yl)ethoxy)quinazolin-6-yl]-acrylamide 0.5 g) in a yield of 15%.

Molecular formula: $C_{27}H_{29}ClFN_5O_2$

Mass spectrum (m/e): 510.2 (M+1), 255.9 (M/2)

$^1$H NMR (400 MHz, $CDCl_3$) δ9.14 (s, 1H), 8.69 (s, 1H), 8.24 (s, 1H), 7.99 (d, 1H), 7.55 (m, 1H), 7.53 (m, 1H), 7.27 (s, 1H), 7.19 (t, 1H), 6.52 (d, 1H), 6.41 (m, 1H), 5.90 (d, 1H), 4.34 (m, 2H), 2.82 (m, 2H), 2.80 (m, 2H), 2.38 (s, 3H), 0.62-2.19 (m, 9H).

Example 15 Preparation of (E)-N-[4-(3-chloro-4-fluorophenylamino)-7-(2-((1R,5S,6S)-3-methyl-3-azabicyclo[3.1.0]hexan-6-yl)ethoxy)quinazolin-6-yl]-2-butenamide (Compound 15)

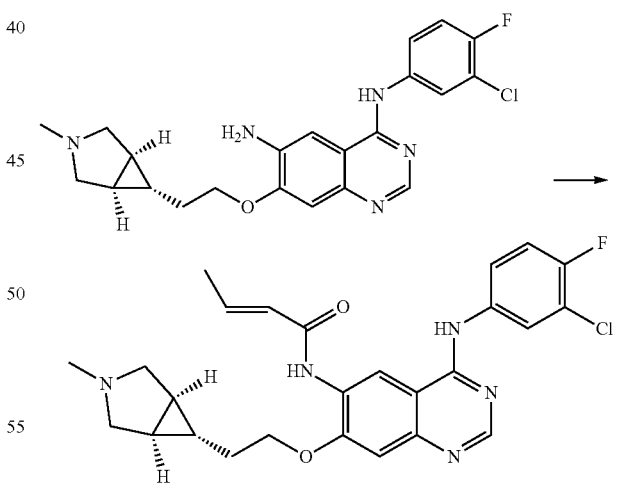

N-(4-(3-chloro-4-fluorophenyl))-7-(2-((1R,5S,6S)-3-methyl-3-azabicyclo[3.1.0]hexan-6-yl)ethoxy)quinazolin-4,6-diamine was prepared according to steps (1) and (2) of Example 8. Trans-2-butenoic acid (0.12 g, 1.2 mmol) was dissolved in DMF (5 mL). Then HATU (0.05 g, 1.32 mmol), triethylamine (0.5 mL) and N-(4-(3-chloro-4-fluorophenyl))-7-(2-((1R,5S,6S)-3-methyl-3-azabicyclo[3.1.0]hexan-6-yl)ethoxy)quinazolin-4,6-diamine (500 mg, 1.2 mmol) were added. The mixture was stirred at room temperature for 12 h. After the completion of reaction, water (50 mL) was added. The reaction was extracted with dichloromethane. The organic layer was rotary-evaporated to dryness under a reduced pressure. The resulting residue was purified by a silica gel column chromatography (eluted with dichloromethane/methanol=10/1-5/1) to produce (E)-N-[4-(3-chloro-4-fluorophenylamino)-7-(2-((1R,5S,6S)-3-methyl-3-azabicyclo[3.1.0]hexan-6-yl)ethoxy)quinazolin-6-yl]-acrylamide (30 mg) in a yield of 5%.

Molecular formula: $C_{26}H_{27}ClFN_5O_2$

Mass spectrum (m/e): 496.2 (M+1), 248.6 (M/2)

$^1$H NMR (400 MHz, DMSO-$d_6$) δ10.45 (br s, 1H), 9.40 (br s, 1H), 8.97 (s, 1H), 8.69 (s, 1H), 8.05 (s, 1H), 7.72 (m, 1H), 7.46 (t, 1H), 7.29 (m, 1H), 6.98 (m, 1H), 6.47 (d, 1H), 4.26 (m, 2H), 3.54 (m, 2H), 3.34 (m, 3H), 2.76 (s, 3H), 1.74-1.91 (m, 6H), 1.23 (m, 1H).

Example 16 Preparation of (E)-N-[4-(3-chloro-4-fluorophenylamino)-7-((7-methyl-7-azaspiro[3.5]nonan-2-yl)methoxy) quinazolin-6-yl]-2-butenamide (Compound 16)

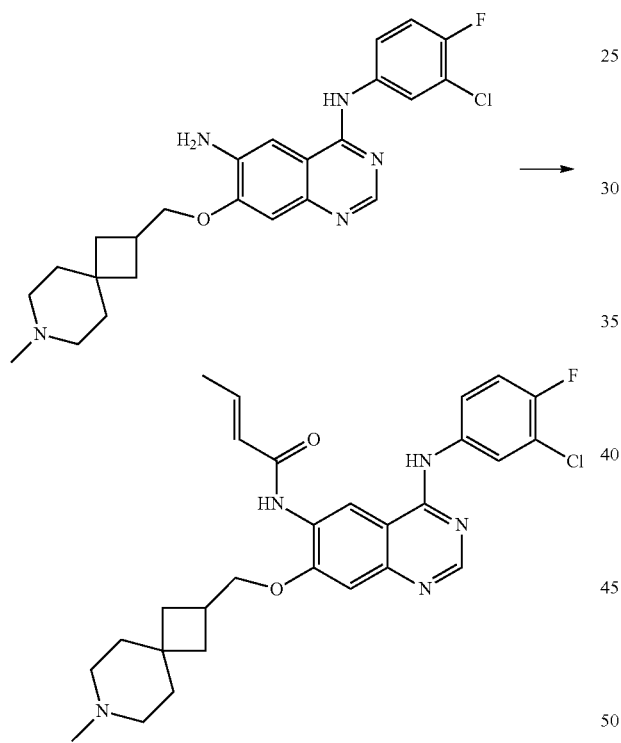

N-(4-(3-chloro-4-fluorophenyl))-7-((7-methyl-7-azaspiro[3.5]nonan-2-yl)methoxy)quinazolin-4,6-diamine was prepared according to steps (1) and (2) of Example 18. Trans-2-butenoic acid (98 mg, 1.1 mmol) was dissolved in DMF (10 mL). Then HATU (563 g, 1.32 mmol), DIEA (441 mg, 3.4 mmol) and N-(4-(3-chloro-4-fluorophenyl)-7-((7-methyl-7-azaspiro[3.5]nonan-2-yl))methoxy)quinazolin-4,6-diamine (400 mg, 0.88 mmol) were added. The mixture was stirred at room temperature for 12 h. After the completion of reaction, water (50 mL) was added. The reaction was extracted with dichloromethane. The organic layer was rotary-evaporated to dryness under a reduced pressure. The resulting residue was purified by a silica gel column chromatography (eluted with dichloromethane/methanol=10/1-5/1) to produce (E)-N-[4-(3-chloro-4-fluorophenylamino)-7-((7-methyl-7-azaspiro[3.5]nonan-2-yl))methoxy) quinazolin-6-yl]-2-butenamide 30 mg) in a yield of 7%.

Molecular formula: $C_{28}H_{31}ClFN_5O_2$ MW: 524

Mass spectrum (m/e): 524.2 (M+1), 262.6 (M/2)

$^1$H NMR (400 MHz, CDCl$_3$) δ9.08 (s, 1H), 8.65 (s, 1H), 8.03 (s, 1H), 7.96 (d, 1H), 7.52 (d, 1H), 7.23 (s, 1H), 7.15 (t, 1H), 7.06 (m, 1H), 5.99 (d, 1H), 4.17 (d, 2H), 2.84 (m, 1H), 2.27 (m, 4H), 2.26 (s, 3H), 2.00 (m, 2H), 1.97 (d, 3H), 1.62-1.82 (m, 6H).

Example 17 Preparation of (E)-N-[4-(3-chloro-4-fluorophenylamino)-7-((7-methyl-7-azaspiro[3.5]nonan-2-yl)methoxy) quinazolin-6-yl]-2-pentenamide (Compound 17) and its Hydrochloride

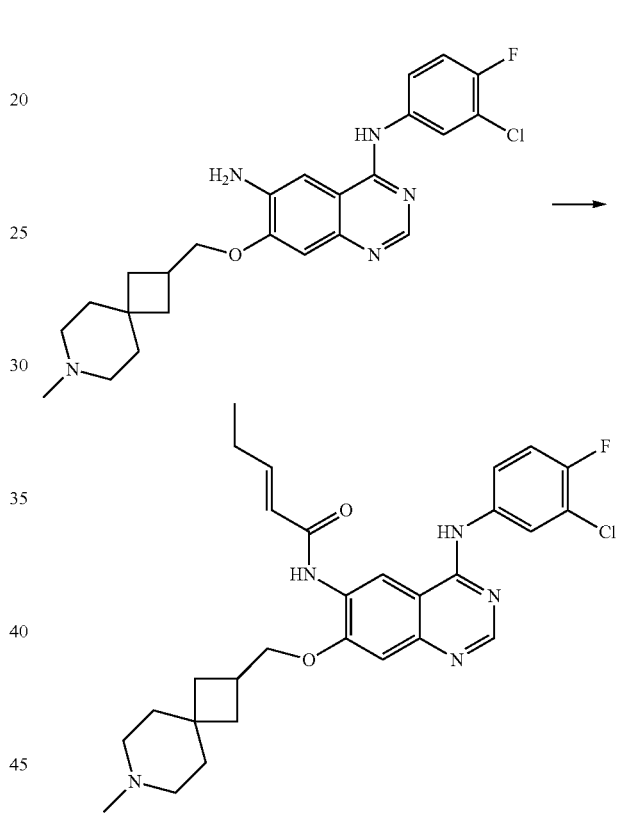

(1) Preparation of N-(4-(3-chloro-4-fluorophenyl))-7-((7-methyl-7-azaspiro[3.5]nonan-2-yl)methoxy) quinazolin-4,6-diamine N-(4-(3-chloro-4-fluorophenyl))-7-((7-methyl-7-azaspiro[3.5]nonan-2-yl)methoxy)quinazolin-4,6-diamine was prepared according to steps (1) and (2) of Example 18.

(2) Preparation of (E)-N-[4-(3-chloro-4-fluorophenylamino)-7-((7-methyl-7-azaspiro[3.5]nonan-2-yl)methoxy) quinazolin-6-yl]-2-pentenamide Trans-2-pentenoic acid (86 mg, 0.86 mmol) was dissolved in DMF (10 mL). Then HATU (425 g, 1.12 mmol), DIEA (333 mg, 2.6 mmol) and N-(4-(3-chloro-4-fluorophenyl))-7-((7-methyl-7-azaspiro[3.5]nonan-2-yl)methoxy)quinazoline4,6-diamine (300 mg, 0.66 mmol) were added. The mixture was stirred at room temperature for 12 h. After the completion of reaction, water (50 mL) was added. The reaction was extracted with dichloromethane. The organic layer was rotary-evaporated to dryness under a reduced pressure. The resulting residue was purified by a silica gel column chromatography (eluted with dichloromethane/methanol=10/1-5/1) to produce (E)-N-[4-(3-chloro-4-fluorophenylamino)-7-((7-methyl-7-azaspiro[3.5]nonan-2-yl)methoxy) quinazolin-6-yl]-2-pentenamide 30 mg) in a yield of 8%.

(3) Preparation of (E)-N-[4-(3-chloro-4-fluorophenylamino)-7-((7-methyl-7-azaspiro[3.5]nonan-2-yl)methoxy) quinazolin-6-yl]-2-pentenamide (Compound 17) Hydrochloride (E)-N-[4-(3-chloro-4-fluorophenylamino)-7-((7-methyl-7-azaspiro[3.5]nonan-2-yl)methoxy) quinazolin-6-yl]-2-pentenamide (58 mg, 0.11 mmol) was dissolved in methanol (10 mL). HCl was added dropwise at room temperature. The reaction was conducted for 2 h under stirring, and then the solvent was evaporated off to produce a yellow solid (E)-N-[4-(3-chloro-4-fluorophenylamino)-7-((7-methyl-7-azaspiro[3.5]nonan-2-yl)methoxy) quinazolin-6-yl]-2-pentenamide hydrochloride 61 mg) in a yield of 100%.

Molecular formula: $C_{29}H_{34}Cl_2FN_5O_2$
Mass spectrum (m/e): 538.1 (M+1), 269.6 (M/2)
$^1H$ NMR (400 MHz, DMSO-$d_6$) δ11.0 (br s, 1H), 9.41 (s, 1H), 9.01 (s, 1H), 8.94 (s, 1H), 8.82 (s, 1H), 7.98 (d, 1H), 7.65 (d, 1H), 7.52 (t, 1H), 7.26 (s, 1H), 5.67 (m, 2H), 4.24 (d, 2H), 3.28 (d, 2H), 2.80 (m, 2H), 2.74 (s, 3H), 1.63-1.98 (m, 14H).

Example 18 Preparation of N-[4-(3-chloro-4-fluorophenylamino)-7-((7-methyl-7-azaspiro[3.5]nonan-2-yl)methoxy)quinazolin-6-yl]-acrylamide (Compound 18)

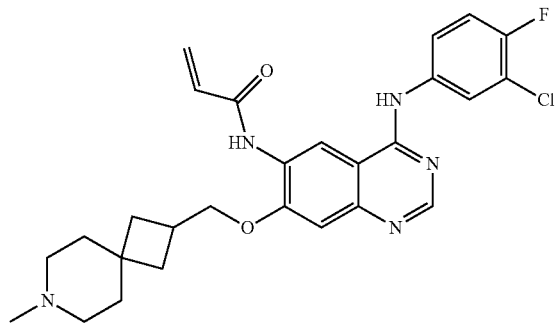 [SMILES: C=CC(=O)Nc1cc2c(Nc3ccc(F)c(Cl)c3)ncnc2cc1OCC1CC2(CCN(C)CC2)C1]

(1) Preparation of N-(4-(3-chloro-4-fluorophenyl))-7-((7-methyl-7-azaspiro[3.5]nonan-2-yl)methoxy)-6-nitroquinazolin-4-amine

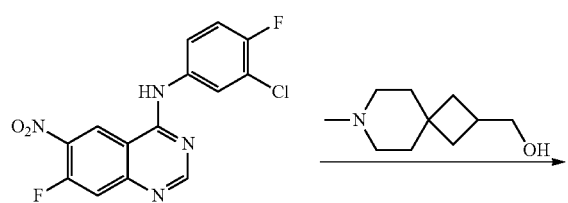

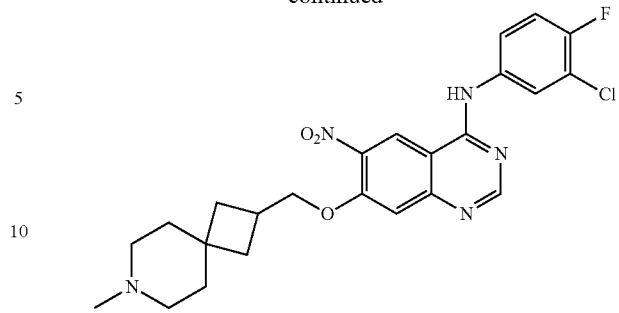

(7-methyl-7-azaspiro[3.5]nonan-2-yl)methanol (9 g, 53 mmol) was dissolved in DMF (20 mL). 60% sodium hydride (10 g, 0.25 mol) was added in batch in an ice bath under an atmosphere of $N_2$. The mixture was moved to an atmosphere of room temperature and stirred for 1 h. N-(4-(3-chloro-4-fluorophenyl))-7-fluoro-6-nitroquinazolin-4-amine (18 g, 53 mmol) was added. The mixture was stirred at room temperature overnight. After the completion of reaction, water (20 mL) was added. The mixture was filtered. The filtered cake was dried in vacuum to produce N-(4-(3-chloro-4-fluorophenyl))-7-((7-methyl-7-azaspiro[3.5]nonan-2-yl)methoxy)-6-nitroquinazolin-4-amine (17 g) in a yield of 66%.

(2) Preparation of N-(4-(3-chloro-4-fluorophenyl))-7-((7-methyl-7-azaspiro[3.5]nonan-2-yl)methoxy) quinazolin-4,6-diamine

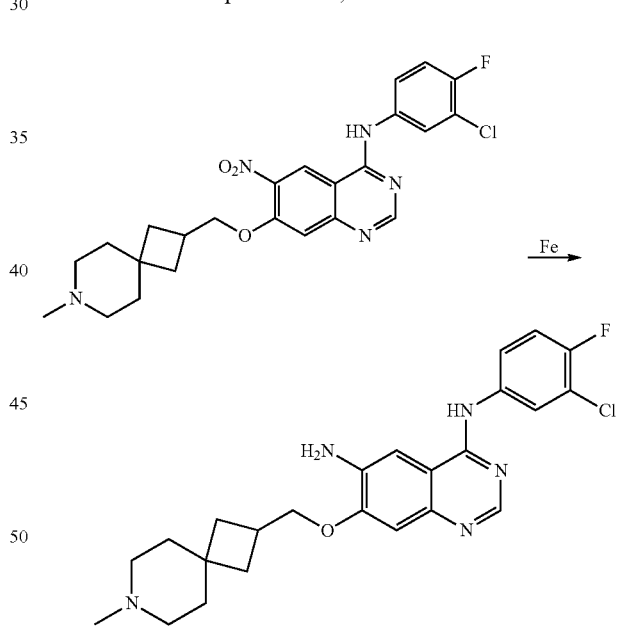

N-(4-(3-chloro-4-fluorophenyl))-7-((7-methyl-7-azaspiro[3.5]nonan-2-yl)methoxy)-6-nitroquinazolin-4-amine (17 g, 35 mmol) was dissolved in a mixed solvent (60 mL) of acetic acid and ethanol ($CH_3COOH/EtOH=1/3$). To the mixture was added Fe powder (13.6 g, 243 mmol). The mixture was stirred at room temperature for 12 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduce pressure. The resulting residue was purified by a silica gel column chromatography (eluted with dichloromethane/methanol=10/1) to produce N-(4-(3-chloro-4- fluorophenyl))-7-((7-methyl-7-azaspiro[3.5]nonan-2-yl)methoxy)quinazolin-4,6-diamine 10 g) in a yield of 63%.

(3) Preparation of N-[4-(3-chloro-4-fluorophenylamino)-7-((7-methyl-7-azaspiro[3.5]nonan-2-yl)methoxy)quinazolin-6-yl]-acrylamide

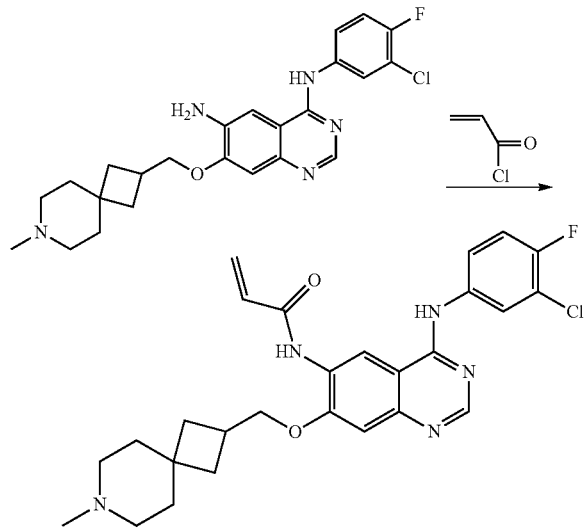

N-(4-(3-chloro-4-fluorophenyl))-7-((7-methyl-7-azaspiro[3.5]nonan-2-yl)methoxy)quinazolin-4,6-diamine (3 g, 6.6 mmol) was dissolved in DCM (10 mL). Triethylamine (2 g, 19.8 mmol) was added. Acryloyl chloride (600 mg, 6.6 mmol) was added dropwise in an ice-water bath. The mixture was stirred at room temperature for 30 min. After the completion of reaction, water (50 mL) was added. The mixture was extracted with EA, and rotary-evaporated to dryness under a reduce pressure. The resulting residue was purified by a silica gel column chromatography (eluted with dichloromethane/methanol=15/1) to produce N-[4-(3-chloro-4-fluorophenylamino)-7-((7-methyl-7-azaspiro[3.5]nonan-2-yl)methoxy)quinazolin-6-yl]-acrylamide (1.26 g) in a yield of 37%.

Molecular formula: $C_{27}H_{29}ClFN_5O_2$
Mass spectrum (m/e): 510.2 (M+1), 255.8 (M/2)
$^1$H NMR (400 MHz, CDCl$_3$) δ9.12 (s, 1H), 8.67 (s, 1H), 8.18 (s, 1H), 7.98 (d, 1H), 7.55 (m, 1H), 7.52 (s, 1H), 7.26 (s, 1H), 7.17 (t, 1H), 6.50 (d, 1H), 6.34 (m, 1H), 5.88 (d, 1H), 4.21 (d, 2H), 2.86 (m, 1H), 2.21-2.50 (m, 7H), 2.07 (t, 2H), 1.82 (m, 2H), 1.63-1.71 (m, 4H).

Example 19 Preparation of N-[4-(3-chloro-4-fluorophenylamino)-7-(2-(7-methyl-7-azaspiro[3.5]nonan-2-yl)ethoxy)quinazolin-6-yl]-acrylamide (Compound 19) and its Hydrochloride

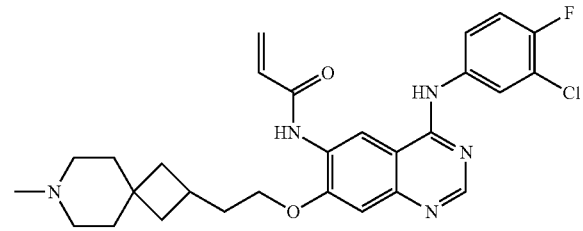 [SMILES: C=CC(=O)Nc1cc2c(Nc3ccc(F)c(Cl)c3)ncnc2cc1OCCC1CC2(CCN(C)CC2)C1]

(1) Preparation of N-(4-(3-chloro-4-fluorophenyl))-7-(2-(7-methyl-7-azaspiro[3.5]nonan-2-yl)ethoxy)-6-nitroquinazolin-4-amine

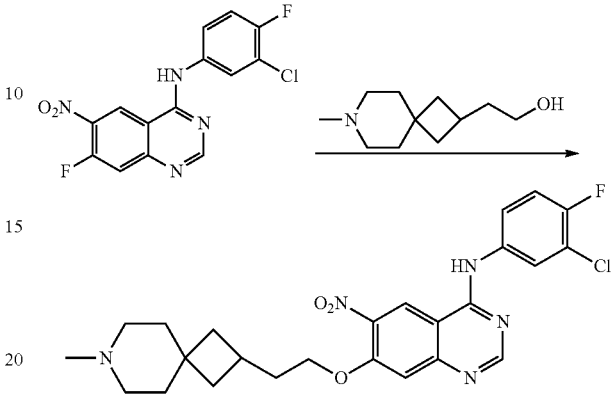

2-(7-methyl-7-azaspiro[3.5]nonan-2-yl)ethanol (2.7 g, 14.8 mmol) was dissolved in DMF (20 mL). 60% sodium hydride (1.78 g, 44.5 mmol) was added in batch in an ice bath under an atmosphere of N$_2$. The mixture was moved to an atmosphere of room temperature and stirred for 1 h. N-(4-(3-chloro-4-fluorophenyl))-7-fluoro-6-nitroquinazolin-4-amine (4.95 g, 14.7 mmol) was added. The mixture was stirred at room temperature overnight. After the completion of reaction, water (20 mL) was added. The mixture was filtered. The filtered cake was dried in vacuum to produce N-(4-(3-chloro-4-fluorophenyl))-7-(2-(7-methyl-7-azaspiro[3.5]nonan-2-yl)ethoxy)-6-nitroquinazolin-4-amine (5.0 g) in a yield of 68%.

(2) Preparation of N-(4-(3-chloro-4-fluorophenyl))-7-(2-(7-methyl-7-azaspiro[3.5]nonan-2-yl)ethoxy)quinazolin-4,6-diamine

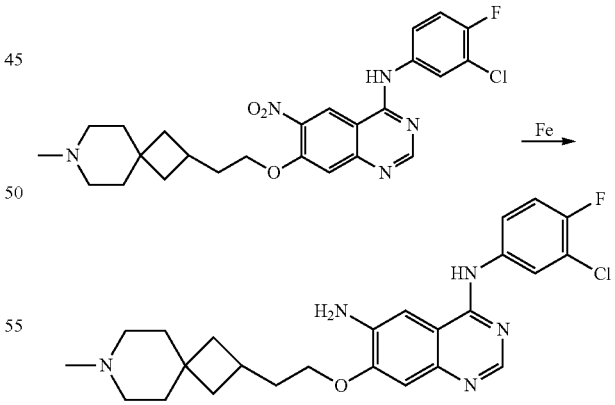

N-(4-(3-chloro-4-fluorophenyl))-7-(2-(7-methyl-7-azaspiro[3.5]nonan-2-yl)ethoxy)-6-nitroquinazolin-4-amine (5 g, 10 mmol) was dissolved in a mixed solvent (250 mL) of acetic acid and ethanol (CH$_3$COOH/EtOH=1/3). To the mixture was added Fe powder (1.96 g, 35 mmol). The mixture was warmed up to 30° C. and stirred for 12 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduce pressure. The resulting residue was purified by a silica gel column chromatography (eluted with dichloromethane/methanol=10/1) to produce N-(4-(3-chloro-4-fluorophenyl))-7-(2-(7-methyl-7-azaspiro[3.5]nonan-2-yl)ethoxy)quinazolin-4,6-diamine 2.5 g) in a yield of 53%.

(3) Preparation of N-[4-(3-chloro-4-fluorophenylamino)-7-(2-(7-methyl-7-azaspiro[3.5]nonan-2-yl)ethoxy)quinazolin-6-yl]-acrylamide

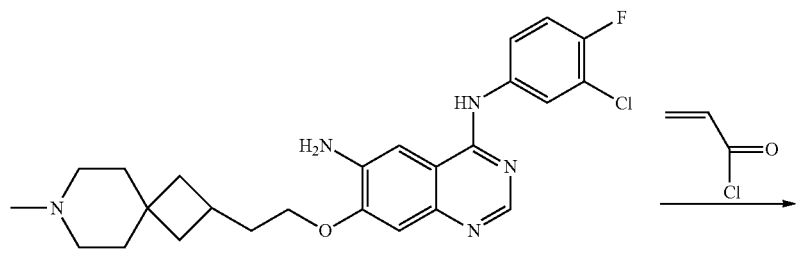

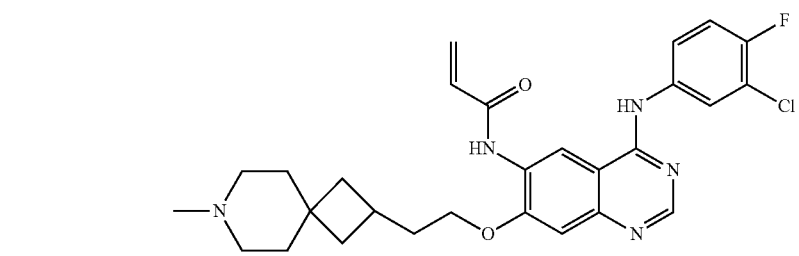

N-(4-(3-chloro-4-fluorophenyl))-7-(2-(7-methyl-7-azaspiro[3.5]nonan-2-yl)ethoxy)quinazolin-4,6-diamine (300 mg, 0.64 mmol) was dissolved in DCM (10 mL). Triethylamine (194 mg, 1.92 mmol) was added. Acryloyl chloride (60 mg, 0.67 mmol) was added dropwise in an ice-water bath. The mixture was stirred at room temperature for 30 min. After the completion of reaction, water (50 mL) was added. The mixture was extracted with EA. The organic layer was rotary-evaporated to dryness under a reduced pressure. The resulting residue was purified by a silica gel column chromatography (eluted with dichloromethane/methanol=15/1) to produce N-[4-(3-chloro-4-fluorophenylamino)-7-(2-(7-methyl-7-azaspiro[3.5]nonan-2-yl)ethoxy)quinazolin-6-yl]-acrylamide 100 mg) in a yield of 30%.

(4) Preparation of N-[4-(3-chloro-4-fluorophenylamino)-7-(2-(7-methyl-7-azaspiro[3.5]nonan-2-yl)ethoxy)quinazolin-6-yl]-acrylamide (Compound 19) Hydrochloride N-[4-(3-chloro-4-fluorophenylamino)-7-(2-(7-methyl-7-azaspiro[3.5]nonan-2-yl)ethoxy)quinazolin-6-yl]-acrylamide (100 mg, 0.19 mmol) was dissolved in methanol (10 mL). A HCl gas was introduced under an ice-water bath. The reaction was conducted for 30 min under stirring, and then the solvent was evaporated off to produce a white solid N-[4-(3-chloro-4-fluorophenylamino)-7-(2-(7-methyl-7-azaspiro[3.5]nonan-2-yl)ethoxy)quinazolin-6-yl]-acrylamide hydrochloride (105 mg) in a yield of 97%.

Molecular formula: $C_{28}H_{32}Cl_2FN_5O_2$

Mass spectrum (m/e): 524.0 (M+1), 262.5 (M/2)

$^1$HNMR (400 MHz, DMSO-$d_6$) δ10.72 (br s, 1H), 9.77 (br s, 1H), 9.73 (s, 1H), 9.00 (s, 1H), 8.75 (s, 1H), 8.03 (d, 1H), 7.52 (d, 1H), 7.49 (t, 1H), 7.36 (s, 1H), 6.73 (m, 1H), 6.30 (d, 1H), 5.83 (m, 1H), 4.18 (t, 2H), 2.81 (m, 1H), 2.77 (m, 1H), 2.68 (s, 3H), 1.52-2.08 (m, 13H).

Example 20 Preparation of (E)-N-(4-(3-chloro-4-fluorophenylamino)-7-((7-methyl-7-azaspiro[3.5]nonan-2-yl)methoxy) quinazolin-6-yl)-4-dimethylamino-2-butenamide (Compound 20)

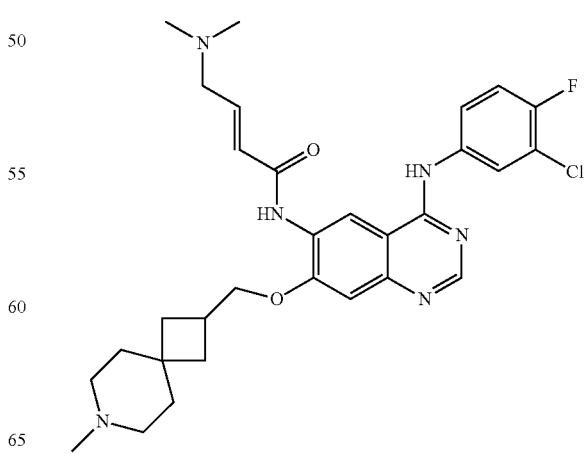

(1) Preparation of (E)-N-(4-(3-chloro-4-fluorophenylamino)-7-((7-methyl-7-azaspiro[3.5]nonan-2-yl)methoxy) quinazolin-6-yl)-4-bromo-2-butenamide

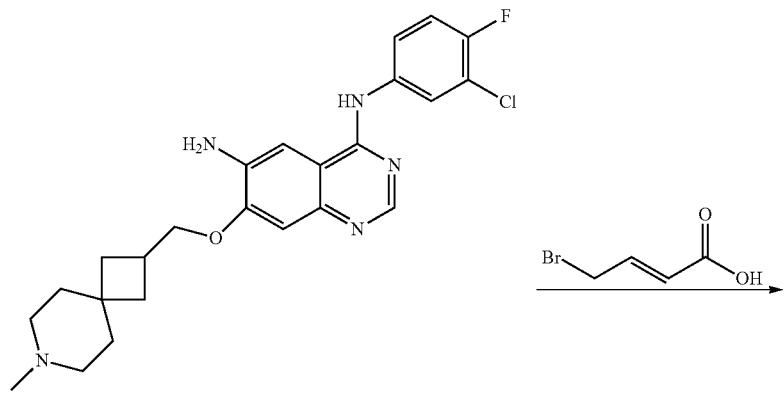

N-(4-(3-chloro-4-fluorophenyl))-7-((7-methyl-7-azaspiro[3.5]nonan-2-yl)methoxy)quinazolin-4,6-diamine was prepared according to steps (1) and (2) of Example 18. 4-bromocrotonic acid (900 mg, 5.5 mmol) was dissolved in THF (10 mL) under nitrogen. DCC (1130 mg, 5.5 mmol) was added under an ice bath. The mixture was stirred for 0.5 h. Then a solution of N-(4-(3-chloro-4-fluorophenyl))-7-((7-methyl-7-azaspiro[3.5]nonan-2-yl)methoxy)quinazolin-4,6-diamine (500 mg, 1.1 mmol) in DMF (10 mL) was added. The mixture was stirred for 40 min, and then a crude product of (E)-N-(4-(3-chloro-4-fluorophenylamino)-7-((7-methyl-7-azaspiro[3.5]nonan-2-yl)methoxy) quinazolin-6-yl)-4-bromo-2-butenamide was obtained. This crude product was directly used in the next step with purification.

(2) Preparation of (E)-N-(4-(3-chloro-4-fluorophenylamino)-7-((7-methyl-7-azaspiro[3.5]nonan-2-yl)methoxy) quinazolin-6-yl)-4-dimethylamino-2-butenamide -continued

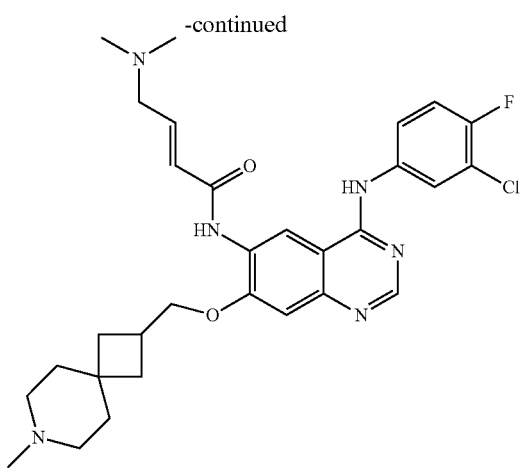

To the product in the previous step, i.e. (E)-N-(4-(3-chloro-4-fluorophenylamino)-7-((7-methyl-7-azaspiro[3.5]nonan-2-yl)methoxy) quinazolin-6-yl)-4-bromo-2-butenamide, were successively added dimethylamine hydrochloride (1.25 g, 15.3 mmol) and DIEA (2.68 mL, 15.4 mmol). The mixture was continuously stirred for 2 h under an ice bath. The mixture was moved to an atmosphere of room temperature and stirred overnight. To the reaction was added a saturated sodium bicarbonate solution. The reaction was extracted with ethyl acetate. The organic layer was dried over anhydrous sodium sulphate and concentrated. Then, the concentrate was separated by a reverse-phase preparative column ($C_{18}$, ODS-AQ 40-60 um, mobile phase: methanol/water=50/50) to produce (E)-N-(4-(3-chloro-4-fluorophenylamino)-7-((7-methyl-7-azaspiro[3.5]nonan-2-yl)methoxy) quinazolin-6-yl)-4-dimethylamino-2-butenamide (120 mg) in a yield of 19.2%.

Molecular formula: $C_{30}H_{36}ClFN_6O_2$

Mass spectrum (m/e): 567 (M+1)

$^1$HNMR (400 MHz, DMSO-$d_6$) δ9.79 (s, 1H), 9.46 (s, 1H), 8.80 (s, 1H), 8.54 (s, 1H), 8.13-8.17 (m, 1H), 7.79-7.83 (m, 1H), 7.39-7.46 (m, 1H), 7.27 (s, 1H), 6.77 (dd, 1H), 6.51 (d, 1H), 4.17 (d, 2H), 3.08 (d, 2H), 2.70-2.82 (m, 1H), 2.21 (m, 10H), 2.11 (s, 3H), 1.88 (t, 2H), 1.71 (t, 2H), 1.22-1.51 (m, 4H).

Example 21 Preparation of (E)-N-[4-(3-chloro-4-fluorophenylamino)-7-((2-(3-methyl-3-aza-bicyclo[3.1.0]-6-hexyl)-ethoxy)quinazolin-6-yl)-4-dimethylamino]-crotonamide (Compound 21)

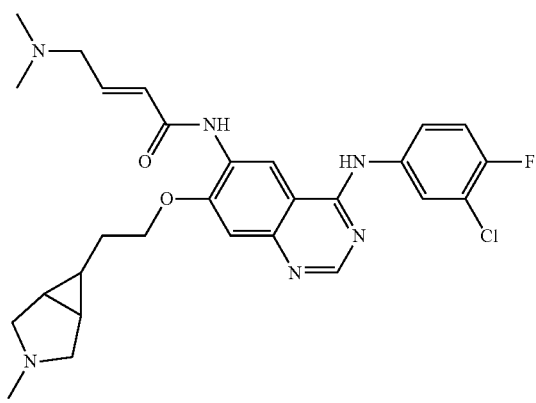 [SMILES: CN(C)C/C=C/C(=O)Nc1cc2c(Nc3ccc(F)c(Cl)c3)ncnc2cc1OCCC1C2CN(C)CC12]

(1) Preparation of N-(4-(3-chloro-4-fluorophenyl))-7-(2-(3-methyl-3-azabicyclo[3.1.0]-6-hexyl)-ethoxy)-6-nitroquinazolin-4-amine

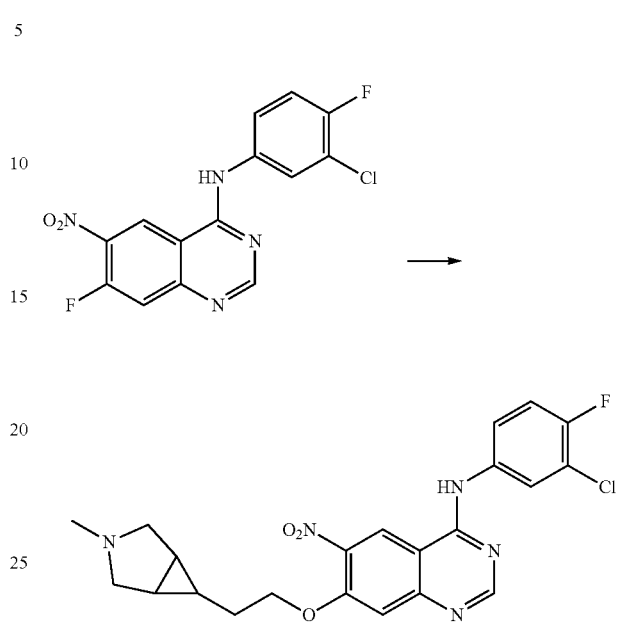

2-(3-methyl-3-aza-bicyclo[3.1.0]-6-hexyl)-ethanol (7.5 g, 53 mmol) was dissolved in DMF (20 mL). 60% sodium hydride (10 g, 0.25 mol) was added in batch in an ice bath under an atmosphere of $N_2$. The mixture was moved to an atmosphere of room temperature and stirred for 1 h. N-(4-(3-chloro-4-fluorophenyl))-7-fluoro-6-nitroquinazolin-4-amine (18 g, 53 mmol) was added. The mixture was stirred at room temperature overnight. After the completion of reaction, water (20 mL) was added. The mixture was filtered. The filtered cake was dried in vacuum to produce N-(4-(3-chloro-4-fluorophenyl))-7-(2-(3-methyl-3-aza-bicyclo[3.1.0]-6-hexyl)-ethoxy)-6-nitroquinazolin-4-amine (14.8 g) in a yield of 61%.

(2) Preparation of N-(4-(3-chloro-4-fluorophenyl))-7-(2-(3-methyl-3-aza-bicyclo[3.1.0]-6-hexyl)-ethoxy)quinazolin-4,6-diamine

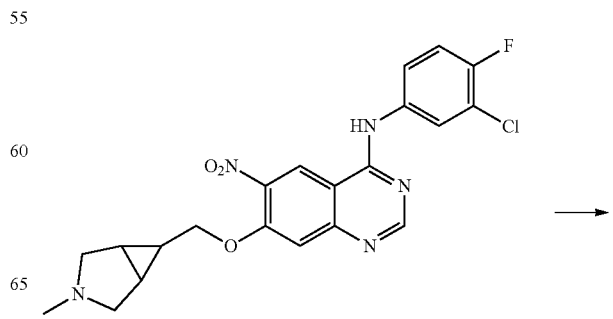

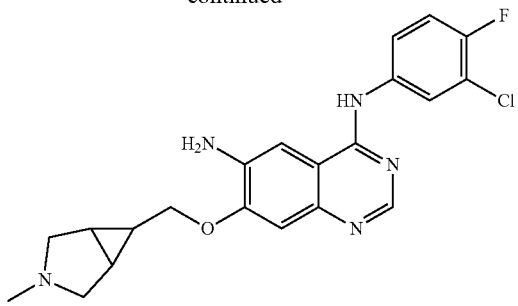

N-(4-(3-chloro-4-fluorophenyl))-7-(2-(3-methyl-3-aza-bicyclo[3.1.0]-6-hexyl)-ethoxy))-6-nitroquinazolin-4-amine (14.8 g, 32 mmol) was dissolved in a mixed solvent (60 mL) of acetic acid and ethanol (CH₃COOH/EtOH=1/3). To the mixture was added Fe powder (13.6 g, 243 mmol). The mixture was stirred at room temperature for 12 h. After the completion of reaction, the rotary-evaporation was conducted to remove EtOH. Water (30 mL) was added. The mixture was adjusted with 1 mol/L NaOH solution until it became basic. The mixture was extracted with EA. The organic layer was rotary-evaporated to dryness under a reduce pressure. The resulting residue was purified by a silica gel column chromatography (eluted with dichloromethane/methanol=10/1) to produce N-(4-(3-chloro-4-fluorophenyl))-7-(2-(3-methyl-3-aza-bicyclo[3.1.0]-6-hexyl)-ethoxy))quinazolin-4,6-diamine (8.3 g) in a yield of 62%.

(3) Preparation of (E)-N-[4-(3-chloro-4-fluorophenylamino)-7-((2-(3-methyl-3-aza-bicyclo[3.1.0]-6-hexyl)-ethoxy)-quinazolin-6-yl-4-chloro)]-crotonamide

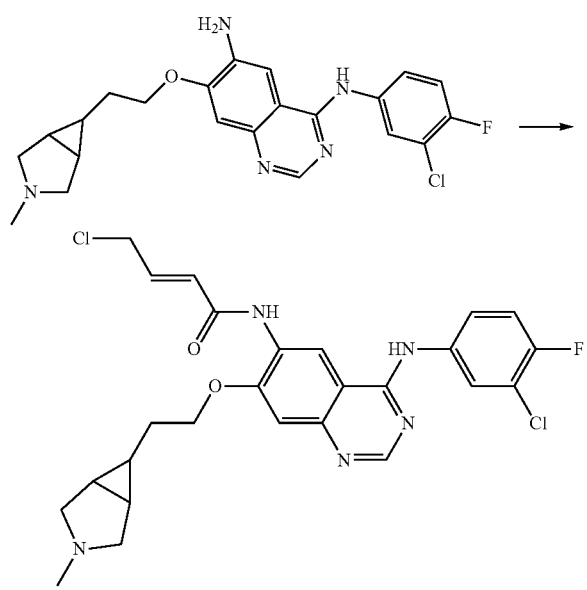

N-(4-(3-chloro-4-fluorophenyl))-7-(2-(3-methyl-3-aza-bicyclo[3.1.0]-6-hexyl)-ethoxy))quinazolin-4,6-diamine (2.73 g, 6.6 mmol) was dissolved in DCM (10 mL). Triethylamine (2 g, 19.8 mmol) was added. (E)-4-chloro-crotonyl chloride (600 mg, 6.6 mmol) was added dropwise in an ice-water bath. The mixture was stirred at room temperature for 30 min. After the completion of reaction, water (50 mL) was added. The mixture was extracted with EA. The organic layer was rotary-evaporated to dryness under a reduce pressure. The resulting residue was purified by a silica gel column chromatography (eluted with dichloromethane/methanol=15/1) to produce (E)-N-[4-(3-chloro-4-fluorophenylamino)-7-((2-(3-methyl-3-aza-bicyclo[3.1.0]-6-hexyl)-ethoxy)-quinazolin-6-yl-4-chloro)]-crotonamide (2.81 g) in a yield of 81%.

(4) Preparation of N-[4-(3-chloro-4-fluorophenylamino)-7-(2-(3-methyl-3-aza-bicyclo[3.1.0]-6-hexyl)-ethoxy)-quinazolin-6-((E)-4-dimethylamino)]-crotonamide

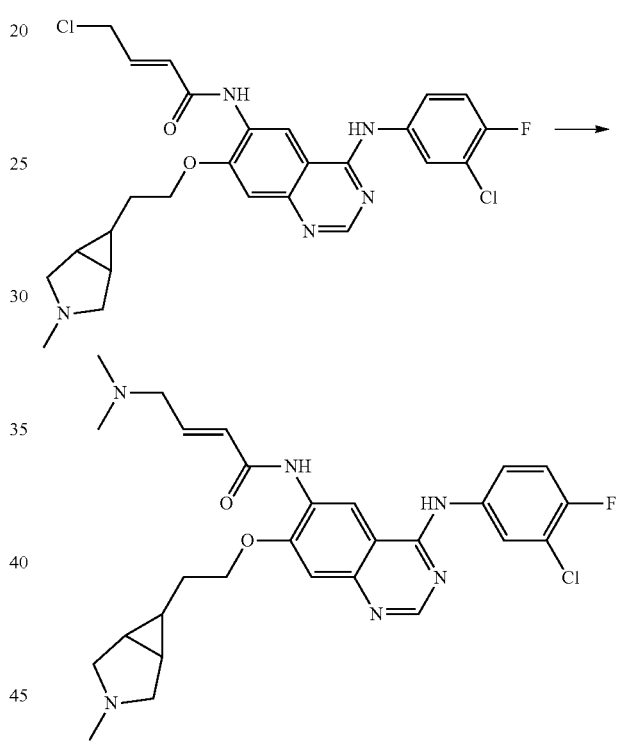

N-[4-(3-chloro-4-fluorophenylamino)-7-(2-(3-methyl-3-aza-bicyclo[3.1.0]-6-hexyl)-ethoxy)-quinazolin-6-((E)-4-chloro)]-crotonamide (0.23 g, 0.4 mmol) was dissolved in acetonitrile (30 mL). Methylamine hydrochloride (0.32 g, 4 mmol) and cesium carbonate (2.6 g, 8 mmol) were added under the nitrogen gas protection. The mixture was heated to reflux and filtered. The filtrate was rotary-evaporated to dryness under a reduce pressure. Then the resulting residue was directly separated by a reverse phase preparative column (C18, ODS-AQ 40-60 um, mobile phase: methanol/water=50/50) to produce a compound named (E)-N-[4-(3-chloro-4-fluorophenylamino)-7-((2-(3-methyl-3-aza-bicyclo[3.1.0]-6-hexyl)-ethoxy)quinazolin-6-yl)-4-dimethylamino]-crotonamide (0.14 g) in a yield of 37%.

Molecular formula: $C_{28}H_{32}ClFN_6O_2$

Mass spectrum (m/e): 539.2 (M+1), 270 (M/2)

¹HNMR (400 MHz, CD₃OD) δ 9.20 (s, 1H), 8.76 (s, 1H), 7.94 (d, 1H), 7.68-7.64 (m, 1H), 7.40-7.35 (m, 2H), 7.11-

7.00 (m, 2H), 4.44-4.41 (m, 2H), 4.08 (d, 2H), 3.73 (d, 2H), 3.36 (s, 4H), 3.00-2.67 (m, 8H), 1.96-1.92 (m, 2H), 1.82-1.75 (m, 3H).

Example 22 Preparation of (E)-N-[4-(3-chloro-4-fluorophenylamino)-7-(((spiro[3.5]octan-2-yl)methoxy)quinazolin-6-yl)-4-dimethylamino]-crotonamide (Compound 22)

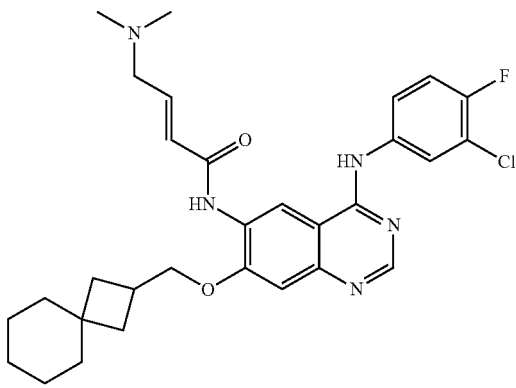 [SMILES: CN(C)C/C=C/C(=O)Nc1cc2c(Nc3ccc(F)c(Cl)c3)ncnc2cc1OCC1CC2(CCCCC2)C1]

(1) Preparation of N-(4-(3-chloro-4-fluorophenyl))-7-((spiro[3.5]octan-2-yl)methoxy)-6-nitroquinazolin-4-amine

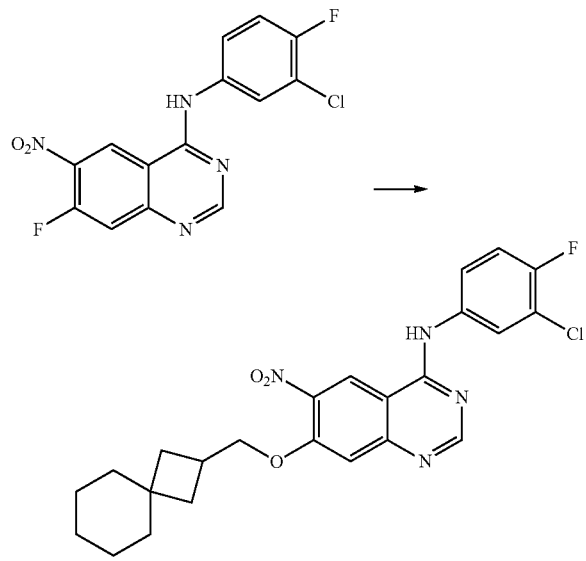

(Spiro[3.5]octan-2-yl)methanol (8.16 g, 53 mmol) was dissolved in DMF (20 mL). 60% sodium hydride (10 g, 0.25 mol) was added in batch in an ice bath under an atmosphere of N$_2$. The mixture was moved to an atmosphere of room temperature and stirred for 1 h. N-(4-(3-chloro-4-fluorophenyl))-7-fluoro-6-nitroquinazolin-4-amine (18 g, 53 mmol) was added. The mixture was stirred at room temperature overnight. After the completion of reaction, water (20 ml) was added. The mixture was filtered. The filtered cake was dried in vacuum to produce N-(4-(3-chloro-4-fluorophenyl))-7-((spiro[3.5]octan-2-yl)methoxy)-6-nitroquinazolin-4-amine (18.68 g) in a yield of 75%.

(2) Preparation of N-(4-(3-chloro-4-fluorophenyl))-7-((spiro[3.5]octan-2-yl)methoxy)-quinazolin-4,6-diamine

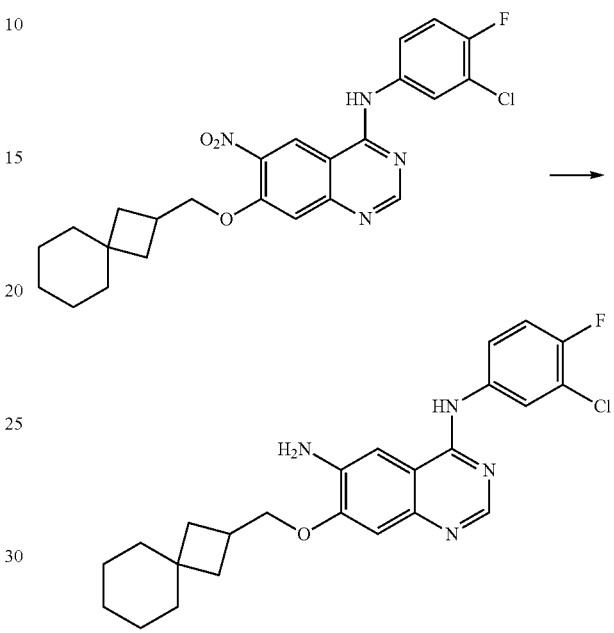

N-(4-(3-chloro-4-fluorophenyl))-7-((spiro[3.5]octan-2-yl)methoxy)-6-nitroquinazolin-4-amine (16.45 g, 35 mmol) was dissolved in a mixed solvent (60 mL) of acetic acid and ethanol (CH$_3$COOH/EtOH=1/3). To the mixture was added Fe powder (13.6 g, 243 mmol). The mixture was stirred at room temperature for 12 h. After the completion of reaction, the mixture was rotary-evaporated under a reduced pressure to remove EtOH. Water (30 mL) was added. The mixture was adjusted with 1 mol/L NaOH solution until it became basic. The mixture was extracted with EA. The organic layer was rotary-evaporated to dryness under a reduce pressure. The resulting residue was purified by a silica gel column chromatography (dichloromethane/methanol=10/1, V/V) to produce N-(4-(3-chloro-4-fluorophenyl))-7-((spiro[3.5]octan-2-yl)methoxy)quinazolin-4,6-diamine (10 g) in a yield of 63%.

(3) Preparation of ((E)-4-dimethylamino)-crotonyl Chloride Hydrochloride

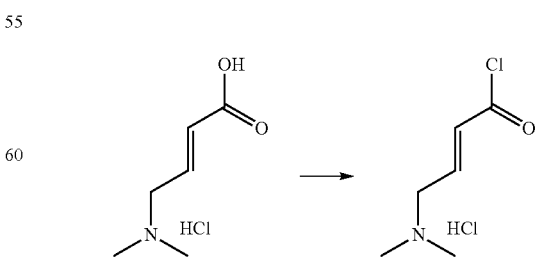

((E)-4-dimethylamino)-crotonic acid hydrochloride (1.65 g, 10 mmol) was dissolved in THF (50 ml). DMF (0.1 mL)

was added. The mixture was cooled to 0° C., and SOCl₂ (5 mL) was slowly added dropwise. The reaction was warmed up to room temperature. After 0.5 h, the mixture was heated to reflux, stirred for 3 h under reflux, then cooled down to room temperature, and evaporated off the excess of SOCl₂ under the nitrogen gas protection. The resulting product was directly used in the next step.

(4) Preparation of (E)-N-[4-(3-chloro-4-fluorophenylamino)-7-(((spiro[3.5]octan-2-yl)methoxy)quinazolin-6-yl-4-dimethylamino]-crotonamide

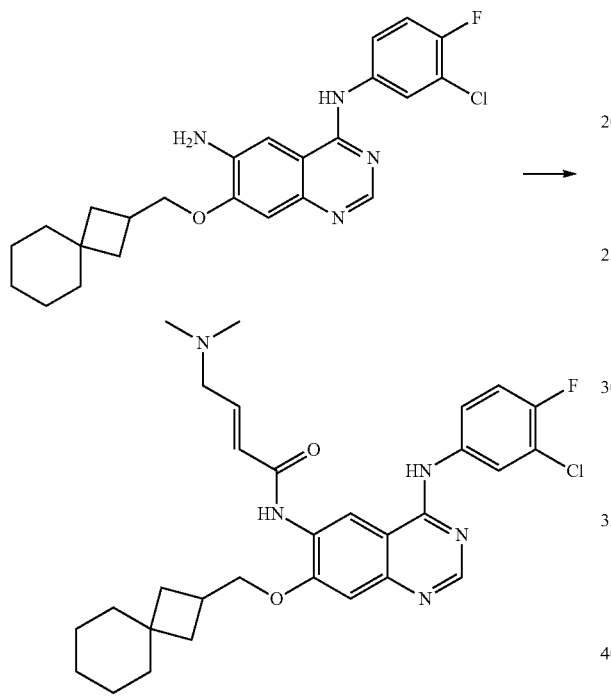

N-(4-(3-chloro-4-fluorophenyl))-7-((spiro[3.5]octan-2-yl)methoxy)quinazolin-4,6-diamine (3 g, 6.6 mmol) was dissolved in DCM (10 mL). Triethylamine (2 g, 19.8 mmol) was added. 6-((E)-4-dimethylamino)]-crotonyl chloride (600 mg, 6.6 mmol) was added dropwise in an ice-water bath. The mixture was stirred at room temperature for 30 min. After the completion of reaction, water (50 mL) was added. The mixture was extracted with EA. The organic layer was rotary-evaporated to dryness under a reduced pressure. The resulting residue was purified by a silica gel column chromatography (eluted with dichloromethane/methanol=15/1) to produce (E)-N-[4-(3-chloro-4-fluorophenylamino)-7-(((spiro[3.5]octan-2-yl)methoxy)quinazolin-6-yl)-4-dimethylamino]-crotonamide (1.26 g) in a yield of 38%.

Molecular formula: $C_{30}H_{35}ClFN_5O_2$

Mass spectrum (m/e): 552.2 (M+1), 256.2 (M/2)

¹HNMR (400 MHz, CD₃OD) δ 9.21 (s, 1H), 8.79 (s, 1H), 7.96 (d, 1H), 7.69-7.68 (m, 1H), 7.42 (d, 1H), 7.34 (s, 1H), 7.04 (t, 1H), 6.84 (d, 1H), 4.37 (d, 2H), 4.09 (d, 2H), 3.0-2.96 (m, 7H), 2.10-2.05 (m, 5H), 1.77-1.63 (m, 7H), 1.37-1.33 (m, 3H).

Example 23 Preparation of (E)-N-(7-(bicyclo[3.1.0]hexan-6-ylmethoxy)-4-(3-chloro-4-fluorophenylamino)quinazolin-6-yl)-4-(dimethylamino)but-2-enamide (Compound 23)

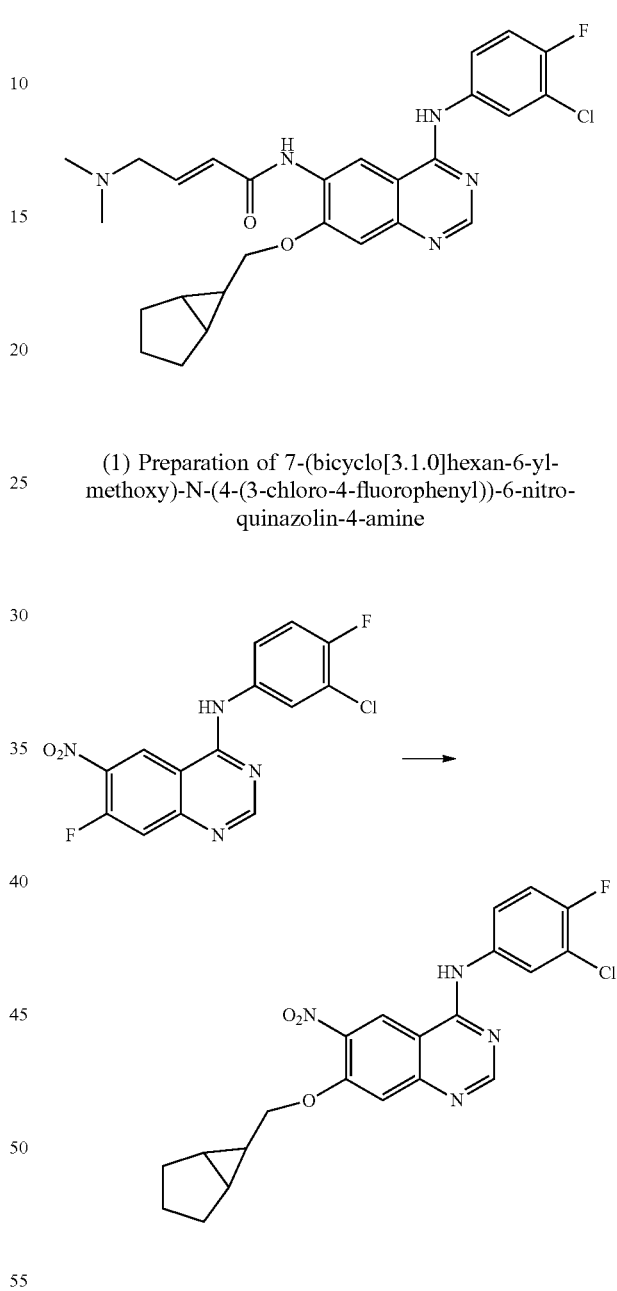

(1) Preparation of 7-(bicyclo[3.1.0]hexan-6-ylmethoxy)-N-(4-(3-chloro-4-fluorophenyl))-6-nitroquinazolin-4-amine To dioxane (50 ml) were added bicyclo[3.1.0]hexan-6-ylmethanol (3.36 g, 30 mmol), potassium carbonate (4.14 g, 30 mmol) and 7-fluoro-4-(3-chloro-4-fluorophenylamine)-6-nitroquinazoline (3.36 g, 10 mmol). The mixture was stirred at room temperature for 24 hr. After the completion of reaction, water was added. The mixture was extracted with ethyl acetate. The organic layer was dried over anhydrous sodium sulphate. The resulting residue was purified with a silica gel column chromatography (petroleum ether/ethyl acetate=1/1) to produce a product (7.57 g) in a yield of 59%.

(2) Preparation of 7-(bicyclo[3.1.0]hexan-6-yl-methoxy)-N-(4-(3-chloro-4-fluorophenyl))quinazolin-4,6-diamine

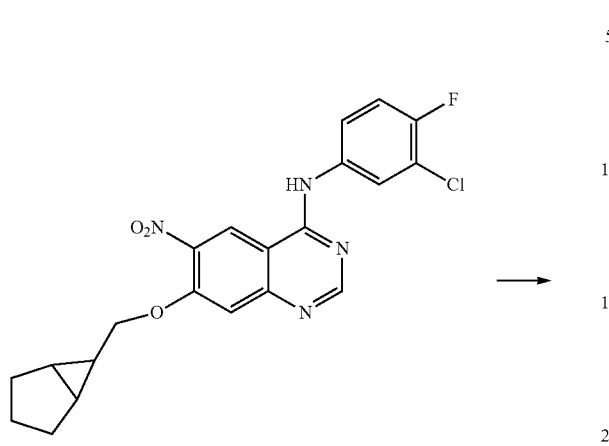

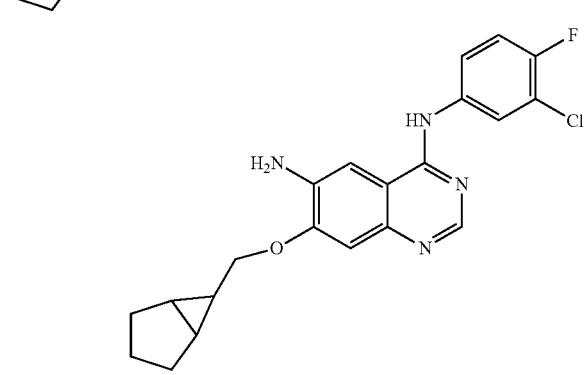

7-(bicyclo[3.1.0]hexan-6-ylmethoxy)-N-(4-(3-chloro-4-fluorophenyl))-6-nitroquinazolin-4-amine (1.71 g, 4 mmol) and Pd/C (0.2 g) were added to tetrahydrofuran (30 mL). The mixture was stirred at room temperature overnight. After the completion of reaction, water was added. The mixture was extracted with ethyl acetate. The organic layer was evaporated to dryness to produce a product (1.40 g) in a yield of 88%.

(3) Preparation of (E)-N-(7-(bicyclo[3.1.0]hexan-6-ylmethoxy)-4-(3-chloro-4-fluorophenylamino)quinazolin-6-yl)-4-(dimethylamino)but-2-enamide

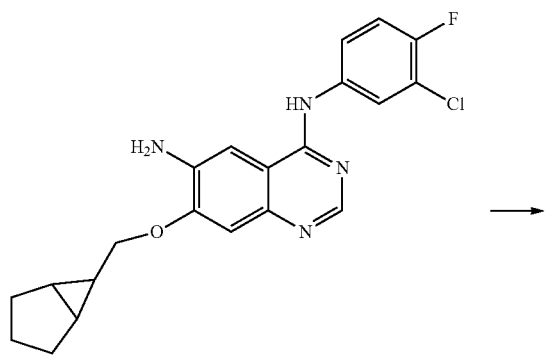

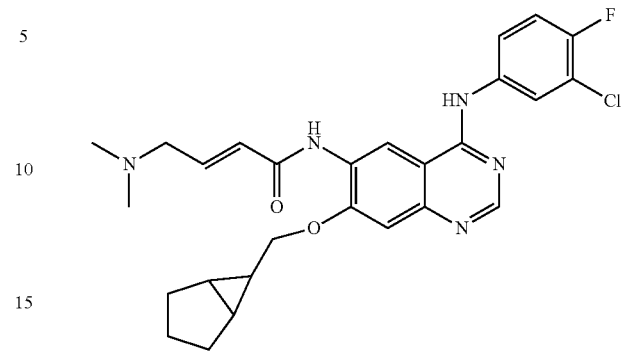

4-(dimethylamino)but-2-enoic acid (0.52 g, 4 mmol) was added to dichloroethane (20 mL). Thionyl chloride (0.95 g, 8 mmol) was added dropwise under an ice bath. The mixture was heated to reflux for 2 hr. After the completion of reaction, the reaction was evaporated to dryness. The resulting residue was dissolved in acetonitrile (50 mL). A solution of triethylamine (0.3 g, 3 mmol) and 7-(bicyclo[3.1.0]hexan-6-ylmethoxy)-N-(4-(3-chloro-4-fluorophenyl))quinazolin-4,6-diamine (1.19 g, 3 mmol) in tetrahydrofuran (100 mL) was added dropwise. The mixture was stirred for 12 hr, and water was added. The reaction was extracted with dichloromethane. The organic layer was dried over anhydrous sodium sulphate. The resulting residue was purified by a preparative liquid chromatography ($C_{18}$, ODS-AQ 40-60 um, mobile phase: methanol/water=50/50) to produce (E)-N-(7-(bicyclo[3.1.0]hexan-6-ylmethoxy)-4-(3-chloro-4-fluorophenylamino)quinazolin-6-yl)-4-(dimethylamino)but-2-enamide (0.168 g) in a yield of 11%.

Molecular formula: $C_{27}H_{29}ClFN_5O_2$

Mass spectrum (m/e): 510 (M+1), 255.7 (M/2)

$^1$HNMR (400 MHz, DMSO-$d_6$) δ 9.78 (s, 1H), 951-9.54 (m, 1H), 8.86 (s, 1H), 8.51-8.52 (m, 1H), 8.11-8.13 (m, 1H), 7.78-7.80 (m, 1H), 7.41 (t, 1H), 7.23 (s, 1H), 6.77-6.81 (m, 1H), 6.54-6.57 (m, 1H), 4.21-4.23 (m, 1H), 4.05-4.07 (m, 1H), 3.08-3.09 (m, 2H), 2.19 (s, 6H), 1.95-2.01 (m, 1H), 1.83-1.91 (m, 2H), 1.88 (m, 2H), 1.71-1.73 (m, 2H), 1.36 (m, 1H), 1.04 (m, 1H).

Compounds 1-16, 18 and 20-23 can be prepared into salts according to the salt-formation methods described for Compound 17 and Compound 19.

The following compounds can also be prepared according to the above-mentioned methods.

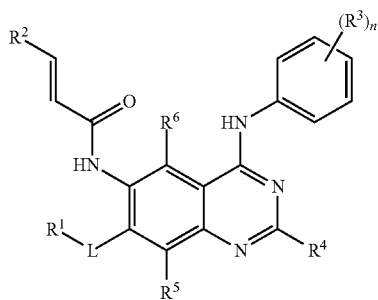

| No. | R¹ | R² | (R³)n | L |
|---|---|---|---|---|
| 24 | (spiro pyrrolidine-piperidine, N-methyl) | H | 3'-Cl, 4'-F | O |
| 25 | (oxa-bridged N-methyl bicyclic) | H | 3'-Cl, 4'-F | O |
| 26 | (octahydropyrrolo[3,4-b]pyridine, N,N-dimethyl) | H | 3'-Cl, 4'-F | O |
| 27 | (octahydropyrrolo[1,2-a]pyrazine, N-methyl) | H | 3'-Cl, 4'-F | O |
| 28 | (octahydropyrrolo[3,4-b]pyrrole, N,N-dimethyl) | H | 3'-Cl, 4'-F | O |
| 29 | (3-azabicyclo[4.1.0]heptane, N-methyl) | H | 3'-Cl, 4'-F | O |
| 30 | (3-azabicyclo[3.1.0]hexane, N-methyl) | H | 3'-Cl, 4'-F | O |
| 31 | (3-azabicyclo[3.1.0]hexane, N-methyl) | —CH₂CH₃ | 3'-Cl, 4'-F | O |

-continued

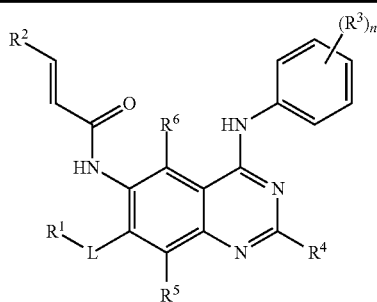

| No. | R¹ | R² | (R³)n | L |
|---|---|---|---|---|
| 32 | (spiro[3.5]non-2-yl with N-CH₃ piperidine, propyl linker) | —CH₂CH₃ | 3'-Cl, 4'-F | O |
| 33 | (spiro[3.5]non-2-yl with N-CH₃ piperidine, propyl linker) | —CH₂N(CH₃)₂ | 3'-Cl, 4'-F | O |
| 34 | (spiro[3.5]non-2-yl with N-CH₃ piperidine, methyl linker) | —CH₂OCH₃ | 3'-Cl, 4'-F | O |
| 35 | (1-oxa-8-aza-spiro[4.5]decane with N-CH₃, ethyl linker) | —CH₃ | 3'-Cl, 4'-F | O |
| 36 | (1-oxa-8-aza-spiro[4.5]decane with N-CH₃, ethyl linker) | —CH₃ | 3'-Cl, 4'-F | O |
| 37 | (3-azabicyclo[3.1.0]hexane with N-CH₃, propyl linker) | —CH₂-piperidine | 3'-Cl, 4'-F | O |
| 38 | (1-oxa-8-aza-spiro[4.5]decane with N-CH₃, ethyl linker) | —CH₂N(CH₃)₂ | 3'-Cl, 4'-F | O |
| 39 | (1-oxa-8-aza-spiro[4.5]decane with N-CH₃, ethyl linker) | —CH₂N(CH₃)₂ | 3'-Cl, 4'-F | O |

-continued

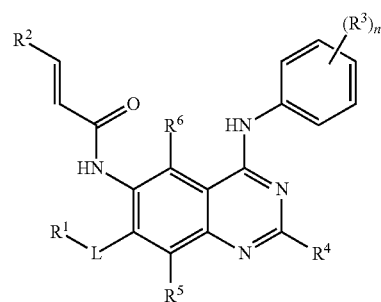

| No. | R¹ | R² | (R³)n | L |
|---|---|---|---|---|
| 40 | (spiro[3.5] with N-CH₂CH₃) | H₃C-O-CH₂- | 3'-Cl, 4'-F | O |
| 41 | (azabicyclic-CH₂-) | H₃C-O-CH₂- | 3'-Cl, 4'-F | O |
| 42 | (decahydronaphthalenyl-CH₂-, NHCH₃) | (CH₃)₂N-CH₂- | 3'-Cl, 4'-F | O |
| 43 | (spiro[2.4]) | (H₃CCH₂)₂N-CH₂- | 3'-Cl, 4'-F | O |
| 44 | (N-methyl bicyclic pyrrolidine-CH₂-) | (H₃CCH₂)₂N-CH₂- | 3'-Cl, 4'-F | O |
| 45 | (oxabicyclic) | (H₃CCH₂)₂N-CH₂- | 3'-Cl, 4'-F | O |
| 46 | (spiro[3.5] with N-CH₂CH₃) | cyclopropyl-CH₂- | 3'-Cl, 4'-F | O |
| 47 | (octahydrocyclopenta[c]pyrrole N-CH₃) | cyclopropyl-CH₂- | 3'-Cl, 4'-F | O |
| 48 | (diazabicyclic with N-CH₂CH₃) | cyclopropyl-CH₂- | 3'-Cl, 4'-F | O |

-continued
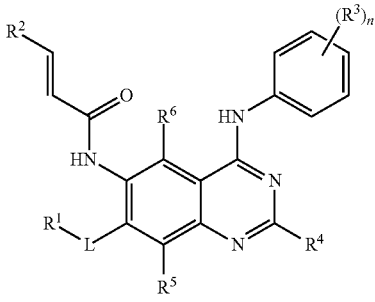
| No. | R¹ | R² | (R³)n | L |
|---|---|---|---|---|
| 49 | 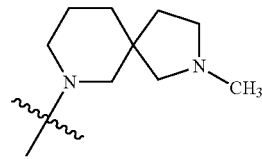 [SMILES: *N1CCCC2(CCN(C)C2)C1] | 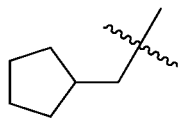 [SMILES: *CC1CCCC1] | 3'-Cl, 4'-F | O |
| 50 | 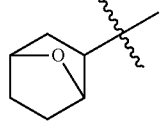 [SMILES: *C1CC2CCC1O2] | 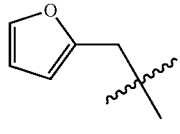 [SMILES: *Cc1ccco1] | 3'-Cl, 4'-F | O |
| 51 | 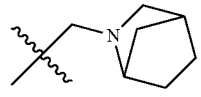 [SMILES: *CN1CC2CCC1C2] | 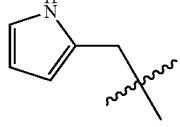 | 3'-Cl, 4'-F | O |
| 52 |  | 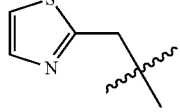 | 3'-Cl, 4'-F | O |
| 53 | 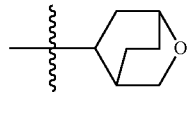 | 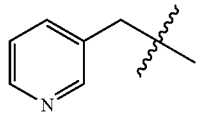 [SMILES: *Cc1cccnc1] | 3'-Cl, 4'-F | O |
| 54 | 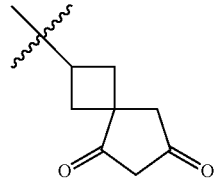 [SMILES: *C1CC2(CC(=O)CC2=O)C1] | 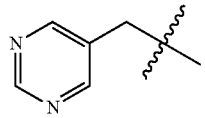 | 3'-Cl, 4'-F | O |
| 55 |  | 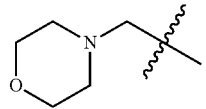 [SMILES: *CN1CCOCC1] | 3'-Cl, 4'-F | O |
| 56 |  | 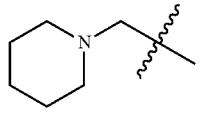 [SMILES: *CN1CCCCC1] | 3'-Cl, 4'-F | O |

-continued

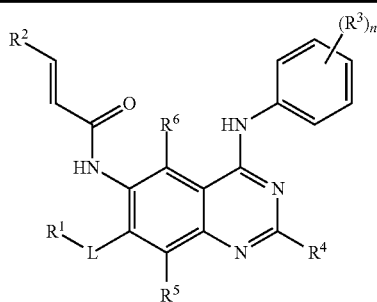

| No. | R¹ | R² | (R³)n | L |
|---|---|---|---|---|
| 57 | (thia-bicyclic) | morpholinomethyl | 3'-Cl, 4'-F | S |
| 58 | (N-methyl octahydrocyclopenta[c]pyrrole) | morpholinomethyl | 3'-Cl, 4'-F | O |
| 59 | (N-methyl octahydrocyclopenta[c]pyrrole) | piperidinomethyl | 3'-Cl, 4'-F | S |
| 60 | (N-methyl octahydrocyclopenta[c]pyrrole) | piperidinomethyl | 3'-Cl, 4'-F | O |
| 61 | (bicyclic sulfone) | morpholinomethyl | 3'-Cl, 4'-F | O |
| 62 | (decalin-NHCH₃) | piperidinomethyl | 3'-Cl, 4'-F | NH |
| 63 | (spiro[2.4]heptane) | morpholinomethyl | 3'-Cl, 4'-F | NH |
| 64 | (dioxo-spiro[3.4]) | morpholinomethyl | 3'-Cl, 4'-F | O |
| 65 | (N-ethyl spiro[3.5]) | morpholinomethyl | 3'-Cl, 4'-F | O |

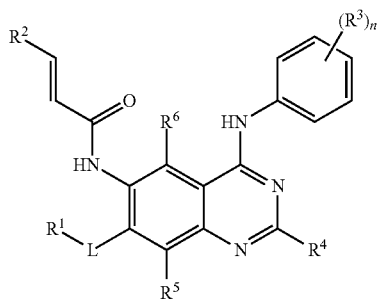

| No. | R¹ | R² | (R³)n | L |
|---|---|---|---|---|
| 66 | (spiro[3.5]nonane with N-CH₂CH₃ piperidine) | piperidinyl-CH₂ | 3'-Cl, 4'-F | O |
| 67 | (spiro[3.5]nonane with N-CH₃ piperidine, CH₂ linker) | morpholinyl-CH₂ | 3'-Cl, 4'-F | O |
| 68 | (2-methyl-2,7-diazaspiro[4.5]decane) | morpholinyl-CH₂ | 3'-Cl, 4'-F | O |
| 69 | (oxabicyclic) | morpholinyl-CH₂ | 3'-Cl, 4'-F | O |
| 70 | (oxabicyclic) | piperidinyl-CH₂ | 3'-Cl, 4'-F | O |
| 71 | (azabicyclo[2.2.1]heptane-CH₂) | morpholinyl-CH₂ | 3'-Cl, 4'-F | O |
| 72 | (N-ethyl-diazabicyclic) | morpholinyl-CH₂ | 3'-Cl, 4'-F | O |
| 73 | (N-ethyl-diazabicyclic) | piperidinyl-CH₂ | 3'-Cl, 4'-F | S |
| 74 | (2-oxabicyclo[2.2.2]octane) | piperidinyl-CH₂ | 3'-Cl, 4'-F | O |

-continued

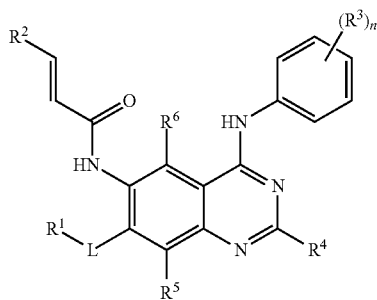

| No. | R¹ | R² | (R³)n | L |
|---|---|---|---|---|
| 75 | N-methyl-azabicyclo-CH₂- | morpholin-N-CH₂- | 3'-Cl, 4'-F | O |
| 76 | N-methyl-azabicyclo-CH₂- | piperidin-N-CH₂- | 3'-Cl, 4'-F | O |
| 77 | N-methyl-azabicyclopentane-CH₂- | piperazin-N-CH₂- (HN) | 3'-Cl, 4'-F | O |
| 78 | N-methyl-octahydrocyclopenta[c]pyrrol- | piperazin-N-CH₂- (HN) | 3'-Cl, 4'-F | O |
| 79 | N-ethyl-spiro[3.5]azonane- | pyrrolidin-N-CH₂- | 3'-Cl, 4'-F | O |
| 80 | oxabicyclo- | piperazin-N-CH₂- (HN) | 3'-Cl, 4'-F | NH |
| 81 | N,N'-ethyl-diazabicyclo- | pyrrolidin-N-CH₂- | 3'-Cl, 4'-F | S |
| 82 | oxabicyclo- | pyrrolidin-N-CH₂- | 3'-Cl, 4'-F | S |
| 83 | N-methyl-azabicyclo-CH₂- | piperazin-N-CH₂- (HN) | 3'-Cl, 4'-F | O |

-continued

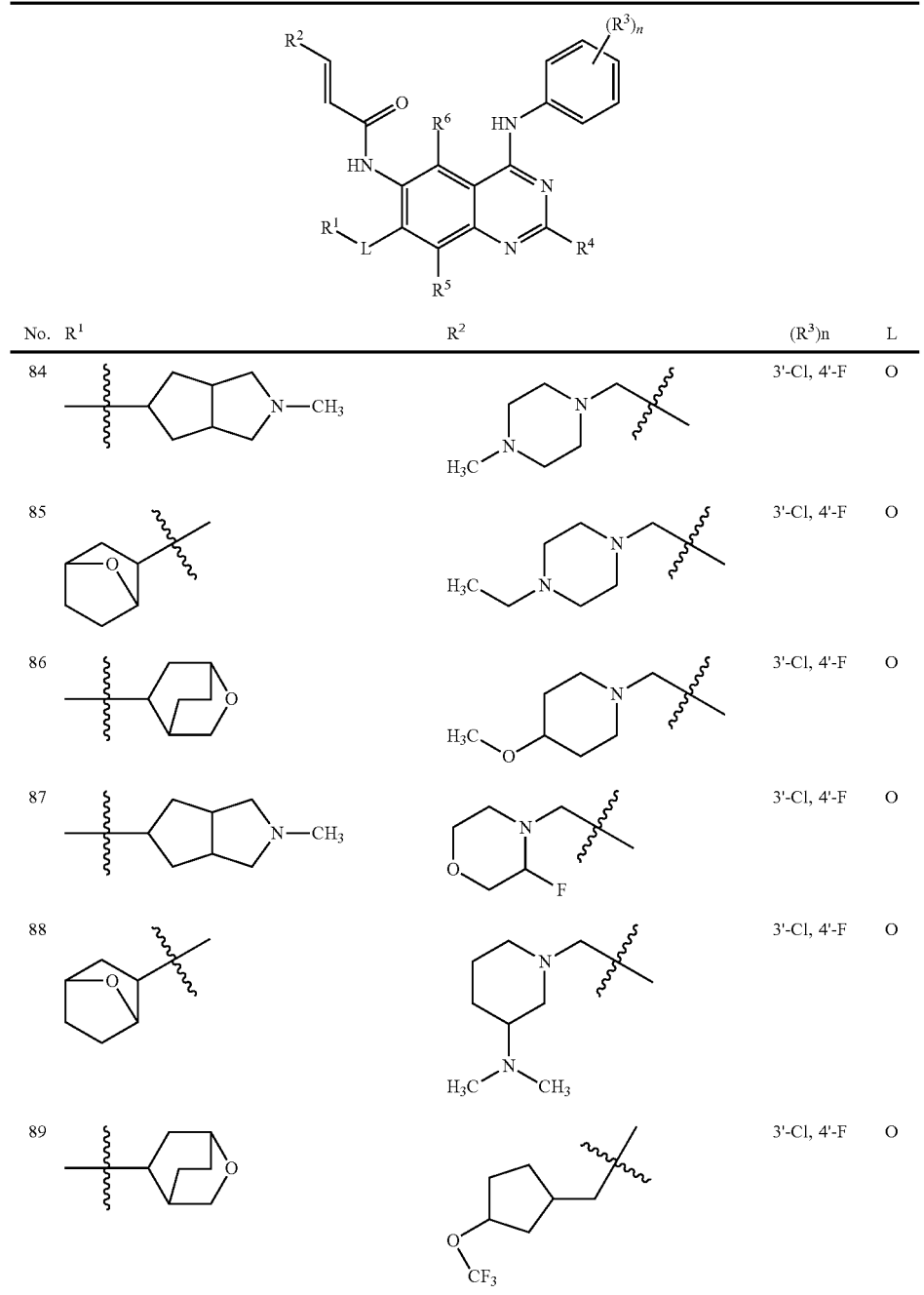

II. In Vitro Assays for the Antineoplastic Activities of the Present Compounds

Hereinafter, the beneficial effects of the present compounds will be illustrated by in vitro enzyme inhibitory activity and in vitro cellular inhibitory activity. However, it should be noted that the beneficial effects of the present compounds are not limited to the effects as illustrated below.

Assay 1
In Vitro Enzyme Inhibitory Activity of the Present Compounds
Samples:
Controls: Gefitinib, erlotinib hydrochloride, purchased from Anqing worldchem Co., LTD.; lapatinib ditosylate, purchased from Taizhou Xingcheng Chempharm Co., Ltd.; CI-1033 hydrochloride, purchased from Shanghai hanxiangchem, Co., Ltd.; and The present compounds: lab-made, their chemical names and structural formulae are shown in the preparation examples.

Assay Procedures:
The abbreviations used in the following assay have the following meanings:
HEPES: hydroxyethyl piperazine ethanesulfonic acid;
Brij-35: polyoxyethylene lauryl ether;
DTT: dithiothreitol;
Coating Reagent #3: #3 coating agent;

EDTA: ethylene diamine tetraacetic acid, purchased from Sigma Co. Ltd.;
FAM labeled peptide: fluorescein labeled peptide 22 (GL Biochem);
ATP: adenosine triphosphate (Sigma);
DMSO: dimethyl sulfoxide;
EGFR: human epidermal growth factor receptor (Carna);
HER2: human epidermal growth factor receptor 2 (Carna);
HER4: human epidermal growth factor receptor 4 (Carna).
1. Formulating the agents to be used in the assay
(1) 1.25-fold $MnCl_2$-free kinase buffer (62.5 mM HEPES, PH 7.5, 0.001875% Brij-35, 12.5 mM $MgCl_2$, 2.5 mM DTT);
(2) 1.25-fold $MnCl_2$-containing kinase buffer (62.5 mM HEPES, pH 7.5, 0.001875% Brij-35, 12.5 mM $MgCl_2$, 12.5 mM $MnCl_2$, 2.5 mM DTT);
(3) Stop buffer (100 mM HEPES, pH 7.5, 0.015% Brij-35, 0.2% Coating Reagent #3, 50 mM EDTA);
(4) 2.5-fold kinase solutions (to the 1.25-fold kinase buffers were added the corresponding kinases to formulate 2.5-fold EGFR, HER2, HER4 kinase solutions);
(5) 2.5-fold peptide solutions (to the 1.25-fold kinase buffers were added FAM labeled peptide and ATP to formulate the peptide solutions);
(6) 5-fold compound solutions (using 100% DMSO to formulate 50-fold compound solutions having different concentration gradients, and diluting with water by 10 times to obtain 5-fold compound solutions having different concentration gradients);
2. Adding 5 μL of a 5-fold compound solution to a 384-well plate;
3. Adding 10 μL of a 2.5-fold kinase solution to incubate for 10 min;
4. Then adding 10 μL of a 2.5-fold peptide solution, and reacting at 28° C. for 1 h; and
5. Finally, adding 25 μL of stop buffer to terminate the reaction, and reading the data with Caliper.
6. Curve fitting to obtain an $IC_{50}$ value.

The calculated inhibition ratio (%)=(the maximum conversion rate−the conversion rate)/(the maximum conversion rate−the minimum conversion rate)×100

The curve fitting was conducted with the Xlfit software to obtain $IC_{50}$ values.
The results are shown below.

TABLE 1

In vitro enzyme inhibitory activity

| Compound | Enzyme inhibitory activity $IC_{50}$(nM) | | |
| --- | --- | --- | --- |
| | EGFR | HER2 | HER4 |
| Gefitinib | 1.6 | 318 | 7.6 |
| Erlotinib hydrochloride | 1.3 | 454 | 49 |
| Lapatinib ditosylate | 16 | 4.0 | 250 |
| CI-1033 hydrochloride | 0.46 | 4 | 2.2 |
| Compound 6 | 1 | 7.1 | 1.4 |
| Compound 7 | 0.93 | 4.3 | 1.7 |
| Compound 8 | 0.66 | 6.5 | 3.4 |
| Compound 11 | 0.8 | 12 | 8.3 |
| Compound 14 | 0.39 | 2.6 | 1.2 |
| Compound 18 | 1 | 6.5 | 1.9 |
| Compound 19 hydrochloride | 0.56 | 3.1 | 3.7 |

Conclusion:

It can be seen from table 1 that the present compounds have stronger inhibitory activities on EGFR, HER2, HER4 kinases, and are comparable with CI-1033 hydrochloride in activity; the present compounds have a remarkably better inhibitory activity on the HER2 kinase than gefitinib and erlotinib hydrochloride; and the present compounds have a remarkably better inhibitory activity on the HER4 kinase than erlotinib hydrochloride and lapatinib ditosylate.

Assay 2

In Vitro Cellular Inhibitory Activity of the Present Invention Samples:

Controls: Gefitinib, erlotinib hydrochloride, purchased from Anqing worldchem Co., LTD. Anqing worldchem Co., LTD.; lapatinib ditosylate, purchased from Taizhou Xingcheng Chempharm Co., Ltd.; CI-1033 hydrochloride, purchased from Shanghai hanxiangchem, Co., Ltd.; and The present compounds: lab-made, their chemical names and structural formulae are shown in the preparation examples.

Assay Procedures:

The abbreviations used in the following assay have the following meanings:

XTT: 3,3'-Sodium [1-(carbaniloyl)-3,4-tetrazolium]-di(4-methoxy-6-nitro)benzenesulfonate/2,3-Bis-(2-methoxy-4-nitro-5-sulfophenyl]-2H-tetrazolium-5-carboxyanilide salt, purchased from Amresco Ltd.;

RPMI1640: a medium designed by Roswell Park Memorial Institute; purchased from Hyclone Company;

FBS: fetal calf serum, purchased from Hyclone Company;

PBS: phosphate buffer, purchased from Homemade Company.

1. Formulating the Agents and the Compounds

1) Formulating PBS:

NaCl (8 g), KCl (0.2 g), $Na_2HPO_4$ (1.44 g), and $KH_2PO_4$ (0.24 g) were added to ultrapure water (800 mL). After adjusting the pH to 7.4, ultrapure water was further added until the volume reached 1 L. The mixture was autoclaved for 20 min.

2) Formulating the XTT Working Liquor:

XTT powder (100 mg) was taken and, while being kept in darkness, dissolved into 300 ml of the serum-free RPMI1640 culture medium that was warmed to 50° C. and did not contain phenol red. The mixture was filtered, packaged separately, and used immediately or within one week. It is necessary for all of the processes to be kept in darkness.

3) Formulating Test Compounds

Formulating a Stock Solution of Test Compound:

The compound powder was dissolved into DMSO until a concentration of 10 mM reached.

Formulating Gradient Dilute Solutions of Test Compound:

First, the 10 mM stock solution of test compound was diluted with DMSO in a 4-fold successive gradient for 10 concentrations. 2 μL DMSO-diluted compound was added to 998 μL of the culture medium containing 10% FBS. Therefore, the maximum concentration of the compound is 20 μM, the concentration of DMSO is 0.2%, and there are 10 concentration gradients in total.

2. Culturing Cells

1) Thawing Cells:

A cell-freezing tube was removed from liquid nitrogen, and placed in a water bath of 37° C.-39° C. to thaw the cells quickly.

A freezing-preserving solution was transferred to 15 ml sterile centrifuge tube, to which was added a culture medium in a volume 10 times larger than that of the freezing-preserving solution. The mixture was centrifuged at 1000 rpm at 4° C. for 5 min. The culture medium in the centrifuge tube was discarded, and then a culture medium containing 10% FBS was added. The cells were resuspended and transferred to the culture bottle. On the next day, the solution was changed.

2) Passing Cells

For the logarithmic growth phase cells, the culture medium was discarded and an appropriate volume of PBS was added to wash the cells once. Then an appropriate volume of a digestive juice containing 0.25% pancreatic enzyme and 0.02% EDTA was added. The solution was placed on stand at 37° C. for 2-5 min, and then washed once with PBS after the digestive juice was discarded. An appropriate volume of a culture medium containing 10% FBS was added to terminate the digestion. The pipette was blown and hit slightly, and the cells were digested down to produce a cell suspension for cell passage and further experiment.

3) Freezing and Preserving Cells

For the logarithmic growth phase cells, a digestive juice containing 0.25% pancreatic enzyme and 0.02% EDTA was used to digest cells to produce a cell suspension. The suspension was centrifuged at 1000 rpm at 4° C. for 5 min. The culture medium was discarded and a freezing-preserving solution containing 10% DMSO and 90% FBS was added to resuspend the cells. The cells were packaged separately in the cell-freezing tubes in $2 \times 10^6$ cells/tube. The cell-freezing tubes were placed in a programmed cooling cassette, kept at −80° C. for 24 hours, and then transferred to liquid nitrogen for freezing and preserving.

3. Plating Cells

1) Preparing the cell suspension

The culture medium was removed from the culture bottle. The cells were rinsed twice with PBS. The pancreatic enzyme was added to digest cells. The digested cells were collected by centrifuge. The cells were resuspended with a culture medium containing 10% fetal calf serum, counted and adjusted to an appropriate concentration (the cell viability should be over 90%). The cell concentration was $5 \times 10^4$/ml.

2) The cell suspension was added to the 96-well plate, 100 μL per well.

3) The plate was placed in the incubator and incubated at 37° C. under 5% $CO_2$ overnight.

4. Treating with Drugs

Drugs were added to the cell culture plate. The plate was placed in the incubator and incubated at 37° C. under 5% $CO_2$ for 72 hours.

5. Testing the Cell Viability with the XTT Method

The XTT working solution was added to the plate. The plate was placed in the incubator and incubated at 37° C. under 5% $CO_2$ for 2 hr. Then the plate was placed in a microplate reader to read the absorbance at 450 nm.

6. Data Processing

1) The percent inhibition was calculated by the following calculation.

% inhibitor=(Absorbance(medium)−Absorbance(Compound))/(Absorbance(medium)−Absorbance(positive control)×100%;

2) Data were input into GraphPad Prism 5.0 to plot a curve and obtain $IC_{50}$.

Result:

Table 2 in vitro cellular inhibitory activities on H1975 (NSCLC, nonsmall-cell lung cancer)

| H1975 Cells | |
|---|---|
| Compound | $IC_{50}$ (nM) |
| erlotinib hydrochloride | 3985.0 |
| lapatinib ditosylate | 4534.0 |
| CI-1033 hydrochloride | 157.3 |
| Compound 8 | 305.6 |
| Compound 18 | 92.3 |
| Compound 19 hydrochloride | 104.5 |

Table 3 in vitro cellular inhibitory activities on Calu-3 (NSCLC nonsmall-cell lung cancer)

| Calu-3 Cells | |
|---|---|
| Compound | $IC_{50}$ (nM) |
| erlotinib hydrochloride | 1319.0 |
| lapatinib ditosylate | 94.3 |
| CI-1033 hydrochloride | 685.6 |
| Compound 18 | 38.2 |

Table 4 in vitro cellular inhibitory activities on A431 (Epidermoid carcinoma)

| A431 cells | |
|---|---|
| Compounds | $IC_{50}$ (nM) |
| erlotinib hydrochloride | 1269.0 |
| lapatinib ditosylate | 3282.0 |
| CI-1033 hydrochloride | 402.4 |
| Compound 19 hydrochloride | 114.0 |

Note: The cells H1975, Calu-3 and A431 used in the above assay were available from Chinese Vendor.

Conclusions:

It can be seen from Table 2 that the cellular proliferation inhibition effect of the present compounds on H1975 (NSCLC, nonsmall-cell lung cancer) is remarkably superior to erlotinib hydrochloride and lapatinib ditosylate.

It can be seen from Table 3 that the cellular proliferation inhibition effect of the present compounds on Calu-3 (NSCLC, nonsmall-cell lung cancer) is superior to lapatinib ditosylate, and remarkably superior to erlotinib hydrochloride and CI-1033 hydrochloride.

It can be seen from Table 4 that the cellular proliferation inhibition effect of the present compounds on A431 (Epidermoid carcinoma) is superior to CI-1033 hydrochloride, and remarkably superior to erlotinib hydrochloride and lapatinib ditosylate.

Assay 3-1 In Vitro Cellular Inhibitory Activities on Bladder Carcinoma of the Compound of the Present Invention Material Samples:

Compound 18, lab-made. See the chemical name, structural formula and preparation method of the compound in the preparation examples of the present invention.

Control Drug:

AZD9291 is purchased or lab-made according to the existing technique and method with the following structural formula.

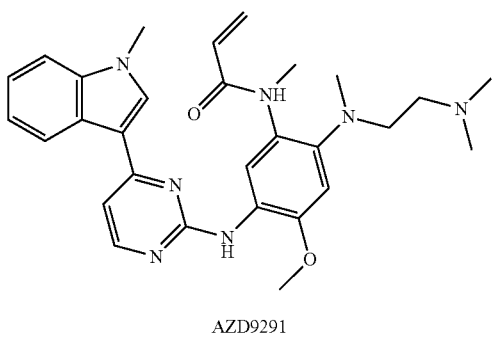 [SMILES: C=CC(=O)N(C)c1cc(Nc2nccc(-c3cn(C)c4ccccc34)n2)c(OC)cc1N(C)CCN(C)C]

AZD9291

Method

The effect of the compound to be tested on 5637 (bladder carcinoma) cell proliferation was tested using CTG kit.

1. Formulating the Compounds

535 µl DMSO was added into an EP tube filled with 3.32 mg of Compound 18 and evenly shaken (10 mM);

590 µl DMSO was added into an EP tube filled with 3.16 mg of Compound AZD9291 and evenly shaken (10 mM);

Formulating a stock solution of a 1000-fold compound:

The compound was diluted with DMSO by 4-fold from 10 mM to 2.5 mM, 625 µM, 156 µM, 39 µM, 9.8 µM, 2.4 µM, 0.61 µM, 0.15 µM, 0.04 µM in turn.

Formulating a stock solution of a 10-fold compound: 2 µl 1000-fold Compound 18 or AZD9291 was respectively added into a 198 µl culture medium and evenly shaken.

2. Method for Culturing Cells

The specific cell culture method is the same as Assay 2.

3. Plating Cells

1) Preparing cell suspension a The culture medium was removed from the culture bottle;

b The cells were rinsed twice with PBS;

c The pancreatic enzyme was added to digest cells. The digested cells were collected by centrifuge;

d The cells were resuspended with a culture medium containing 10% fetal bovine serum, counted and adjusted to an appropriate concentration;

2) The cell suspension was added to the 384-well plate, with 22.5 µl per well.

3) The plate was placed in the incubator and incubated at 37° C. under 5% $CO_2$ overnight.

4. Treating with Drugs

1) Plating in the 384-well plate with 250 cells/well/22.5 ul;

2) After 24 hours, each well was added with 2.5 ul 10-fold drug which was well diluted to make the final concentration of 10 µM, 2.5 µM, 625 nM, 156 nM, 39 nM, 9.8 nM, 2.5 nM, 0.610 nM, 0.153 nM, 0.04 nM.

3) The plate was placed in the $CO_2$ incubator and incubated at 37° C. for 72 hours 5. Testing the Cell Viability with the CTG Method 1) Formulating CellTiter-Glo® agent.

2) Each well was added with 25 ul CellTiter-Glo® agent, mixed for 2 minutes and placed at room temperature while being kept in darkness for 10 minutes.

3) Reading the absorbance using EnVision 2104 Multi-label Reader.

6. Data Processing

1) The percent inhibition was calculated by the following calculation:

% inhibition=(Absorbance(medium)−Absorbance (Compound))/(Absorbance(medium)−Absorbance(blank control))×100%;

wherein the medium group was free of the compound to be tested; the blank control group was free of cells (replaced with a pure culture medium) and the compound to be tested. The other test conditions for the medium group and the blank control group were the same as the compound group.

2) Data were input into GraphPad Prism 5.0 to plot a curve and obtain $IC_{50}$.

Result

TABLE 5

Inhibitory activities on 5637 cells of the present compound

| 5637 Cells | |
|---|---|
| Compound | $IC_{50}$ (nM) |
| Compound 18 | 38.6 |
| AZD9291 | 282.5 |

Conclusion

The cellular proliferation inhibitory effect of Compound 18 of the present application on 5637 (bladder carcinoma) is superior to control AZD9291.

Assay 3-2 In Vitro Cellular Inhibitory Activity on Mammary Cancer of the Compound of the present Invention Material Samples:

Compound 18, lab-made, its chemical name, structural formula and the preparation method are shown in the preparation examples.

Controls:

Erlotinib is purchased or lab-made according to the existing technique and method with the following structural formula shown in the background art.

BT474 cells (human breast ductal carcinoma cell, purchased from ATCC).

Method

1. Formulating the Agents and the Compounds

1) Formulating XTT Solution

The formulating method is the same as in Assay 2.

2) Formulating the Compound a Formulating a stock solution of test compound: the compound powder was dissolved into DMSO until a concentration of 10 mM reached.

b Formulating gradient dilute solutions of test compound: First, the 10 mM stock solution of test compound was diluted with DMSO in a 2.5-fold gradient, i.e., the achieved concentration is 4 mM. Then it was diluted with DMSO in a 4-fold successive gradient. There were 10 concentration gradients in total. 2 µL DMSO-diluted compound each was added to 198 µL of the culture medium containing 10% FBS respectively. Therefore, the maximum concentration of the compound to be tested is 40 µM and the concentration of DMSO is 1%.

2. Method for Culturing Cells

The specific method for culturing cells is the same as Assay 2.

3. Plating Cells

1) Preparing the cell suspension a The culture medium was removed from the culture bottle;

b The cells were rinsed twice with PBS;

c The pancreatic enzyme was added to digest cells. The digested cells were collected by centrifuge;

d The cells were resuspended with a culture medium containing 10% fetal bovine serum, counted and adjusted to an appropriate concentration;

2) The cell suspension was added to the 96-well plate with 150 μl per well.

3) The plate was placed in the incubator and incubated at 37° C. under 5% $CO_2$ overnight.

4. Treating with Drugs

1) Each well was added 50 μl growth medium containing 10% FBS; and 50 μl diluted compound was added into the well. The maximum concentration of the test compound was 10 μM, and there were 10 concentration gradients in total. For each compound, the operation was duplicated. The final concentration of DMSO was 0.25%.

2) The plate was placed in the $CO_2$ cell incubator and incubated at 37° C. for 72 hours.

5. Testing the Cell Viability with the XTT Method

1) Formulating XTT test working solution

2) The culture medium was removed; each well was added with 150 μl XTT working solution.

3) The plate was placed in the incubator and incubated at 37° C. under 5% $CO_2$ for 1-5 hours.

4) Slightly and evenly shaking before reading the absorbance. Then the plate was placed in a microplate reader to read the absorbance at 450 nm.

6. Data Processing

1) The percent inhibition was calculated by the following calculation:

% inhibition=(Absorbance(medium)−Absorbance (Compound))/(Absorbance(medium)−Absorbance(blank control))×100%;

2) Data were input into GraphPad Prism 5.0 to plot a curve and obtain $IC_{50}$.

Result

TABLE 6

Inhibitory activities on BT474 cell of the compound of the present invention
BT474

| Compound | $IC_{50}$ (nM) |
| --- | --- |
| Compound 18 | 9.7 |
| Erlotinib | 5430.0 |

Conclusion

The compound of the present invention plays a good role in cellular proliferation activity inhibition on BT474 human breast ductal carcinoma cell and the inhibition effect is remarkably superior to control Erlotinib.

Assay 3-3 In Vitro Cellular Inhibitory Activities on NCI-N87 (Gastric Carcinoma) of the Compound of the Present Invention The Material and Method Samples:

Compound 18, lab-made, its chemical name, structural formula and preparation method are shown in the preparation examples.

Controls:

Erlotinib and Lapatinib are purchased or lab-made according to the existing technique and method with the following structural formula shown in the background art.

Method

1. Formulating the Agents

1) Formulating the XTT Solution

The formulating method is the same as Assay 2.

2) Formulating the Compound a Formulating a stock solution of test compound: the compound powder was dissolved into DMSO until a concentration of 10 mM reached.

b Formulating gradient dilute solutions of test compound: first, the 10 mM stock solution of test compound was diluted with DMSO in a 4-fold successive gradient, and there are 10 concentration gradients in total. 2 μL DMSO-diluted compound each was added to 198 μL of the culture medium containing 10% FBS respectively. Therefore, the maximum concentration of the compound to be tested is 40 μM, the concentration of DMSO is 1%.

2. Method for Culturing Cells

The method for culturing cells is the same as Assay 2.

3. Plating Cells

The method for plating cells is the same as Assay 3-2.

4. Treating with Drugs 1) 50 μl of the above diluted compound was added into each well of the cell culture plate. The maximum concentration of the test compound was finally made 10 m and there are 10 concentration gradients in total. For each compound, the above operation was triplicated. The final concentration of DMSO was 0.25%.

2) The plate was placed in the $CO_2$ incubator and incubated at 37° C. for 72 hours.

5. Testing the Cell Viability with the XTT Method

1) Formulating the XTT test working solution

2) The culture medium was removed and each well was added with 150 μl XTT working solution.

3) The plate was placed in the incubator and incubated at 37° C. under 5% $CO_2$ for 1-5 hours.

4) Slightly and evenly shaking before reading the absorbance. Then the plate was placed in a microplate reader to read the absorbance at 450 nm.

6. Data Processing

1) The percent inhibition was calculated by the following calculation:

% inhibition=(Absorbance(medium)−Absorbance (Compound))/(Absorbance(medium)−Absorbance(blank control))×100%

2) Data were input into GraphPad Prism 5.0 to plot a curve and obtain $IC_{50}$.

Result

TABLE 7

Inhibitory activities on NCI-N87 (gastric carcinoma) of the compound of the present invention
NCI-N87 cell

| Compound | $IC_{50}$ (nM) |
| --- | --- |
| Compound 18 | 7.1 |
| Erlotinib | 2108.0 |
| Lapatinib | 11.9 |

Conclusion

It can be seen from Table 7 that the compound of the present invention is remarkably superior to control Erlotinib and slightly superior to control Lapatinib in terms of inhibitory effect on NCI-N87 (gastric carcinoma) cellular proliferation. It exhibits superior cellular proliferation inhibitory activity.

Assay 4 In Vivo Antitumor Activity of the Compound of the Present Invention

Assay 4-1 In Vivo Pharmacodynamic Evaluation on Bladder Carcinoma of the Compound of the Present Invention Material Samples:

Compound 18. See the chemical name, structural formula and preparation method of the compound in the preparation examples of the present invention.

Control Drugs:

Neratinib and Lapatinib are purchased or lab-made according to the existing technique and method; the structural formula of Lapatinib is as mentioned in the background art; the structural formula of Neratinib is as follows:

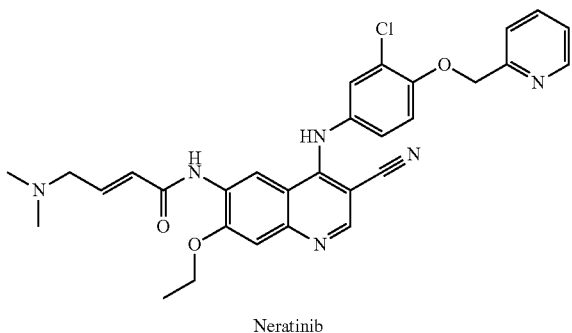 [SMILES: CCOc1cc2ncc(C#N)c(Nc3ccc(OCc4ccccn4)c(Cl)c3)c2cc1NC(=O)/C=C/CN(C)C]

Neratinib

Experimental animal: BALB/c nude mice purchased from Beijing Huafukang Bioscience Co. Ltd.

Method

Animal Modeling and Grouping:

5637 (bladder carcinoma) cells were cultured in RPMI1640 culture medium containing 10% FBS. 5637 cells in exponential phase of growth were collected and were resuspended to an appropriate concentration with PBS. The tumor was inoculated subcutaneously on the right side of the nude mice's back.

The growth of the tumor was observed regularly. When the tumor grew to an average of about 100 mm³, the mice were randomly grouped and administrated according to the size of the tumor and the weight of the mice. The experiment was divided into treatment group of sample compound 18 (30 mg/kg, 20 mg/kg and 10 mg/kg), treatment group of positive control Neratinib and treatment group of positive control Lapatinib and medium control group (sterile water for injection). There were 8 animals in each group which were orally intragastrical administered once a day. They were administered totally 32 times. The tumor volume (TV) was measured with an ernier caliper. In the whole process of the experiment, the weight and tumor size of the mice were measured twice a week. The efficacy was evaluated according to the relative tumor growth inhibition (TGI) value.

Experimental Observation Index and Calculation:

tumor volume $TV=0.5 \, a \times b^2$, wherein a is the long diameter and b is the short diameter of the tumor.

Relative Tumor Growth Inhibition $TGI (\%)=(1-T/C)\times 100\%$. T and C are respectively the relative tumor volume (RTV) at a certain point-in-time of the treatment group and control group.

T/C % is the relative tumor proliferation rate, i.e., the percentage ratio of relative tumor volume of the treatment group to that of control group at a certain point-in-time. The calculation formula is as follows: $T/C \% = T_{RTV}/C_{RTV} \times 100\%$ ($T_{RTV}$: the mean RTV of the treatment group; $C_{RTV}$: the mean RTV of the medium control group; $R_{TV}=V_t/V_0$, $V_0$ is the tumor volume of the animal at the time of grouping and Vt is the tumor volume of the animal after treatment).

Statistical Method:

All the experiment results were represented by the average tumor volume±SE (Standard Error) and analyzed by means of the test method of one way ANOVA. All the data were analyzed using SPSS 18.0. p<0.05 represents significant difference.

Result:

TABLE 8

The TGI and T/C value of each group in 5637 human bladder carcinoma model

| | | 32 days after the adminstration | | | | |
|---|---|---|---|---|---|---|
| Experimental Groups | Dosage | Tumor Volume (mm³) | Relative Tumor Volume | TGI (%) | T/C (%) | P Value (Comparison with the control group) |
| Medium control | — | 319 ± 38 | 3.21 ± 0.44 | — | — | — |
| Compound 18 | 30 mg/kg | 45 ± 9 | 0.43 ± 0.08 | 87 | 13 | 0.005 |
| | 20 mg/kg | 49 ± 7 | 0.51 ± 0.08 | 84 | 16 | 0.006 |
| | 10 mg/kg | 64 ± 21 | 0.68 ± 0.22 | 79 | 21 | 0.007 |
| Neratinib | 80 mg/kg | 61 ± 6 | 0.60 ± 0.05 | 81 | 19 | 0.008 |
| Lapatinib | 200 mg/kg | 41 ± 7 | 0.41 ± 0.07 | 87 | 13 | 0.005 |

Conclusion

Compound 18 has significant antitumor effect on 5637 human bladder carcinoma model under all the conditions set by the present experiment and is remarkably superior to the control drugs. The mice with tumor can tolerate Compound 18 in each tested dosage.

Assay 4-2 In Vivo Pharmacodynamic Evaluation on Esophageal Carcinoma of the Compound of the Present Invention Material Samples:

Compound 18. See the chemical name, structural formula and preparation method of the compound in the preparation examples of the present invention.

Experimental Animals:

BALB/c nude mice, 6-8 weeks (weeks of age of the mice upon tumor cell inoculation) purchased from Beijing Huafukang Bioscience Co. Ltd.

Method

Animal Modeling and Grouping:

KYSE270 cells were cultured in RPMI1640 culture medium containing 10% FBS. KYSE270 (esophageal carcinoma) cells in exponential phase of growth were collected. After the cells were resuspended to an appropriate concentration with PBS, $1\times 10^7$ KYSE270 cells were inoculated subcutaneously on the right side of the female mice's back.

When the tumor grew to an average of about 123 mm³, the mice were randomly grouped according to the size of the tumor. The experiment was divided into treatment group of sample compound 18 (10 mg/kg and 20 mg/kg) and the medium control group (sterile water for injection). There were 8 animals in each group which were orally intragastrical administered once a day. They were administered totally 21 times. The tumor volume (TV) was measured with an ernier caliper. The weight and tumor size of the mice were measured twice a week. The efficacy was evaluated according to the relative tumor growth inhibition (TGI).

Experimental Observation Index and Calculation:
The calculation formulae for the tumor volume (TV), relative tumor growth inhibition TGI and relative tumor proliferation rate T/C (%) are the same as Assay 4-1.

Statistical Method:
All the experiment results were represented by the average tumor volume±SE (Standard Error) and analyzed by means of the test method of one way ANOVA. All the data were analyzed using Games-Howell (heterogeneity of variance) for comparing the significant differences between the tumor volume and tumor weight of the control group and each treatment group. $p<0.05$ represents significant difference.
Result:

TABLE 9

The TGI and T/C value of each group in KYSE270 human esophageal carcinoma model

| | | 21 days after the adminstration | | | | |
|---|---|---|---|---|---|---|
| Experimental Groups | Dosage | Tumor Volume $(mm^3)$ | Relative Tumor Volume | TGI (%) | T/C (%) | P Value (Comparison with the control group) |
| Medium control | — | 1974 ± 116 | 16.66 ± 1.54 | — | — | — |
| Compound 18 | 10 mg/kg | 40 ± 6 | 0.33 ± 0.05 | 98 | 2 | <0.001 |
| Compound 18 | 20 mg/kg | 14 ± 3 | 0.11 ± 0.02 | 99 | 1 | <0.001 |

Conclusion
Compound 18 has significant antitumor effect on KYSE270 human esophageal carcinoma model under both the conditions of 10 mg/kg and 20 mg/kg. The mice with tumor can tolerate the tested drugs well.

Assay 4-3 In Vivo Pharmacodynamic Evaluation on Head and Neck Cancer of the Compound of the Present Invention
Material
Samples:
Compound 18. See the chemical name, structural formula and preparation method of the compound in the preparation examples of the present invention.

Control Drugs:
Neratinib is purchased or lab-made according to the existing technique and method; the structural formula is mentioned in Assay 4-1.
HN2170, head and neck cancer from a 63-year-old Asian male patient.
Animals
BALB/c nude mice, 6-8 weeks purchased from Beijing Huafukang Bioscience Co. Ltd.
Agents
Methyl Cellulose, MC (Cat. No.: 9004-67-5, SIGMA);
Tween 80 (Cat. No.: 9005-64-5, Amresco).
Method
Animal Modeling and Grouping:
Tumor tissues were collected from mice with tumor of human-derived xenograft model HN2170 and cut into tumor blocks of a diameter of 2-4 mm which were then inoculated subcutaneously on the right anterior portion of the mice. When the average tumor volume reached about 100-150 $mm^3$, the mice were grouped randomly and the day for grouping was recorded as Day 0. The mice were divided into three experimental groups including the 20 mg/kg group of test Compound 18, 80 mg/kg group of Neratinib and vehicle medium group (0.5% MC/0.4% Tween 80 sterile aqueous solution for injection). In each group there were 4 animals which were orally intragastrical administered once a day. They were administered totally 25 days. The tumor volume (TV) was measured with an ernier caliper twice a week.

Experimental Observation and Calculation
The calculation formulae for the tumor volume (TV), relative tumor growth inhibition TGI and relative tumor proliferation rate T/C (%) are the same as Assay 4-1.
Result

TABLE 10

Inhibitory effect on treating xenograft model HN2170 of the compound of the present invention

| | | Tumor Volume | 25 days after the adminstration | | |
|---|---|---|---|---|---|
| Experimental Groups | Dosage | $(mm^3)^a$ (Day 0) | Tumor Volume $(mm^3)^a$ | T/C (%) | TGI (%) |
| Medium control | — | 142.7 ± 22.4 | 783.6 ± 262.4 | — | — |
| Compound 18 | 20 mg/kg | 143.1 ± 22.9 | 46.3 ± 10.6*** | 6.5 | 93.5 |
| Neratinib | 80 mg/kg | 142.4 ± 23.4 | 53.7 ± 10.3*** | 7.2 | 92.8 |

Notes:
$^a$Mean ± standard error;
***$P < 0.001$, Comparison with the control group Conclusion Test compound 18 of the present experiment has significant tumor growth inhibitory effect on human-derived xenograft model HN2170 and the inhibitory effect is superior to the Neratinib control.

Assay 4-4 In Vivo Pharmacodynamic Evaluation on Mammary Cancer of the Compound of the Present Invention Material Samples:

Compound 18. See the chemical name, structural formula and preparation method of the compound in the preparation examples of the present invention.

Controls:

Lapatinib is purchased or lab-made according to the existing technique and method; the structural formula is mentioned in the background art.

Experimental Animals:

BALB/c-nude mice of 6-7 weeks purchased from Shanghai SLAC Laboratory Animal Co., Ltd.

Method

Human breast cancer BT-474 purchased from American Type Culture Collection (ATCC) was cultured with DMEM culture medium containing 10% FBS.

After the cells were collected by centrifuge, the cells were inoculated subcutaneously on the nude mice ($9 \times 10^6$ cells/mouse). When the tumor grew to 100-200 mm$^3$, the animals were divided into four groups randomly including 20 mg/kg group and 10 mg/kg group of Compound 18, 200 mg/kg group of Lapatinib and vehicle medium group (10% Hydroxypropyl beta cyclodextrin). There were 8 animals in each group which were orally intragastrical administered once a day. The day for grouping was recorded as Day 0 (DO). They were administered totally 21 times. The tumor volume was measured with an ernier caliper twice a week and the data were recorded.

Experimental Observation Index and Calculation:

The calculation formulae for the tumor volume (TV), relative tumor growth inhibition TGI and relative tumor proliferation rate T/C (%) are the same as Assay 4-1.

Statistical Method:

The significant differences in RTV between the treatment groups and the control groups were tested using t test. In case of heterogeneity of variance between the samples, t' test was used for testing. $P<0.05$ indicates significant differences.

Result:

Conclusion

Compound 18 significantly inhibits the growth of HER2-high expression human breast cancer BT-474 nude mice transplanted tumor in each tested dosage. The inhibitory effect is significantly superior to the Lapatinib control. The mice with tumor can tolerate Compound 18 well.

Assay 4-5 In Vivo Pharmacodynamic Evaluation on Gastric Cancer of the Compound of the Present Invention Material Samples:

Compound 18. See the chemical name, structural formula and preparation method of the compound in the preparation examples of the present invention.

Experimental Animal:

BALB/c nude mice of 6-8 weeks purchased from Beijing Anikeeper Biosciece Co. Ltd.

Method

Animal Modeling and Grouping:

NCI-N87 tumor cells (purchase from ATCC) was cultured with RPMI-1640 culture medium containing inactivated 10% FBS, 100 U/ml penicillin, 100 µg/ml streptomycin and 2 mM glutamine. After the tumor cells in logarithmic growth phase were resuspended with RPMI1640 free of serum, the cells were inoculated subcutaneously in the right coastal region of the experimental animals in an appropriate concentration.

When the tumor grew to about 150 mm$^3$, the mice were grouped and administrated. There were 2 groups in total, each with 8 mice, including solvent control group (sterile water for injection) and treatment group of Compound 18. The dosage was 20 mg/kg and the day for grouping was recorded as Day 0 (DO). The mice were orally intragastrical administered once a day and totally administered for 28 days. The size of the tumor was measured twice a week. The relationship between the mice tumor volume and the administration time was recorded. The tumor volume ratio (T/C) and the tumor growth inhibition (TGI) of the treatment group and solvent control group were calculated for statistical analysis.

Measurement of the Tumor and Experimental Index

The calculation formulae for the tumor volume (TV), relative tumor growth inhibition TGI and relative tumor proliferation rate T/C (%) are the same as Assay 4-1.

Statistical Method:

One-Way ANOVA test was carried out using statistical software SPSS 17.0. Inter group statistical analysis of the tumor volume was performed. $p<0.05$ represents significant difference.

TABLE 11

Efficacy on human breast cancer BT-474 nude mice transplanted tumor of the compound of the present invention

| Experimental Groups | Dosage | Mean Tumor Volume (mm$^3$) D0($\overline{X} \pm S$) | 21 days after the adminstration | | | | |
|---|---|---|---|---|---|---|---|
| | | | Mean Tumor Volume (mm$^3$) D21($\overline{X} \pm S$) | Relative Tumor Volume D21($\overline{X} \pm S$) | TGI (%) | T/C (%) | P Value (Comparison with the control group) |
| Medium control | — | 141.9 ± 6.4 | 1924.6 ± 165.4 | 13.6 ± 1.0 | — | 100 | — |
| Compound 18 | 10 mg/kg | 140.5 ± 8.0 | 447.0 ± 91.4 | 3.1 ± 0.6 | 77 | 23 | 0.000 |
| Compound 18 | 20 mg/kg | 136.7 ± 8.8 | 171.6 ± 52.9 | 1.2 ± 0.3 | 91 | 9 | 0.000 |
| Lapatinib | 200 mg/kg | 136.6 ± 7.0 | 245.8 ± 52.2 | 1.8 ± 0.4 | 87 | 13 | 0.000 |

Result:

TABLE 12

The antitumor effect on nude mice with tumor of NCI-N87 human-derived gastric cancer xenograft of the compound of the present invention

| | | 28 days after the administration | | | | |
|---|---|---|---|---|---|---|
| Experimental Groups | Dosage | Tumor Volume $(mm^3)^a$ | Tumor Relative Volume(%)$^a$ | T/C (%) | TGI (%) | P |
| Solvent control group | — | 2,359 ± 177 | 1,474 ± 70 | — | — | — |
| Compound 18 | 20 mg/kg | 358 ± 32 | 228 ± 18 | 15.4 | 84.6 | <0.001 |

Notes:
$^a$mean ± standard error;

Conclusion

Test Compound 18 treatment group plays significant inhibitory effect on the growth of tumor in the NCI-N87 human-derived gastric cancer xenograft tumor model. In the treatment, experimental animals of each group tolerated well without obvious adverse reaction.

Assay 4-6 In Vivo Pharmacodynamic Evaluation on Malignant Glioma of the Compound of the Present Invention Material
  Samples:
  Compound 18. See the chemical name, structural formula and preparation method of the compound in the preparation examples of the present invention.
  Control Drugs:
  Neratinib and Lapatinib are purchased or lab-made according to the existing technique and method; the structural formula of Lapatinib is as mentioned in the background art; the structural formula of Neratinib is mentioned in Assay 4-1.
  Experimental Animal:
  BALB/c nude of 6-8 weeks purchased from Beijing Anikeeper Biosciece Co. Ltd.

Method
  Culturing Cells
  LN-229 cancer cells were cultured with DMEM culture medium containing inactivated 10% FBS, 100 U/ml penicillin, 100 μg/ml streptomycin and 2 mM glutamine. After the tumor cells in logarithmic growth phase were resuspended with DMEM culture medium free of serum, the cells were inoculated subcutaneously in the right coastal region of the experimental animals in an appropriate concentration.
  When the tumor grew to about 100 mm$^3$, the mice were grouped and administrated. There were 6 groups in total, each with 8 mice, including solvent control group (sterile water for injection); administration groups of Compound 18 with dosages of 30 mg/kg, 20 mg/kg, and 10 mg/kg; Neratinib administration group with the dosage of 80 mg/kg; Lapatinib administration group with the dosage of 200 mg/kg. The mice were orally intragastrical administered once a day and totally administered for 28 days. The size of the tumor was measured twice a week.

Measurement of the Tumor and Experimental Index
  The calculation formulae for the tumor volume (TV), relative tumor growth inhibition TGI and relative tumor proliferation rate T/C (%) are the same as Assay 4-1.

Statistical Method:
  One-Way ANOVA test was carried out using statistical software SPSS17.0. Inter group statistical analysis of the tumor volume was performed. p<0.05 represents significant difference.

Result:

TABLE 13

The antitumor effect on nude mice with tumor of human-derived LN-229 glioblastoma xenograft of the compound of the present invention

| | | 28 days after the administration | | | |
|---|---|---|---|---|---|
| Groups | Dosage | Tumor Volume $(mm^3)^a$ | T/C (%) | TGI (%) | P Value$^b$ |
| Solvent control | — | 570 ± 39 | — | — | — |
| Compound 8 | 30 mg/kg | 121 ± 17 | 21.3 | 78.7 | <0.001 |
| Compound 18 | 20 mg/kg | 191 ± 11 | 34.0 | 66.0 | <0.001 |
| Compound 18 | 10 mg/kg | 260 ± 27 | 45.6 | 54.4 | 0.001 |
| Neratinib | 80 mg/kg | 197 ± 20 | 34.3 | 65.7 | <0.001 |
| Lapatinib | 200 mg/kg | 261 ± 42 | 45.6 | 54.4 | 0.002 |

Notes:
$^a$mean ± standard error;
$^b$Comparison with the control group.

Conclusion

Test Compound 18 has inhibitory effect on the tumor growth of mice with LN-229 in three dosages including low dosage (10 mg/kg), medium dosage (20 mg/kg) and high dosage (30 mg/kg) in the LN-229 human-derived glioblastoma xenograft model. The inhibitory effect exhibits obvious dosage-response relationship in the present administration solution.

Assay 4-7 In Vivo Pharmacodynamic Evaluation on Ovarian Cancer of the Compound of the Present Invention Material
  Samples:
  Compound 18. See the chemical name, structural formula and preparation method of the compound in the preparation examples of the present invention.
  Control Drugs:
  Erlotinib and Lapatinib are purchased or lab-made according to the existing technique and method; the structural formulae are as mentioned in the background art.
  Experimental Animals:
  BALB/c nude of 6-8 weeks purchased from Beijing Huafukang Bioscience Co. Ltd.

Method
  Animal Modeling and Grouping:
  SKOV-3 cells were cultured in McCoy's 5a culture medium containing 10% FBS, 100 U/ml penicillin, 100 μg/ml streptomycin and 2 mM glutamine. After the tumor cells in logarithmic growth phase were resuspended with PBS to an appropriate concentration, the cells were inoculated subcutaneously in the right coastal region of the experimental animals. When the tumor grew to about 1000 mm$^3$, the mice with the tumor were killed. The tumor was then stripped under sterile conditions to remove the necrotic tissues and select the well developed tumor tissues which were inoculated subcutaneously into an animal again. In this way the tumor tissues were subjected to passage for twice in the body of the mice. The tumor tissues after the second passage were cut into tissue blocks of 2×2×2 mm using scalpel blade. The tumor blocks were inoculated subcutaneously to the right coastal region of the mice with an inoculation needle.

When the tumor grew to about 100 mm$^3$, the mice were grouped and administrated. There were 5 groups in total, each with 8 mice, including solvent control group (the 10% Hydroxypropyl beta cyclodextrin formulated with water for injection); group of Compound 18 with a dosage of 20 mg/kg and group of Compound 18 with a dosage of 10 mg/kg; group of Erlotinib with a dosage of 50 mg/kg; and group of Lapatinib with a dosage of 80 mg/kg. The mice were orally intragastrical administered once a day for 14 days in total. The tumor size was measured twice a week with an ernier caliper.

Measurement of Tumor and Experimental Index:

The calculation formulae for the tumor volume (TV), relative tumor growth inhibition TGI and relative tumor proliferation rate T/C (%) are the same as Assay 4-1.

Statistical Method:

One-Way ANOVA test was carried out using statistical software SPSS 17.0. Inter group statistical analysis of the tumor volume was performed. $p<0.05$ represents significant difference.

Result:

TABLE 14

The inhibitory effect on the tumor growth of SKOV-3 human-derived xenografts model in ovarian cancer of the compound of the present invention

| Groups | Dosage | 14 days after the adminstration | | | |
|---|---|---|---|---|---|
| | | Tumor Volume (mm$^3$)$^a$ | T/C (%) | TGI (%) | P$^b$ |
| Solvent control | — | 1603 ± 160 | — | — | — |
| Compound 18 | 20 mg/kg | 540 ± 86 | 32.1 | 67.9 | 0.003 |
| Compound 18 | 10 mg/kg | 798 ± 88 | 49.1 | 50.9 | 0.023 |
| Erlotinib | 50 mg/kg | 1349 ± 142 | 83.0 | 17.0 | 0.994 |
| Lapatinib | 80 mg/kg | 1339 ± 167 | 83.4 | 16.6 | 0.997 |

Notes:
$^a$mean ± standard error;
$^b$Comparison with the control group.

Conclusion

Compound 18 of the present invention has significant inhibitory effect on the tumor growth of mice with SKOV-3 in dosage of 20 mg/kg. However, Erlotinib and Lapatinib controls do not produce significant antitumor effect in the present model.

Assay 4-8 In Vivo Pharmacodynamic Evaluation on Colon Cancer of the Compound of the Present Invention Material Samples:

Compound 18. See the chemical name, structural formula and preparation method of the compound in the preparation examples of the present invention.

Control Drug:

Neratinib is purchased or lab-made according to the existing technique and method; the structural formulae are as mentioned in Assay 4-1.

Tumor Cell:

CR0205, colorectal cancer from a 53-year-old Asian male patient.

Animals:

BALB/c nude mice of 6-8 weeks purchased from Beijing Huafukang Bioscience Co. Ltd.

Agents:

Methyl Cellulose (MC) (Cat. No.: 9004-67-5, SIGMA); Tween 80 (Cat. No.: 9005-64-5, Amresco).

Method

Tumor tissues were collected from mice with tumor of human-derived xenografts model CR0205 and cut into tumor blocks of a diameter of 2-4 mm which were then inoculated subcutaneously in the right anterior portion of the mice. When the average tumor volume reached 100-150 mm$^3$, the mice were randomly grouped, the day for grouping being recorded as Day 0. The mice were randomly divided into three experimental groups according to the tumor volume, including group of Compound 18 with a dosage of 20 mg/kg, group of Neratinib with a dosage of 80 mg/kg, and medium control group (0.5% MC/0.4% Tween 80 sterile aqueous solution for injection). There were five animals in each group which were orally intragastrical administered once a day for 23 days in total. The tumor volume (TV) was measured with an ernier caliper twice a week.

Experimental Observation and Calculation:

The calculation formulae for The tumor volume (TV), relative tumor growth inhibition TGI and relative tumor proliferation rate T/C (%) are the same as Assay 4-1.

Statistical Method:

The present experiment was analyzed with the method of One-Way ANOVA. All the data were analyzed using SPSS 17.0. $p<0.05$ represents significant difference.

Result:

TABLE 15

The inhibitory effect on CR0205 of Huprime ® xenografts model of the compound of the present invention

| Experimental groups | Dosage | Tumor Volume (mm$^3$)$^a$ (Day 0) | 23 days after the administration | | |
|---|---|---|---|---|---|
| | | | Tumor Volume (mm$^3$)$^a$ | T/C (%) | TGI (%) |
| Medium group | — | 129.2 ± 14.1 | 772.3 ± 100.7 | — | — |
| Compound 18 | 20 mg/kg | 129.5 ± 11.1 | 278.3 ± 56.1** | 34.3 | 65.7 |
| Neratinib | 80 mg/kg | 129.2 ± 11.7 | 386.8 ± 91.8* | 47.5 | 52.5 |

Notes:
$^a$mean ± standard error;
*P < 0.05,
**P < 0.01 and
***P < 0.001 Comparison with the control group.

Conclusion

Tested Compound 18 of the present invention has significant inhibitory effect on the tumor growth of human-derived xenografts model CR0205. The antitumor effect is superior to the positive control group of Neratinib. Moreover, within the 23 days of time of administration, CR0205 mice with tumors tolerated Compound 18 well.

Assay 4-9 In Vivo Pharmacodynamic Evaluation on Gallbladder Carcinoma of the Compound of the Present Invention Material Samples:

Compound 18. See the chemical name, structural formula and preparation method of the compound in the preparation examples of the present invention.

GL6899, gallbladder carcinoma from a 74-year-old Asian female patient

Animal:

BALB/c nude mice of 5-7 weeks purchased from SPF Biotech (Beijing) Co. Ltd.

Method

Tumor Inoculation and Grouping

Tumor tissues were collected from mice with tumor of human-derived xenograft gallbladder carcinoma model GL6899 and cut into tumor blocks of a diameter of 2-4 mm which were then inoculated subcutaneously in the right anterior portion of the mice. When the average tumor volume reached 100-150 mm$^3$, the mice were randomly grouped, the day for grouping being recorded as Day 0. The mice were randomly divided into two experimental groups according to the tumor volume, including group of Compound 18 with a dosage of 20 mg/kg and Vehicle medium control group (sterile water). There were five animals in each group which were orally intragastrical administered (p.o.) once a day from the grouping day for 21 days in total. The tumor volume (TV) was measured with an ernier caliper twice a week. The efficacy was evaluated according to the relative tumor growth inhibition (TGI).

Experimental Observation Index and Calculation:

The calculation formulae for the tumor volume (TV), relative tumor growth inhibition TGI and relative tumor proliferation rate T/C (%) are the same as Assay 4-1.

Statistical Analysis:

Comparison between the two groups of data was tested by independent sample t test. All the data were analyzed using SPSS 17.0. p<0.05 represents significant difference.

Result:

Conclusion

Tested Compound 18 has superior inhibitory effect on the tumor growth of gallbladder carcinoma xenografts model GL6899.

Assay 4-10 In Vivo Pharmacodynamic Evaluation on Cholangiocarcinoma of the Compound of the Present Invention Material and Method Samples:

Compound 18. See the chemical name, structural formula and preparation method of the compound in the preparation examples of the present invention.

10114, cholangiocarcinoma from a 61-year-old female patient.

Experimental Animals:

BALB/c nude mice of 6-8 weeks purchased from Shanghai SLAC Laboratory Animal Co., Ltd. (SCXK (Shanghai) 2013-0018).

Method

Tumor Inoculation and Grouping

Tumor tissues of human cholangiocarcinoma (10114) were cut into tumor blocks of volume of 3 mm×3 mm×3 mm which were inoculated subcutaneously in mice. The tumor volume was observed and measured. When the average tumor volume of the mice with tumor reached a certain volume, the mice with tumor cells were grouped and administered, the day for grouping being recorded as Day 0. The mice were randomly divided into group of Compound 18 with a dosage of 20 mg/kg and Vehicle medium group (sterile water for injection) according to the tumor volume. There were five animals in each group which were orally intragastrical administered once a day for 21 days in total. The tumor volume (TV) was measured with an ernier caliper twice a week. The efficacy was evaluated according to the tumor growth inhibition (TGI).

Experimental Observation Index and Calculation:

The calculation formulae for the tumor volume (TV), relative tumor growth inhibition TGI and relative tumor proliferation rate T/C (%) are the same as Assay 4-1.

Statistical Analysis:

The experimental data were analyzed using statistical software SPSS 20.0. The data associated with the tumor volume was analyzed with T-test. **P<0.05 compared with the control group represents significant statistical difference.

TABLE 16

The antitumor effect in HuPrime ® gallbladder carcinoma xenografts model GL6899 of the compound of the present invention

| Groups | Dosage | Tumor Volume on day 0 (mm$^3$)$^a$ | Tumor Volume after adminstration of 21 days (mm$^3$)$^a$ | T/C (%) | TGI (%) | P值$^b$ |
|---|---|---|---|---|---|---|
| Medium group | — | 135.10 ± 13.20 | 1015.05 ± 78.52 | — | — | — |
| Compound 18 | 20 mg/kg | 135.53 ± 9.60 | 26.63 ± 2.37*** | 2.6 | 97.4 | 0.000 |

Notes:
$^a$mean ± standard error;
$^b$ comparison of the tumor volume with the control group on Day 21;
**P < 0.01 and
***P < 0.001, comparison with the medium control group at the same point of time.

Result:

TABLE 17

The antitumor effect in human-derived cholangiocarcinoma (10114) xenograft model of the compound of the present invention

| Groups | Dosage | Tumor Volume On Day 0 (mm$^3$) | 21 days after the adminstration | | T/C (%) | TGI (%) |
|---|---|---|---|---|---|---|
| | | | Tumor Volume (mm$^3$) | Relative Tumor Volume (%) | | |
| Medium group | — | 139.6 ± 14.1 | 602.37 ± 85.68 | 426.39 ± 21.80 | — | — |
| Compound 18 | 20 mg/kg | 138.6 ± 8.9 | 107.53 ± 15.80*** | 77.13 ± 9.34 | 18.1 | 81.9 |

Note:
**P < 0.01,
***P < 0.001, comparison with the medium control group.

CONCLUSION

Tested Compound 18 of the present invention has superior inhibitory effect on the tumor growth in xenograft model 10114.

The invention claimed is:

1. A method of treating ovarian cancer, colorectal cancer, mammary cancer, glioma, non-small cell lung cancer, bladder carcinoma, gastric cancer, adenocarcinoma of the esophagus, esophageal squamous cell cancer, head and neck cancer, or pancreatic cancer, which comprises a step of administering a compound represented by a general formula (I), a pharmaceutically acceptable salt thereof or a stereoisomer thereof to a mammal in need thereof, wherein
R$^1$ is selected from the group consisting of:

-continued

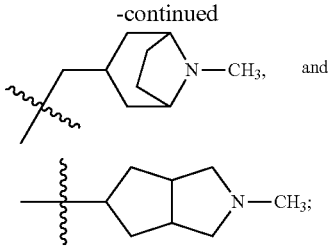

R² is selected from the group consisting of hydrogen, methyl that is unsubstituted or substituted by 1-2 Q₂ substituent(s) and ethyl that is unsubstituted or substituted by 1-2 Q₂ substituent(s), Q₂ is selected from the group consisting of:

a di(C₁₋₄alkyl)amino group, piperidinyl, piperazinyl, morpholinyl, pyrrolidinyl, furyl, cyclopropyl, cyclopentyl, pyrrolyl, pyridyl, pyrimidinyl, and thiazolyl;

R³ is selected from the group consisting of fluoro and chloro;

R⁴, R⁵, and R⁶ are hydrogen;

L is O; and n is 2.

2. A method according to claim 1, wherein

R¹ is selected from the group consisting of:

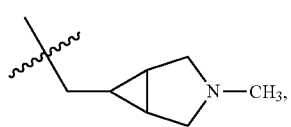

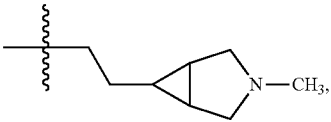

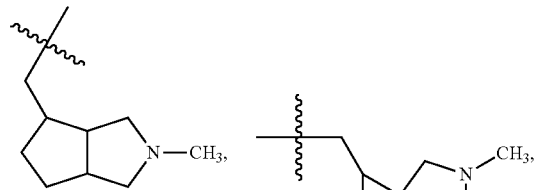

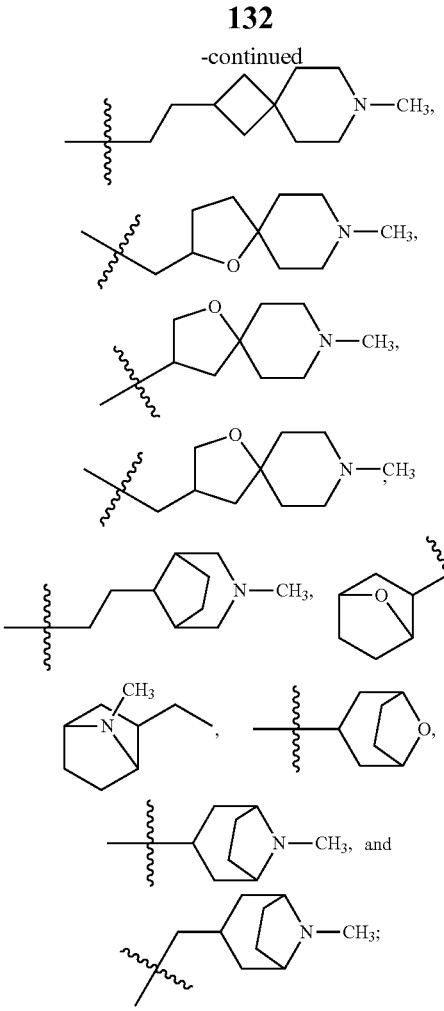

R² is selected from the group consisting of hydrogen, methyl that is unsubstituted or substituted by 1-2 Q₂ substituent(s) and ethyl that is unsubstituted or substituted by 1-2 Q₂ substituent(s), Q₂ is selected from the group consisting of dimethylamino, diethylamino, piperidinyl, piperazinyl and morpholinyl;

R³ is selected from the group consisting of fluoro and chloro;

R⁴, R⁵ and R⁶ are hydrogen;

L is O; and n is 2.

3. A method according to claim 1, wherein the compound is selected from the group consisting of:

(E)-N-[7-(8-oxabicyclo[3.2.1]octan-3-yloxy)-4-(3-chloro-4-fluorophenylamino)quinazolin-6-yl]-4-(piperidin-1-yl)-2-butenamide, (E)-N-[7-(7-oxabicyclo[2.2.1]heptan-2-yloxy)-4-(3-chloro-4-fluorophenylamino)quinazolin-6-yl]-4-(piperidin-1-yl)-2-butenamide, (E)-N-[4-(3-chloro-4-fluorophenylamino)-7-(2-methyl-2,7-diazaspiro[4.5]decan-7-yl)quinazolin-6-yl]-4-(piperidin-1-yl)-2-butenamide, N-[4-(3-chloro-4-fluorophenylamino)-7-(8-methyl-8-azabicyclo[3.2.1]octan-3-yloxy)quinazolin-6-yl]-acrylamide, N-[4-(3-chloro-4-fluorophenylamino)-7-(8-methyl-1-oxa-8-azaspiro[4.5]decan-3-yloxy)quinazolin-6-yl]-acrylamide, N-[4-(3-chloro-4-fluorophenylamino)-7-((8-methyl-1-oxa-8-azaspiro[4,5]decan-3-yl)methoxy)quinazolin-6-yl]-acrylamide, N-[4-(3-chloro-4-fluorophenylamino)-7-(8-methyl-1-oxa-8-azaspiro[4,5]decan-2-ylmethoxy)quinazolin-6-yl]-acrylamide, N-[4-(3-chloro-4-fluorophenylamino)-7-(2-((1R,5S,6S)-3-methyl-3-azabicyclo[3.1.0]hexan-6-ylethoxy)quinazolin-6-yl]-acrylamide, N-[4-(3-chloro-4-fluorophenylamino)-7-((2-methyloctahydrocyclopenta[c]pyrrol-4-yl)methoxy)quinazolin-6-yl]-acrylamide, N-[4-(3-chloro-4-fluorophenylamino)-7-((7-methyl-7-azabicyclo[2.2.1]heptan-2-yl)methoxy)quinazolin-6-yl]-acrylamide, N-[4-(3-chloro-4-fluorophenylamino)-7-(2-(3-methyl-3-azabicyclo[3.2.1]octan-8-yl)ethoxy)quinazolin-6-yl]-acrylamide, N-[4-(3-chloro-4-fluorophenylamino)-7-((5-methyl-5-azaspiro[2.4]heptan-1-yl)methoxy)quinazolin-6-yl]-acrylamide, N-[4-(3-chloro-4-fluorophenylamino)-7-((6-methyl-6-azaspiro[2.5]octan-1-yl)methoxy)quinazolin-6-yl]-acrylamide, N-[4-(3-chloro-4-fluorophenylamino)-7-(2-(6-methyl-6-azaspiro[2.5]octan-1-yl)ethoxy)quinazolin-6-yl]-acrylamide, (E)-N-[4-(3-chloro-4-fluorophenylamino)-7-(2-((1R,5S,6S)-3-methyl-3-azabicyclo[3.1.0]hexan-6-yl)ethoxy)quinazolin-6-yl]-2-butenamide, (E)-N-[4-(3-chloro-4-fluorophenylamino)-7-((7-methyl-7-azaspiro[3.5]nonan-2-yl)methoxy)quinazolin-6-yl]-2-butenamide, (E)-N-[4-(3-chloro-4-fluorophenylamino)-7-((7-methyl-7-azaspiro[3.5]nonan-2-yl)methoxy)quinazolin-6-yl]-2-pentenamide, N-[4-(3-chloro-4-fluorophenylamino)-7-((7-methyl-7-azaspiro[3.5]nonan-2-yl)methoxy)quinazolin-6-yl]-acrylamide, N-[4-(3-chloro-4-fluorophenylamino)-7-(2-(7-methyl-7-azaspiro[3.5]nonan-2-yl)ethoxy)quinazolin-6-yl]-acrylamide, (E)-N-(4-(3-chloro-4-fluorophenylamino)-7-((7-methyl-7-azaspiro[3.5]nonan-2-yl)methoxy)quinazolin-6-yl)-4-dimethylamino-2-butenamide, (E)-N-[4-(3-chloro-4-fluorophenylamino)-7-((2-(3-methyl-3-aza-bicyclo[3.1.0]-6-hexyl)-ethoxy)quinazolin-6-yl)-4-dimethylamino]-crotonamide, (E)-N-[4-(3-chloro-4-fluorophenylamino)-7-(((spiro[3.5]octan-2-yl)methoxy)quinazolin-6-yl)-4-dimethylamino]-crotonamide, and (E)-N-(7-(bicyclo[3.1.0]hexan-6-ylmethoxy)-4-(3-chloro-4-fluorophenylamino)quinazolin-6-yl)-4-(dimethylamino)but-2-enamide.

* * * * *